US012216124B2

(12) United States Patent
Chiu et al.

(10) Patent No.: US 12,216,124 B2
(45) Date of Patent: *Feb. 4, 2025

(54) CHROMOPHORIC POLYMER DOTS

(71) Applicant: University of Washington through its Center for Commercialization, Seattle, WA (US)

(72) Inventors: Daniel T. Chiu, Seattle, WA (US); Changfeng Wu, Seattle, WA (US); Xuanjun Zhang, Linköping (SE); Jiangbo Yu, Seattle, WA (US); Fangmao Ye, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 20 days.

This patent is subject to a terminal disclaimer.

(21) Appl. No.: 18/058,458

(22) Filed: Nov. 23, 2022

(65) Prior Publication Data
US 2023/0408526 A1    Dec. 21, 2023

Related U.S. Application Data

(63) Continuation of application No. 16/989,491, filed on Aug. 10, 2020, now Pat. No. 11,585,818, which is a
(Continued)

(51) Int. Cl.
*C09K 11/06* (2006.01)
*B82Y 15/00* (2011.01)
(Continued)

(52) U.S. Cl.
CPC ............ *G01N 33/588* (2013.01); *B82Y 15/00* (2013.01); *B82Y 30/00* (2013.01); *B82Y 40/00* (2013.01);
(Continued)

(58) Field of Classification Search
CPC ...................................................... C09K 11/06
See application file for complete search history.

(56) References Cited

U.S. PATENT DOCUMENTS 4,774,339 A    9/1988 Haugland et al.
4,946,778 A    8/1990 Ladner et al.
(Continued)

FOREIGN PATENT DOCUMENTS

CN          1541136 A    10/2004
CN        101302353 A    11/2008
(Continued)

OTHER PUBLICATIONS

Zhang. Synthesis and characterization of a novel water-soluble block copolymer with a rod-coil structure. Materials Letters 60 (2006) 679-684 (Year: 2006).*
(Continued)

*Primary Examiner* — Matthew E. Hoban
(74) *Attorney, Agent, or Firm* — Christensen O'Connor Johnson Kindness PLLC

(57) ABSTRACT

The present invention provides, among other aspects, stabilized chromophoric nanoparticles. In certain embodiments, the chromophoric nanoparticles provided herein are rationally functionalized with a pre-determined number of functional groups. In certain embodiments, the stable chromophoric nanoparticles provided herein are modified with a low density of functional groups. In yet other embodiments, the chromophoric nanoparticles provided herein are conjugated to one or more molecules. Also provided herein are methods for making rationally functionalized chromophoric nanoparticles.

20 Claims, 21 Drawing Sheets

Related U.S. Application Data continuation of application No. 15/167,513, filed on May 27, 2016, now Pat. No. 10,739,349, which is a continuation of application No. 13/865,924, filed on Apr. 18, 2013, now Pat. No. 9,382,473, and a continuation of application No. PCT/US2011/056768, filed on Oct. 18, 2011.

(60) Provisional application No. 61/394,259, filed on Oct. 18, 2010.

(51) Int. Cl.
| | |
|---|---|
| *B82Y 30/00* | (2011.01) |
| *B82Y 40/00* | (2011.01) |
| *C08G 61/12* | (2006.01) |
| *C08J 3/11* | (2006.01) |
| *C09K 11/02* | (2006.01) |
| *G01N 33/58* | (2006.01) |
| *H10K 85/10* | (2023.01) |

(52) U.S. Cl.
CPC ............ *C08G 61/126* (2013.01); *C08J 3/11* (2013.01); *C09K 11/025* (2013.01); *C09K 11/06* (2013.01); *H10K 85/115* (2023.02); *C08G 2261/12* (2013.01); *C08G 2261/1426* (2013.01); *C08G 2261/228* (2013.01); *C08G 2261/3142* (2013.01); *C08G 2261/3246* (2013.01); *C08G 2261/522* (2013.01); *C08G 2261/54* (2013.01); *C08G 2261/72* (2013.01); *C08G 2261/94* (2013.01); *C08J 2327/22* (2013.01); *C09K 2211/1425* (2013.01)

(56) References Cited

U.S. PATENT DOCUMENTS

| | | | |
|---|---|---|---|
| 5,723,218 | A | 3/1998 | Haugland et al. |
| 6,367,042 | B1 | 4/2002 | Phan et al. |
| 6,417,402 | B1 | 7/2002 | Das et al. |
| 7,432,298 | B2 | 10/2008 | Lam et al. |
| 7,462,325 | B2 * | 12/2008 | Hancock ............... C08G 61/02 422/82.08 |
| 7,985,426 | B1 | 7/2011 | Sung et al. |
| 8,067,506 | B2 | 11/2011 | Chen et al. |
| 8,367,042 | B2 | 2/2013 | Kim et al. |
| 9,382,473 | B2 * | 7/2016 | Chiu ............... B82Y 40/00 |
| 9,797,840 | B2 | 10/2017 | Chiu et al. |
| 9,810,693 | B2 | 11/2017 | Chiu et al. |
| 9,849,197 | B2 | 12/2017 | Saji et al. |
| 10,067,139 | B2 | 9/2018 | Chiu et al. |
| 10,150,841 | B2 | 12/2018 | Chiu et al. |
| 10,191,060 | B2 | 1/2019 | Chiu et al. |
| 10,739,349 | B2 * | 8/2020 | Chiu ............... C08G 61/126 |
| 11,585,818 | B2 * | 2/2023 | Chiu ............... B82Y 30/00 |
| 2002/0045045 | A1 | 4/2002 | Adams et al. |
| 2004/0018379 | A1 | 1/2004 | Kinlen |
| 2004/0131886 | A1 | 7/2004 | Marrocco et al. |
| 2005/0019265 | A1 | 1/2005 | Hammer et al. |
| 2005/0171289 | A1 | 8/2005 | Kataoka et al. |
| 2005/0255044 | A1 | 11/2005 | Lomnes et al. |
| 2006/0127929 | A1 | 6/2006 | Swager et al. |
| 2007/0031490 | A1 | 2/2007 | Loebenberg et al. |
| 2007/0224345 | A1 | 9/2007 | Metz et al. |
| 2008/0081192 | A1 | 4/2008 | Goh et al. |
| 2008/0085566 | A1 | 4/2008 | Swager et al. |
| 2008/0178763 | A1 | 7/2008 | Schwartz et al. |
| 2008/0199700 | A1 | 8/2008 | Anderson et al. |
| 2008/0242806 | A1 * | 10/2008 | Chen ............... C08L 71/02 526/260 |
| 2009/0075295 | A1 | 3/2009 | Lindsey |
| 2009/0130665 | A1 | 5/2009 | Sleiman et al. |
| 2009/0220434 | A1 | 9/2009 | Sharma |
| 2010/0016472 | A1 | 1/2010 | Wang et al. |
| 2010/0098902 | A1 | 4/2010 | Kotov et al. |
| 2010/0290999 | A1 | 11/2010 | Kim et al. |
| 2011/0159605 | A1 | 6/2011 | Whitten et al. |
| 2011/0278503 | A1 | 11/2011 | Janczewski et al. |
| 2011/0278536 | A1 | 11/2011 | Walker et al. |
| 2012/0015190 | A1 | 1/2012 | Goh et al. |
| 2012/0175571 | A1 | 7/2012 | Sarkar |
| 2012/0282632 | A1 | 11/2012 | Chiu et al. |
| 2013/0234067 | A1 | 9/2013 | Chiu et al. |
| 2013/0234068 | A1 | 9/2013 | Chiu et al. |
| 2013/0266957 | A1 | 10/2013 | Chiu et al. |
| 2014/0302516 | A1 | 10/2014 | Chiu et al. |
| 2014/0350183 | A1 | 11/2014 | Chiu et al. |
| 2015/0037259 | A1 | 2/2015 | Chiu et al. |
| 2016/0018395 | A1 | 1/2016 | Chiu et al. |
| 2016/0161475 | A1 | 6/2016 | Chiu et al. |
| 2019/0004056 | A1 | 1/2019 | Chiu et al. |
| 2019/0234953 | A1 | 8/2019 | Chiu et al. |

FOREIGN PATENT DOCUMENTS

| | | |
|---|---|---|
| CN | 101885913 A | 11/2010 |
| CN | 102791827 A | 11/2012 |
| JP | 2006525527 A | 11/2006 |
| JP | 2009-506188 A | 2/2009 |
| JP | 2011-500916 A | 1/2011 |
| JP | 2013168424 A | 8/2013 |
| JP | 2014-500891 A | 1/2014 |
| JP | 2017-082223 A | 5/2017 |
| JP | 6279902 B2 | 2/2018 |
| JP | 2018-151396 A | 9/2018 |
| JP | 6595974 B2 | 10/2019 |
| WO | 2007027159 A1 | 3/2007 |
| WO | 2007095506 A1 | 8/2007 |
| WO | 2008063378 A2 | 5/2008 |
| WO | 2009/051560 A1 | 4/2009 |
| WO | 2009107859 A2 | 9/2009 |
| WO | 2010006753 A2 | 1/2010 |
| WO | 2010075512 A1 | 7/2010 |
| WO | 2010075514 A1 | 7/2010 |
| WO | 20101099273 A1 | 9/2010 |
| WO | 2011057295 A2 | 5/2011 |
| WO | 2012054525 A2 | 4/2012 |
| WO | 2012118136 A1 | 9/2012 |
| WO | 2013101902 A2 | 7/2013 |
| WO | 2013116614 A1 | 8/2013 |
| WO | 2014153051 A1 | 9/2014 |

OTHER PUBLICATIONS

English translation of the Japanese Office Action mailed on Nov. 1, 2023, issued in the corresponding Japanese Application No. 2022-118555, filed on Oct. 18, 2011, 5 pages.

Moon, Joong Ho, McDaniel, William, Maclean, Paul et al. (2007). Live-cell-permeable poly (p-phenylene ethynylene) . Angewandte Chemie-International Edition, 46(43), 8223-8225. 10.1002/anie. 200701991.

Abdelwahed, et al. Freeze-drying of nanoparticles: formulation, process and storage considerations. Adv Drug Deliv Rev. Dec. 30, 2006;58(15):1688-713.

Benstead, et al. Addressing fluorescence and liquid crystal behaviour in multi-mesogenic BODIPY materials. New Journal of Chemistry. 2011; 35(7):1410-1417.

European search report and opinion dated May 31, 2016 for EP Application No. 12861954.

European search report and opinion dated Sep. 8, 2016 for EP Application No. 14770843.2.

Greenham et al., Efficient light-emitting diodes based on polymers with high electron affinities, Nature, vol. 365:628-630, published Oct. 14, 1993, print retrieved on Oct. 10, 2016.

Greenham, et al., Measurement of Absolute Photoluminescence Quantum Efficiencies in Conjugated Polymers, Chemical Physics Letters, Jul. 14, 1995, 241(1995) 89-96.

Huyal, et al., White emitting polyfluorene functionalized with azide hybridized on near-UV light emitting diode for high color rendering index, Optics Express , Jan. 21, 2008, 16(2):1115-24.

(56) References Cited

OTHER PUBLICATIONS

Meng, et al. Color tuning of polyfluorene emission with BODIPY monomers, Macromolecules 2009, 42:1995-2001.
Murcia, et al., Biofunctionalization of Fluorescent Nanoparticles, Nanotechnologies for the Life Sciences, 2005, vol. 1, 40 pages.
Nagai, et al. Highly luminescent BODIPY-based organoboron polymer exhibiting supramolecular self-assemble structure. J Am Chem Soc. Nov. 19, 2008;130(46):15276-8. doi: 10.1021/ja806939w.
Nagai, et al. Organoboron conjugated polymers. In Conjugated Polymer Synthesis: Methods and reactions. Ed. Yoshiki Chujo. Wiley-VCH Verlag GmbH & Co KGaA, Weinheim. 2010. 195-214.
Notice of allowance dated Jun. 16, 2017 for U.S. Appl. No. 13/687,813.
Notice of allowance dated Jun. 23, 2017 for U.S. Appl. No. 13/865,942.
Notice of allowance dated Aug. 29, 2017 for U.S. Appl. No. 13/508,981.
Notice of Allowance dated Oct. 19, 2017 for U.S. Appl. No. 13/508,981.
Office action dated Jan. 29, 2016 for AU Application 2012362466.
Office action dated Feb. 19, 2016 for CN Application 201280070923.3.
Office action dated Mar. 8, 2017 for AU Application No. 2015204342.
Office action dated Mar. 15, 2017 for JP Application No. 2013-535014.
Office action dated Mar. 29, 2016 for JP Application No. 2012-538915.
Office action dated Mar. 30, 2017 for U.S. Appl. No. 14/373,835.
Office action dated Apr. 5, 2017 for EP Application No. 15175146.8.
Office action dated Apr. 28, 2017 for U.S. Appl. No. 13/865,942.
Office action dated May 16, 2016 for U.S. Appl. No. 14/373,835.
Office action dated May 20, 2016 for EP Application No. 10829306.9.
Office action dated May 29, 2017 for CA Application No. 2,814,790.
Office action dated Jun. 6, 2017 for JP Application No. 2016-151438.
Office action dated Jun. 15, 2017 for CN Application No. 201180060824.2.
Office action dated Jun. 23, 2017 for CN Application No. 201480028351.1.
Office action dated Jul. 26, 2017 for CN Application No. 201280070923.3.
Office action dated Jul. 28, 2017 for EP Application No. 14770843.
Office action dated Sep. 21, 2017 for EP Application No. 15175146.8.
Office action dated Sep. 22, 2017 for EP Application No. 11835019.8.
Office action dated Sep. 26, 2016 for CN Application No. 201480028351.1.
Office action dated Sep. 27, 2016 for EP Application No. 11835019.8.
Office action dated Sep. 27, 2016 for JP Application 2014-550455.
Office action dated Oct. 20, 2016 for U.S. Appl. No. 13/687,813.
Office action dated Nov. 4, 2016 for CN Application No. 201280070923.3.
Office action dated Dec. 29, 2016 for U.S. Appl. No. 13/865,942.
Office action dated Jan. 30, 2017 for AU Application No. 2012362466.
Office action dated Feb. 22, 2017 for U.S. Appl. No. 13/508,981.
Office action dated Mar. 1, 2017 for U.S. Appl. No. 14/366,863.
Office action dated Sep. 13, 2016 for U.S. Appl. No. 14/373,835.
Office action dated Oct. 10, 2017 for U.S. Appl. No. 14/366,863.
Park, et al., White-Emitting Conjugated Polymer Nanoparticles with Cross-Linked Shell for Mechanical Stability and Controllable photometric Properties in Color-Conversion LED Applications, ACS Nano, 2011, 5(4):2483-92.
Riddle, et al. Signal-Amplifying Resonance Energy Transfer: A Dynamic Multichromophore Array for Allosteric Switching. Angewandte Chemie International Edition. 2007; 46(37):7019-7022.

Rong, et al. Multicolor fluorescent semiconducting polymer dots with narrow emissions and high brightness. Acs Nano. 2013; 7(1)L376-384.
Sun, et al. Lyophilization of semiconducting polymer dot bioconjugates. Anal Chem. May 7, 2013;85(9):4316-20. doi: 10.1021/ac4007123. Epub Apr. 19, 2013.
Yao, et al., Fluorescent Nanoparticles Comprising Amphiphilic Rod-Coil Graft Copolymers, Macromolecules, 2008, 41:1438-43.
Zhang, et al., Synthesis and characterization of a novel water-soluble block copolymer with a rod-coil structure, Materials Letters 60, (2006), pp. 679-684.
Zhu, et al. Efficient tuning nonlinear optical properties: Synthesis and characterization of a series of novel poly (aryleneethynylene) s co-containing BODIPY. Journal of Polymer Science Part A: Polymer Chemistry. 2008; 46(22):7401-7410.
Corrected Notice of Allowability dated Dec. 1, 2017 for U.S. Appl. No. 13/508,981.
Office Action dated Nov. 24, 2017 for CN Patent Application No. 201180060824.2.
Office Action dated Nov. 30, 2017 for U.S. Appl. No. 14/373,835.
Office Action dated Jan. 28, 2018 for EP Application No. 12861954.1.
U.S. Appl. No. 14/774,971 Office Action dated Feb. 16, 2018.
Australian Examination Report dated Jun. 13, 2018 for AU Application No. AU2017204805.
CA2814790 Office Action dated May 28, 2018.
CN 201280070923.3 Fourth Office Action dated Apr. 23, 2018 (w/ English translation).
CN 201480028351.1 Third Office Action dated Mar. 28, 2018 (w/ English translation).
CN 201610969596.5 First Office Action dated Jan. 22, 2018.
Co-pending U.S. Appl. No. 16/041,569, filed Jul. 20, 2018.
European search report with written opinion dated Oct. 24, 2018 for EP Application No. 18193806.
Green, et al. Simple conjugated polymer nanoparticles as biological labels. Proc. R. Soc. A. 2009. 465. 2751-2759; DOI: 10.1098/rspa.2009.0181. Published Jul. 27, 2009.
JP 2016-235598 Office Action dated Mar. 28, 2018 (w/ English translation).
Notice of allowance dated Jun. 27, 2018 for U.S. Appl. No. 14/366,863.
Notice of allowance dated Jul. 23, 2018 for U.S. Appl. No. 14/366,863.
Notice of allowance dated Aug. 8, 2018 for U.S. Appl. No. 14/373,835.
Notice of allowance dated Sep. 6, 2018 for U.S. Appl. No. 13/508,981.
Office action dated Jun. 29, 2018 for U.S. Appl. No. 14/774,971.
U.S. Appl. No. 14/373,835 Notice of Allowance dated Apr. 24, 2018.
JP 2016-235598 Office Action dated Oct. 3, 2018 (w/ English translation).
Office action dated Dec. 4, 2018 for U.S. Appl. No. 16/041,569.
Co-pending U.S. Appl. No. 16/209,729, filed Dec. 4, 2018.
AU 2017200592 Office Action dated Mar. 29, 2018.
Australian Examination Report dated Oct. 25, 2018 for AU Application No. AU2017200592.
CN201080060982.3 Office Action dated Dec. 1, 2014.
CN201080060982.3 Office Action dated Jan. 14, 2014.
CN201080060982.3 Office Action dated Jan. 5, 2016.
CN201080060982.3 Office Action dated Jul. 31, 2015.
Japanese office action dated Jan. 8, 2019 for JP Application No. 2017092547.
Notice of allowance dated Dec. 26, 2018 for U.S. Appl. No. 13/508,981.
Office action dated Mar. 1, 2019 for U.S. Appl. No. 14/774,971.
Office action dated Nov. 6, 2018 for EP Application No. 14770843.
CN201610969596.5 Office Action dated Aug. 23, 2018.
Australian examination report dated Apr. 8, 2016 for AU Aoolication 2015204342.
European office action dated Mar. 2, 2016 for EP Aoolication No. 11835019.8.
Chinese office action dated Sep. 29, 2016 for CN Application No. 20118006824.2.
International search report and written opinion dated Mar. 27, 2013 for PCT/US2012/071767.

(56) References Cited

OTHER PUBLICATIONS

Notice On The Second Office Action as mailed on Oct. 11, 2021, issued in corresponding CN Application No. 201810927246.1, filed Oct. 18, 2011, 14 pages.
Notice of Reasons for Refusal as mailed on Sep. 6, 2021 issued in corresponding JP Application No. 2019-177287, filed Oct. 18, 2011, 8 pages.
First Chinese Office Action mailed Feb. 8, 2021 issued in corresponding Application No. 201810927246.1, filed Oct. 18, 2011, 5 pages.
Thivierge, et al. Brilliant BODIPY-fluorene Copolymers With Dispersed Absorption and Emission Maxima. Macromolecules. May 24, 2011;44(10):4012-4015.
Thomas, et al. Chemical sensors based on amplifying fluorescent conjugated polymers. Chem Rev. Apr. 2007; I07(4):1339-86. Epub Mar. 27, 2007.
Tian, et al. Amplified energy transfer in conjugated polymer nanoparticle tags and sensors. Nanoscale. Oct. 2010;2(10):1999-2011. doi: 10.1039/c0nr00322k. Epub Aug. 10, 2010.
Tsien. The green fluorescent protein. Annu Rev Biochem. 1998;67:509-44.
Tuncel, et al. Conjugated polymer nanoparticles. Nanoscale. Apr. 2010;2(4):484-94. doi: 10.1039/b9nr00374f. Epub Mar. 6, 2010.
Veiseh, et al. Specific targeting of brain tumors with an optical/magnetic resonance imaging nanoprobe across the blood-brain barrier. Cancer Res. Aug. 1, 2009;69(15):6200-7. doi: 10.1158/0008-5472.CAN-09-1157. Epub Jul. 28, 2009.
Wang, et al. Bioconjugation by copper(I)-catalyzed azide-alkyne [3 + 2] cycloaddition. J Am Chem Soc. Mar. 19, 2003;125(11):3192-3.
Wang, et al. Non-blinking semiconductor nanocrystals. Nature. Jun. 4, 2009;459(7247):686-9. doi: 10.1038/nature08072.
Wang, et al. Watching silica nanoparticles glow in the biological world. Anal. Chem. 2006;78(3):646-654.
Wu, et al. Bioconjugation ofultrabright semiconducting polymer dots for specific cellular targeting. J Am Chem Soc. Nov. 3, 2010;132(43): 15410-7. doi: 10.1021/ja107196s.
Wu, et al. Conjugated polymer dots for multiphoton fluorescence imaging. J Am Chem Soc. Oct. 31, 2007;129(43):12904-5. Epub Oct. 6, 2007.
Wu, et al. Corrigendum: Immunofluorescent labeling of cancer marker Her2 and other cellular targets with semiconductor quantum dots. Nat Biotechnol. Jan. 2003;21(1):41-6. Epub Dec. 2, 2002.
Wu, et al. Design of highly emissive polymer dot bioconjugates for in vivo tumor targeting. Angew Chem Int Ed Engl. Apr. 4, 2011;50(15):3430-4. doi: 10.1002/anie.201007461. Epub Mar. 4, 2011.
Wu, et al. Energy Transfer in a Nanoscale Multichromophoric System: Fluorescent Dye-Doped Conjugated Polymer Nanoparticles. Phys Chem C Nanomater Interfaces. Feb. 14, 2008;112(6):1772-1781.
Wu, et al. Energy transfer mediated fluorescence from blended conjugated polymer nanoparticles. J Phys Chem B. Jul. 27, 2006;110(29):14148-54.
Wu, et al. Highly fluorescent semiconducting polymer dots for biology and medicine. Angew Chem Int Ed Engl. Mar. 11, 2013;52(11):3086-109. doi: 10.1002/anie.201205133. Epub Jan. 10, 2013.
Wu, et al. Immunofluorescent labeling of cancer marker Her2 and other cellular targets with semiconductor quantum dots. NatBiotechnol. Jan. 2003;21(1):41-6. Epub Dec. 2, 2002.
Wu, et al. Multicolor conjugated polymer dots for biological fluorescence imaging. ACS Nano. Nov. 25, 2008;2(11):2415-23. doi: 10.1021/nn800590n.
Wu, et al. Preparation and encapsulation of highly fluorescent conjugated polymer nanoparticles. Langmuir. Mar. 28, 2006;22(7):2956-60.
Wu, et al. Ratiometric single-nanoparticle oxygen sensors for biological imaging. Angew Chem Int Ed Engl. 2009;48(15):2741-5. doi: 10.1002/anie.200805894.

Wu, et al. Swelling-controlled polymer phase and fluorescence properties of polyfluorene nanoparticles. Langmuir. Jun. 3, 2008;24(11):5855-61. doi: 10.1021/la8000762. Epub May 7, 2008.
Wu, et al. Ultrabright and bioorthogonal labeling of cellular targets using semiconducting polymer dots and click cAngew Chem Int Ed Engl. Dec. 3, 2010;49(49):9436-40. doi: 10.1002/anie.201004260. hemistry.
WU. Fluorescent conjugated polymer dots for single molecule imaging and sensing application A Dissertation presented to the Graduate School of Clemson University. Dec. 1, 2008. pp. 1-182. http://etd.lib.clemson.edu/documents/1239895063/Wu_clemson_005D_10023.pdf.
Xie, et al. Luminescent CdSe—ZnSe quantum dots as selective $Cu^{2+}$ probe. Spectrochimica Acta Part A. 2004; 60:2527-2530.
Xing, et al. Bioconjugated quantum dots for multiplexed and quantitative immunohistochemistry. Nat Protoc. 2007;2(5):1152-65.
Yang, et al. Deep-red electroluminescent polymers: Synthesis and characterization of new low-band-gap conjugated copolymers for light-emitting diodes and photovoltaic devices. Macromolecules 2005; 38:244-253.
Yao, et al. Blinking and nouradiant dark fraction of water-soluble quantum dots in aqueous solution. Proc Natl Acad Sci US A. Oct. 4, 2005;102(40):14284-9. Epub Sep. 16, 2005.
Ye, et al. A compact and highly fluorescent orange-emitting polymer dot for specific subcellular imaging. Chem Commun (Camb). Feb. 7, 2012;48(12):1778-80. doi: 10.1039/c2ccl6486h. Epub Jan. 4, 2012.
Ye, et al. Ratiometric temperature sensing witll semiconducting polymer dots. J Am Chem Soc. Jun. 1, 2011;133(21):8146-9. doi: 10.1021/ja202945g. Epub May 11, 2011.
Yu, et al. Nanoscale 3D tracking witll conjugated polymer nanoparticles. J Am Chem Soc. Dec. 30, 2009;131(51):18410-4. doi: 10.1021/ja907228q.
Yu, et al. Stable functionalization of small semiconducting polymer dots via covalent cross-linking and their application for specific cellular imaging. Adv Mater. Jul. 10, 2012;24(26):3498-504. doi: 10.1002/adma.201201245. Epub Jun. 11, 2012.
Zhang, et al. Importance of having low-density functional groups for generating high-performance semiconducting polymer dots. ACS Nano. Jun. 26, 2012;6(6):5429-39. doi: 10.1021/nn301308w. Epub May 24, 2012.
Zheng. Detection of the cancer marker CD146 expression in melanoma cells witll semiconductor quantum dot label (Abstract). J Biomed Nanotechnol. Aug. 2010;6(4):303-11.
Abbel, et al. Multicolour self-assembled particles of fluorene-based bolaamphiphiles. Chem Commun (Camb). Apr. 7, 2009;(13):1697-9. soi: 10.1039/b822943k. Epub Feb. 17, 2009.
Achari, et al. 1.67-A X-ray structure of the B2 immunoglobulin-binding domain of streptococcal protein G and comparison to the NMR structure of the B1 domain. Biochemistry, Nov. 3, 1992;31(43):10449-57.
Agard, et al. A comparative study of bioorthogonal reactions with azides. ACS Chem Biol. Nov. 21, 2006:1(10):644-8.
Akerstrom, et al. A physicochemical study of protein G, a molecule with unique immunoglobulin G-binding properties. J. Biol Chem. Aug. 5, 1986;261(22):10240-7.
Alivistatos, et al. Quantum dots as cellular probes. Annu Rev Biomed Eng. 2005;7:55-76.
Ausborn, et al. The protective effect of free and membrane-bound cryoprotectants during freezing and freeze-drying of liposomes. Journal of Controlled Release. 1994;30:105-116.
Baier, et al. Fluorescent conjugated polymer nanoparticles by polymerization in miniemulsion. J Am Chem Soc. Oct. 14, 2009;131(40):14267-73. doi: 10.102 1/ja905077c.
Berlier, et al. Quantitative comparison of long-wavelenglh Alexa Fluor dyes to Cy dyes: fluorescence of the dyes and theirbioconjugates. J Histochem Cytochem. Dec. 2003;51(12):1699-712.
Bernardin, et al. Copper-free click chemistry for highly luminescent quantum dot conjugates: application to in vivo metabolic imaging. Bioconjug Chem. Apr. 21, 2010;21(4):583-8. doi: 10.1021/bc900564w.

(56) References Cited

OTHER PUBLICATIONS

Best. Click chemistry and bioorthogonal reactions: unprecedented selectivity in the labeling of biological molecules. Biochemistry. Jul. 21, 2009;48(28):6571-84. doi: 10.1021/bi9007726.

Bird, et al. Single-chain antigen-binding proteins. Science. Oct. 21, 1988;242(4877):423-6.

Boyere, et al. Elaboration of drug nanocarriers based on a glucosamine labeled amphiphilic polymer. Polymer Chemistry. 2014; 5:3030-3037.

Breidenbach, et al. Targeted metabolic labeling of yeast N-glycans with unnatural sugars. Proc Natl Acad Sci US A. Mar. 2, 2010;107(9):3988-93. doi: 10.1073/pnas.0911247107. Epub Feb. 8, 2010.

Bruchez, et al. Semiconductor nanocrystals as fluorescent biological labels. Science. Sep. 25, 1998;281(5385):2013-6.

Caruso. Nanoengineering of Particle Surfaces. Adv. Mater. 2001; 13:11-22.

Chalfie, et al. Green fluorescent protein as a marker for gene expression. Science. Feb. 11, 1994;263(5148):802-5.

Chan, et al. Copper(II) and iron(II) ion sensing with semiconducting polymer dots. Chem Commun (Camb). Mar. 14, 2011;47(10):2820-2. doi: 10.1039/c0cc04929h. Epub Jan. 14, 2011.

Chan, et al. Development of ultrabright semiconducting polymer dots for ratiometric pH sensing. Anal Chem. Feb. 15, 2011;83(4):1448-55. doi: 10.1021/acl03140x. Epub Jan. 18, 2011.

Chan, et al. Hybrid semiconducting polymer dot-quantum dot with narrow-band emission, near-infrared fluorescence, and high brightness. J Am Chem Soc. May 2, 2012;134(17):7309-12. doi: 10.1021/ja3022973. Epub Apr. 23, 2012.

Chan, et al. Quantum dot bioconjugates for ultrasensitive nonisotopic detection. Science. Sep. 25, 1998;281(5385):2016-8.

Chan, et al. Ultrasensitive copper(II) detection using plasmon-enhanced and photo-brightened luminescence of CdSe quantum dots. Anal Chem. May 1, 2010;82(9):3671-8. doi: 10.1021/ac902985p.

Chen, et al. Highly sensitive biological and chemical sensors based on reversible fluorescence quenching in a conjugated polymer. Proc Natl Acad Sci U S A Oct. 26, 1999;96(22): 12287-92.

Choi, et al. Design considerations for tumour-targeted nanoparticles. Nat Nanotechnol. Jan. 2010;5(1):42-7. doi: 10.1038/nnano.2009.314. Epub Nov. 1, 2009.

Choi, et al. Renal clearance of quantum dots. Nat Biotechnol. Oct. 2007;25(10): 1165-70. Epub Sep. 23, 2007.

Clafton, et al. Chemical defects in the highly fluorescent conjugated polymer dots. Langmuir. Dec. 7, 2010;26(23):17785-9. doi: 10.1021/la103063p. Epub Nov. 11, 2010.

Collini, et al. Coherent intrachain energy migration in a conjugated polymer at room temperature. Science. Jan. 16, 2009;323(5912):369-73. doi: 10.1126/science.1164016.

Derfus, et al. Probing the Cytotoxicity of Semiconductor Quantum Dots. Nano Letters. 2004; 4(1):11-18.

Dieterich, et al. Selective identification of newly synthesized proteins in mammalian cells using bioorthogonal noncanonical amino acid tagging (BONCAT). Proc Natl Acad Sci US A Jun. 20, 2006;103(25):9482-7. Epub Jun. 12, 2006.

Dube, et al. Probing mucin-type 0-linked glycosylation in living animals. Proc Natl Acad Sci US A Mar. 28, 2006;103(13):4819-24. Epub Mar. 20, 2006.

European search report and opinion dated Mar. 19, 2014 for EP Application No. 11835019.8.

European search report and opinion dated Aug. 12, 2015 for EP Application No. 15175146.8.

European search report and opinion dated Sep. 18, 2013 for EP Application No. 10829306.9.

European search report and opinion dated Oct. 8, 2015 for EP Application No. 13743132.6.

Fan, et al. Beyond superquenching: hyper-efficient energy transfer from conjugated polymers to gold nanoparticles. Proc Natl Acad Sci US A May 27, 2003;100(11):6297-301. Epub May 15, 2003.

Fernandez-Suarez, et al. Fluorescent probes for super-resolution imaging in living cells. Nat Rev Mol Cell Biol. Dec. 2008;9(12):929-43. doi: 10.1038/urm253I. Epub Nov. 12, 2008.

Fernando, et al. Mechanism of cellular uptake of highly fluorescent conjugated polymer nanoparticles. Biomacromolecules. Oct. 11, 2010;11(10):2675-82. doi:10.102 I/bm1007 I 03.

Friend, et al. Electroluminescence in conjugated polymers. Nature. 1999; 397:121-128.

Giepmans, et al. The fluorescent toolbox for assessing protein location and function. Science. Apr. 14, 2006;312(5771):217-24.

Green. Avidin and streptavidin. Metllods Enzymol. Wilchek and Bayer. New York, Academic Press, Inc. 1990;184:51-67.

Gunes, et al. Conjugated polymer-based organic solar cells. Chem Rev. Apr. 2007; 107(4):1324-38.

Han, et al. Development of a bioorthogonal and highly efficient conjugation method for quantum dots using tetrazine-norbomene cycloaddition. J Am Chem Soc. Jun. 16, 2010;132(23):7838-9. doi: 10.1021/ja101677r.

Hashim, et al. Luminescent quantum-dot-sized conjugated polymer nanoparticles—nanoparticle formation in miniemulsion system. Journal of Materials Chemistry. 2011; 21: 1797-1803.

Hermanson. Bioconjugate techniques, Academic Press, San Diego, 1996; Ch 13, 570-591.

Hou, et al. Novel red-emitting fluorene-based copolymers. Journal of Materials Chemistry. 2002; 12:2887-2892.

Hou, et al. Synthesis and electroluminescent properties of high-efficiency saturated red emitter based on copolymers from fluorene and 4,7-di(4-hexylthien-2-yl)-2,1,3-benzothiadiazole, Macromolecules. 2004; 37:6299-6305.

Howarth, et al. Monovalent, reduced-size quantum dots for imaging receptors on living cells. Nat Methods. May 2008;5(5):397-9. doi: 10.1038/nmeth.1206. Epub Apr. 20, 2008.

Howes, et al. Colloidal and optical stability of PEG-capped and phospholipid-encapsulated semiconducting polymer nanospheres in different aqueous media. PhotochemPhotobiol Sci. Aug. 2010;9(8):1159-66. doi: 10.1039/c0pp00106f. Epub Jun. 29, 2010.

Howes, et al. Magnetic conjugated polymer nanoparticles as bimodal imaging agents. J Am Chem Soc. Jul. 21, 2010;132(28):9833-42. doi: 10.1021/ja1031634.

Howes, et al. Phospholipid encapsulated semiconducting polymer nanoparticles: their use in cell imaging and protein attachment. J Am Chem Soc. Mar. 24, 2010;132(11):3989-96. doi: 10.1021/ja1002179.

Howes, et al. Synthesis, characterisation and intracellular imaging of PEG capped BEHP-PPV nanospheres. Chem Commun (Camb). May 14, 2009;(18):2490-2. doi: 10.1039/b903405f. Epub Apr. 2, 2009.

International preliminary report on patentability dated Apr. 23, 2013 for PCT/US2011/056768.

International search report and written opinion dated Apr. 9, 2013 for PCT/US2013/024300.

International search report and written opinion dated Jun. 26, 2012 for PCT/US2011/056768.

International search report and written opinion dated Jul. 28, 2011 for PCT/US2010/056079.

International search report and written opinion dated Aug. 22, 2014 for PCT/US2014/028846.

Jin, et al. Generation of functionalized and robust semiconducting polymer dots with polyelectrolytes. Chem Commun (Camb). Mar. 28, 2012;48(26):3161-3. doi: 10.1039/c2ccl7703j. Epub Feb. 20, 2012.

Jin, et al. Near-infrared fluorescent dye-doped semiconducting polymer dots. ACS Nano. Feb. 22, 2011;5(2):1468-75. doi: 10.1021/nn103304m. Epub Jan. 31, 2011.

Jin, et al. Silica Nanoparticles with Continuously Tunable Sizes: Synthesis and Size Effects on Cellular Imaging. Chem. Mater. 2008, 20:4411-4419.

Johnston, et al. Layer-by-layer engineered capsules and their applications. Curr. Opin. Colloid Interface Sci. 2006;11:203-209.

Kaeser, et al. Fluorescent nanoparticles based on self-assembled pi-conjugated systems. Adv Mater. Jul. 27, 2010;22(28):2985-97. doi: 10.1002/adma.201000427.

(56) References Cited

OTHER PUBLICATIONS

Kietzke, et al. Novel approaches to polymer blends based on polymer nanoparticles. Nat Mater. Jun. 2003;2(6):408-12.

Kim, et al. Conjugated polymer nanoparticles for biomedical in vivo imaging. Chem Commun (Camb). Mar. 14, 2010;46(10):1617-9. doi: 10.1039/b923309a. Epub Jan. 12, 2010.

Kolb, et al. Click Chemistry: Diverse Chemical Function from a Few Good Reactions. w Chem Int Ed Engl. Jun. 1, 2001;40(11):2004-2021.

Kolb, et al. The growing impact of click chemistry on drug discovery. Drug Discov Today. Dec. 15, 2003;8(24):1128-37.

Kumar, et al. Photon antibunching from oriented semiconducting polymer nanostructures. J Am Chem Soc. Mar. 24, 2004;126(11):3376-7.

Laughlin, et al. Imaging the glycome. Proc Natl Acad Sci U S A. Jan. 6, 2009;106(1):12-7. doi: 10.1073/pnas.0811481106. Epub Dec. 22, 2008.

Lee, et al. Recent advances in fluorescent and colorimetric conjugated polymer-based biosensors. Analyst. Sep. 2010;35(9):2179-89. doi: 10.1039/c0an00239a. Epub Jun. 11, 2010.

Li, et al. Polymer encapsulated conjugated polymer nanoparticles for fluorescence bioimaging. Journal of Materials Chemistry 2012; 22:1257-1264.

McCafferty, et al. Phage antibodies: filamentous phage displaying antibody variable domains. Nature. Dec. 6, 1990;348(6301):552-4.

Michalet, et al. Quantum dots for live cells, in vivo imaging, and diagnostics. Science. Jan. 28, 2005;307(5709):538-44.

Moon, et al. Conjugated polymer nanoparticles for small interfering RNA delivery. Chem Commun (Camb). Aug. 7, 2011;47(29):8370-2. doi: 10.1039/c1cc10991j. Epub Jun. 22, 2011.

Moon, et al. Live-cell-permeable poly(p-phenylene ethynylene). Angew Chem Int Ed Engl. 2007;46(43):8223-5.

Moses, et al. The growing applications of click chemistry. Chem Soc Rev. Aug. 2007;36(8):1249-62. Epub May 3, 2007.

Nirmal, et al. Fluorescence intermittency in single cadmium selenide nanocrystals. Nature. 1996; 383:802-804. doi:10.1038/383802a0.

Office action dated Feb. 2, 2016 for CN Application No. 201180068242.

Office action dated Feb. 4, 2015 for CN Application No. 201180068242.

Office action dated Apr. 28, 2014 for AU Application No. 2011317142.

Office action dated May 30, 2014 for CN Application No. 201180068242.

Office action dated Aug. 4, 2015 for CN Application No. 201180068242.

Office action dated Dec. 3, 2015 for JP Application No. 2013-535014.

Palacios, et al. Charging and discharging of single conjugated-polymer nanoparticles. Nat Mater. Sep. 2007;6(9):680-5. Epub Jul. 22, 2007.

Pecher, et al. Nanoparticles of conjugated polymers. Chem Rev. Oct. 13, 2010;110(10):6260-79. doi: 10.1021/cr100132y.

Pepperkok, et al. High-throughput fluorescence microscopy for systems biology. Nat Rev Mol Cell Biol. Sep. 2006;7(9):690-6. Epub Jul. 19, 2006.

Poon, et al. Controlling in vivo stability and biodistribution in electrostatically assembled nanoparticles for systemic delivery. Nano Lett. May 11, 2011;11(5):2096-103. doi: 10.1021/nl200636r. Epub Apr. 27, 2011.

Poon, et al. Layer-by-layer nanoparticles with a pH-sheddable layer for in vivo targeting of tumor hypoxia. ACS Nano. Jun. 28, 2011;5(6):4284-92. doi: 10.1021/nn200876f. Epub Apr. 29, 2011.

Pras, et al. Photoluminescence of 2,7-poly(9,9-dialkylfluorene-co-fluorenone) nanoparticles: effect of particle size and inert polymer addition. Langmuir. Sep. 21, 2010;26(18):14437-42. doi: 10.1021/la1011742.

Prescher, et al. Chemical remodelling of cell surfaces in living animals. Nature. Aug. 19, 2004;430(7002):873-7.

Prescher, et al. Chemistry in living systems. Nat Chem Biol. Jun. 2005;I(I):13-21.

Pu, et al. Fluorescent conjugated polyelectroltyes forbioimaging. Advanced Functional Materials. 2011; 21:3408-3423.

Pu, et al. Fluorescent single-molecular core-shell nanospheres of hyperbranched conjugated polyelectrolyte for live-cell imaging. Chem. Mater. 2009;21:3816-3822.

Que, et al. Metals in neurobiology: probing their chemistry and biology with molecular imaging. Chem Rev. May 2008;108(5):1517-49. doi: 10.1021/cr078203u. Epub Apr. 22, 2008.

Rahim, et al. Conjugated Polymer Nanoparticles for Two-Photon Imaging of Endothelial Cells in a Tissue Model. Adv. Mater. 2009; 21(34):3492-3496.

Resch-Genger, et al. Quantum dots versus organic dyes as fluorescent labels. Nat Methods. Sep. 2008;5(9):763-75. doi: 10.1038/nmeth.1248.

Sadtler, et al. Selective facet reactivity during cation exchange in cadmium sulfide nanorods. J Am Chem Soc. Apr. 15, 2009;131(14):5285-93. doi: 10.1021/ja809854q.

Sigma Aldrich. Product Information Triton X-1 00. Apr. 21, 1999. Retrieved at http://www.sigmaaldrich.com/content!dam/sigmaaldrich/docs/Sigma/Product_Informati on_Sheet/1 /t8532pis.pdf on Mar. 14, 2014.

Sletten, et al. Bioorthogonal chemistry: fishing for selectivity in a sea of functionality. Angew Chem Int Ed Engl. 2009;48(38):6974-98. doi: 10.1002/anie.200900942.

Smith, et al. Investigating lyophilization of lipid nanocapsules with fluorescence correlation spectroscopy. Investigating lyophilization of lipid nanocapsules with fluorescence correlation spectroscopy.

Speers, et al. Activity-based protein profiling in vivo using a copper(i)-catalyzed azide-alkyne [3 + 2] cycloaddition. J Am Chem Soc. Apr. 23, 2003;125(16):4686-7.

Szymanski, et al. Single molecule nanoparticles of the conjugated polymer MEH-PPV, preparation and characterization by near-field scanning optical microscopy. J Phys Chem B. May 12, 2005;109(18):8543-6.

Extended European Search Report mailed on Nov. 8, 2024, issued in European Application No. 24204747.0, filed on Oct. 18, 2011; 10 pages.

* cited by examiner

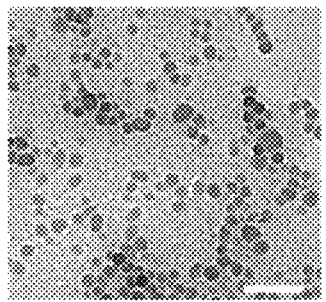
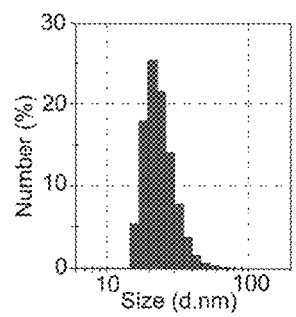
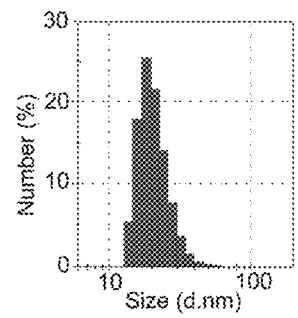
FIG. 9A    FIG. 9D    FIG. 9G
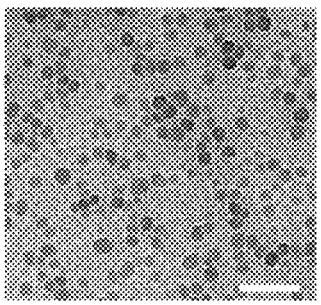
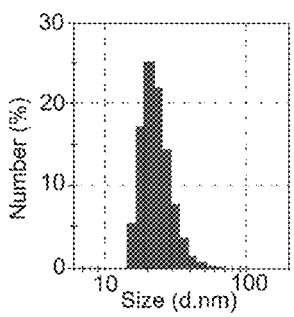
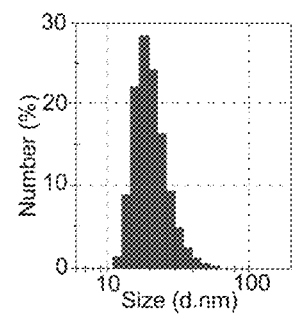
FIG. 9B    FIG. 9E    FIG. 9H
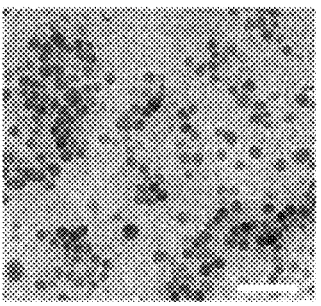
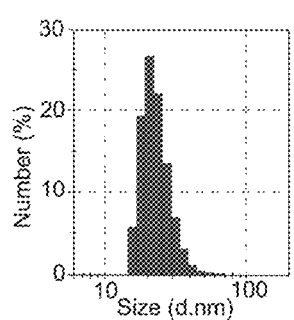
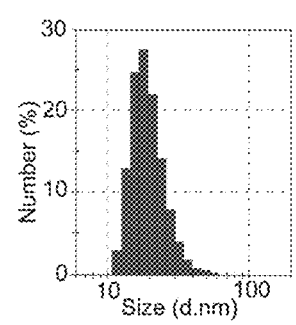
FIG. 9C    FIG. 9F    FIG. 9I

|  | PFBT-C2 | PFBT-C14 | PFBT-C50 |
|---|---|---|---|
| Size (nm) | 21 | 21 | 21 |
| ξ (mV)[a] | -50.2 | -54.4 | -57.5 |
| Abs ($10^{-13}$cm$^2$)[b] | 2.69 | 2.36 | 1.17 |
| Φ (%)[c] | 30 | 23 | 17 |
| B (counts)[d] | 3350 | 2960 | 610 | a, zeta potential; b, absorption cross-section estimated from absorption spectra; c, fluorescence quantum yield; d, single particle brightness (CCD counts/0.1s)

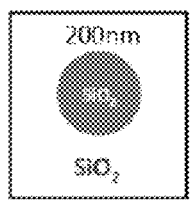
FIG. 20A
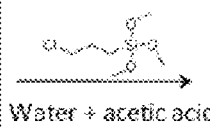
FIG. 20B
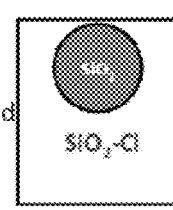
FIG. 20C
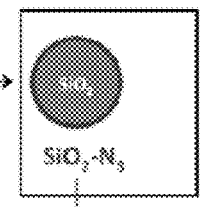
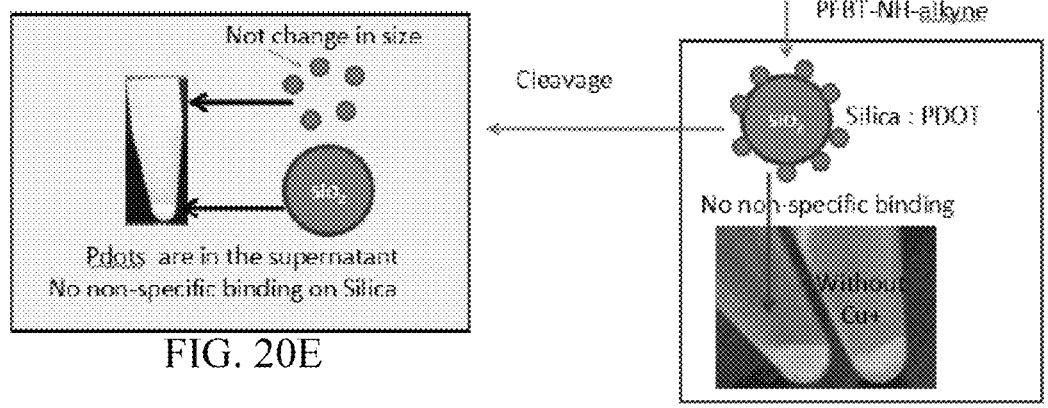
FIG. 20D
FIG. 20E
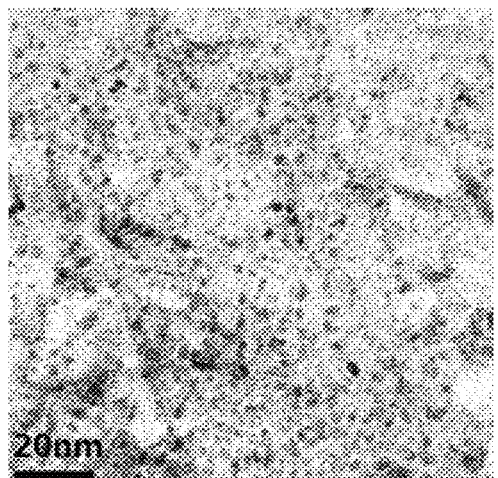
FIG. 20F

CHROMOPHORIC POLYMER DOTS

CROSS-REFERENCE

This application is a continuation application of U.S. application Ser. No. 16/989,491, filed Aug. 10, 2020, which is a continuation of U.S. application Ser. No. 15/167,513, filed May 27, 2016, which is a continuation application of U.S. application Ser. No. 13/865,924, filed Apr. 18, 2013, now U.S. Pat. No. 9,382,473, issued Jul. 5, 2016, which is a continuation application of International Application No. PCT/US11/56768, file on Oct. 18, 2011, which claims priority from U.S. Provisional Application No. 61/394,259 filed on Oct. 18, 2010, the content of each of which is hereby incorporated by references in its entirety.

STATEMENT AS TO FEDERALLY SPONSORED RESEARCH

This invention was made with Government support under grant numbers R21CA147831 and R01NS062725, awarded by the National Institutes of Health. The government has certain rights in the invention.

BACKGROUND OF THE INVENTION

Advances in understanding biological systems have relied on applications of fluorescence microscopy, flow cytometry, versatile biological assays, and biosensors. These experimental approaches make extensive use of organic dye molecules as probes. But intrinsic limitations of these conventional dyes, such as low absorptivity and poor photostability, have posed great difficulties in further developments of high-sensitivity imaging techniques and high-throughout assays. As a result, there has been considerable interest in developing brighter and more photostable fluorescent nanoparticles. For example, inorganic semiconducting quantum dots (Qdots) are under active development and now commercially available from Life Technologies (Invitrogen). (Bruchez, M.; Moronne, M.; Gin, P.; Weiss, S.; Alivisatos, A. P, Science 1998, 281, 2013-2016. Michalet, X.; Pinaud, F. F.; Bentolila, L. A.; Tsay, J. M.; Doose, S.; Li, J. J.; Sundaresan, G.; Wu, A. M.; Gambhir, S. S.; Weiss, S. Science 2005, 307, 538-544.) An alternative fluorescent nanoparticle is dye doped latex spheres, which exhibit improved brightness and photostability as compared to single fluorescent molecules because of multiple dye molecules per particle and the protective latex matrix. (Wang, L.; Wang, K. M.; Santra, S.; Zhao, X. J.; Hilliard, L. R.; Smith, J. E.; Wu, J. R.; Tan, W. H. Anal. Chem. 2006, 78, 646-654).

Fluorescence semiconducting polymer dots exhibit significant improvement in fluorescence brightness and photostability as compared to Qdots and dye-loaded latex beads. (Wu, C.; Szymanski, C.; Cain, Z.; McNeill, J. J. Am. Chem. Soc. 2007, 129, 12904-12905. Wu, C.; Bull B.; Szymanski, C.; Christensen, K.; McNeill, J. ACS Nano 2008, 2, 2415-2423.) The fluorescent polymer dots possess arguably the highest fluorescence brightness/volume ratios of any nanoparticle to date, owing to a number of favorable characteristics of semiconducting polymer molecules, including their high absorption cross sections, high radiative rates, high effective chromophore density, and minimal levels of aggregation-induced fluorescence quenching, resulting in fluorescence quantum yields that can be in excess of 70%, even for pure solid films. The use of fluorescent polymer dots as fluorescent probes also confers other useful advantages, such as the lack of heavy metal ions that could leach out into solution and which would be toxic for living organisms or biological cells.

However, a great bottleneck in nanoparticle development is the controlled chemical functionalization. There are two sets of challenges here. The first challenge is simply the design and introduction of functional groups into the side chain and backbone of the conjugated or semiconducting polymer without adversely affecting the collapse (as well as the stability and performance) of the polymer into a nanoparticle form while orienting the functional groups on the particle surface for bioconjugation, which is needed for most applications towards cellular labeling.

Previous attempts at introducing functional groups onto chromophoric polymer dots involved functionalizing the side chains of the polymer with hydrophilic functional groups at a high density (e.g. half of the monomeric units of the polymer has at least one side chain functionalized with a functional group). Although it has been claimed that the chromophoric polymers functionalized in this fashion can be formed into nanoparticles, the resulting nanoparticles tend to aggregate and degrade over time, and thus are in fact not stable (Moon et al. Angewandte Chemie. 2007, 46, 8223-8225). In fact, the heavily functionalized chromophoric polymers are more like conjugated polyelectrolytes because of the hydrophilic nature of the functional groups or side chains, and these nanoparticles are actually loose aggregates of polymers that are more like polyelectrolyte molecules (Moon et al. Chem. Communications 2011, 47, 8370-8372). The loose aggregates are formed without involving too much of polymer chain folding, and their loose structure is different from the compact chromophoric polymer dots collapsed from hydrophobic polymers. Correspondingly, these nanoparticles are unstable and offer poor performance for fluorescence labeling, and their aggregation behaviors are affected by polymer concentration, ionic strength, and temperature (Moon et al. Chem. Communications 2011, 47, 8370-8372). Furthermore, the nanoparticle formation of the heavily functionalized chromophoric polymers can require the use of harsh conditions (e.g. high concentration of acids), and this fact is supported by the common accepted understanding of polyelectrolyte conformation: the charges on a polyelectrolyte chain will repel each other (caused by Coulomb repulsion and/or solvation of the hydrophilic moieties), which causes the chain to adopt a more expanded, rigid-rod-like conformation. If the solution contains a great deal of added salt or acid, the charges will be screened and consequently the polyelectrolyte chains will associate with each other to form loose aggregates. As a result, chromophoric polymer dots generated from polymers that are more like conjugated polyelectrolytes generally are difficult to form (require harsh conditions such as acids), and once formed, the loose aggregates are unstable over time and offer poor performance, and their aggregation nature are affected by many factors such as polymer concentration, ionic strength, and temperature (Moon et al. Chem. Communications 2011, 47, 8370-8372), which limits the shelf life of these particles and degrades their performance towards biological applications. Polymers that are more like conjugated polyelectrolytes also have poor solubility in an organic solvent, and thus, they can be difficult to be made into nanoparticles using the precipitation method. With regard to the collapse and stability and performance of the chromophoric polymers, there are two additional considerations besides simply the density of the hydrophilic functional groups mentioned above. The first consideration is that the presence of a high density of either hydrophilic functional groups or hydrophilic side chains or hydrophilic moieties will adversely affect the collapse and stability of the formed nanoparticles. The second consideration is more subtle and it deals with the distribution of hydrophilic functional groups. Here, for the same number of hydrophilic functional groups, when it comes to the collapse and stability and performance of the chromophoric polymer dots, it would be much better to have these functional groups concentrated and localized to a small number of monomers rather than have the functional groups distributed homogeneously or more evenly among the monomers. This invention teaches the importance of these design considerations in forming stable and compact chromophoric polymer dots.

The other challenge for controlled chemical functionalization is to develop chromophoric polymer dot with pre-defined number of functional groups. Due to the presence of multiple reactive sites on a nanoparticle surface, it is extremely difficult to control the number and geometrical distribution of chemical functional groups. Nanoparticle multivalance can cause cross-linking of surface proteins that may activate signal pathways and dramatically reduce receptor binding capability. (Howarth, M.; Liu, W.; Puthenveetill, S.; Zheng, Y.; Marshall1, L.; Schmidt, M.; Wittrup, K.; Bawendi, M.; Ting, A. Nat. Methods, 2008, 5, 397.) Therefore, there remains a need to develop fluorescent polymer dots with pre-defined (e.g. mono or bi valent) number of functional groups that allow for further conjugation to biomolecule in a defined (e.g. one-to-one) stoichiometry. Chromophoric polymer dots with pre-defined number (e.g. mono and bi valent) of functional groups bring forward unique properties of highly fluorescent nanoparticle bioconjugates for a wide range of fluorescence-based applications.

BRIEF SUMMARY OF THE INVENTION

In one aspect, the present invention provides an approach to overcome this limitation by using chromophoric polymers with a low density of hydrophilic functional groups and moieties on side chains so the presence of the hydrophilic functional groups and moieties do not interfere with the chain collapse to form a compact and stable nanoparticle that offers good performance. In some embodiments, functionalization of side chains can be avoided altogether, and hydrophilic functional groups can be introduced only to the terminal group or groups of the main polymer chain. In other embodiments, hydrophobic functional groups can be employed that do not affect the collapse and stability of the chromophoric polymer dot, then the hydrophobic functional groups can be converted (i.e., post functionalized) on the surface of the nanoparticles to hydrophilic functional groups for bioconjugation or directly link the hydrophobic functional groups to biomolecules. This latter approach may work particularly well using functional groups that are hydrophobic and clickable (i.e. chemical reactions that fall within the framework of click chemistry), including but not limited to alkyne, strained alkyne, azide, diene, alkene, cyclooctyne, and phosphine groups. While not limiting, the present invention is based in-part on discovering conditions for chain collapse and design considerations mentioned above in forming compact and stable chromophoric polymer dots that offer superior performance. For example, the present invention provides compositions of chromophoric polymers containing functional group or groups that avoid formation and use of their polyelectrolyte-like form to generate chromophoric polymer dots for attaching biological molecules. It is important to note that controlled degree of functionalization (e.g. of side chains) of the polymer sometimes has more important implications on the stability, internal structure, fluorescence brightness, nonspecific labeling of the formed chromophoric polymer dots than just the size of the polymer dots. The present invention also provides various methods to accomplish the creation of chromophoric polymers with low number of functional groups and hydrophilic moieties that do not adversely affect their formation into stable chromophoric polymer dots with good performance characteristics.

In addition to describing compositions and methods to form chromophoric polymers dots that contain functional groups with well controlled density so that they have good stability, compact structure, high fluorescence brightness, and minimum nonspecific labeling, the present invention can include compositions and methods to form such chromophoric polymer dots with a controlled and pre-defined (e.g. monovalent or bivalent) number of functional groups.

One aspect of the present invention relates to functionalized chromophoric polymer dots, where the hydrophilic functional groups are present on the polymer side chains at a sufficiently low density so as not to adversely affect nanoparticle formation and stability and performance. In some embodiments, two aspects can be used to describe the stability of nanoparticles: one is that the nanoparticles are stable against aggregation (i. e. forming large particles); the other is that the nanoparticles are stable against dissociation (i. e. producing small molecules/particles by decomposition). This present invention is based in based in-part on discovering the importance of low density of functionalization (e.g., involving hydrophilic groups) in forming stable and compact chromophoric polymer dots against aggregation or dissociation. For example, hydrophilic functional groups are provided on the side chains of the polymer at sufficiently low density to allow for proper nanoparticle folding and stability. In some embodiments, hydrophobic functional groups (e.g. those used for click chemistry, including but not limited to alkyne, strained alkyne, azide, diene, alkene, cyclooctyne, and phosphine groups) can be used to avoid adversely affecting the formation of stable chromophoric polymer dots. In certain embodiments, the hydrophobic functional groups can be either converted (e.g., post-functionalized) to hydrophilic functional groups or directly linked to biologically relevant molecules. These chromophoric polymer dots can be formed by a variety of methods, such as by using precipitation, although other methods (e.g. emulsion based) can be used as well.

One aspect of the present invention relates to functionalized chromophoric polymer dots, where the functional groups are present only on the terminal groups of the main chain rather than on the side chains of the polymer. Advantageously, the presence of functional groups at only the terminus of the polymer does not adversely affect nanoparticle formation and stability and performance. Preferably, these chromophoric polymer dots can be formed using precipitation, although other methods (e.g. emulsion based) can be used as well.

One aspect of the present invention relates to functionalized chromophoric polymer dots, where the functional groups are present on the terminal groups of the main chain and also on the side chains of the polymer in sufficiently low density so as not to adversely affect nanoparticle formation and stability and performance. In some embodiments, these chromophoric polymer dots can be formed using precipitation, although other methods (e.g. emulsion based) can be used as well.

One aspect of the present invention relates to a rationally functionalized chromophoric polymer dot with a pre-defined number of functional groups attached to the surface of the nanoparticle. In one embodiment, the rationally functionalized chromophoric polymer dot has a single group attached to the surface of the nanoparticle. In other embodiments, the rationally functionalized chromophoric polymer dot has 2, 3, 4, 5, 6, 7, 8, 9, 10, or more functional groups attached to the surface of the nanoparticle.

One aspect of the present invention relates to a monovalent chromophoric polymer dot. The monovalent chromophoric polymer dot comprising a chromophoric polymer dot that bears only one functional group (an exemplary schematic diagram is shown in FIG. 1A).

In another aspect a bioconjugate of a chromophoric polymer dot is provided. The bioconjugate can be formed by the attachment of a biomolecule to a functional group of the chromophoric polymer dot. The attachment may be direct or indirect, as in the exemplary schematic diagram shown in FIG. 1B. In one embodiment, bioconjugates of rationally functionalized chromophoric nanoparticles are provided. For example, a nanoparticle having 1, 2, 3, 4, 5, 6, 7, 8, 9, 10, or more functional groups on the surface of the particle. In a preferred embodiment, the nanoparticle is a monovalent chromophoric nanoparticle. In a second preferred embodiment, the nanoparticle is a bivalent chromophoric nanoparticle.

One aspect of the present invention relates to bivalent chromophoric polymer dot. The bivalent chromophoric polymer dot includes a chromophoric polymer dot that bears only two functional groups, which may be of different type or the same type.

In another aspect a bioconjugate of the bivalent polymer dot is provided. In one embodiment the bioconjugate is formed by the attachment of two biomolecules to the functional groups of the chromophoric polymer dot, i.e., one biomolecule to each of the functional groups of the nanoparticle. The attachment may be direct or indirect. The two biomolecules attached to the two functional groups may be of different type (e.g. two antibodies that are against two different epitopes) or of the same type.

In yet another aspect, the present invention provides single-chain chromophoric nanoparticles. In certain embodiments, the single-chain chromophoric nanoparticles are rationally functionalized with a pre-determined number of functional groups present on the surface of the particle. In a preferred embodiment, the single-chain chromophoric nanoparticles are monovalent. In another preferred embodiment, the single-chain chromophoric nanoparticles are bivalent. In yet other embodiments, the single-chain chromophoric nanoparticles are conjugated to one or more biomolecules.

In yet another embodiment a method of preparing monovalent chromophoric polymer dots is disclosed. In one embodiment, the method involves the attachment of functionalized chromophoric dots to an engineered surface, followed by solvent washing or passivation, and then cleavage from the surface. In one embodiment, the method provides a single-chain monovalent chromophoric nanoparticle. In another embodiment, the method allows for the generation of multi-chain monovalent chromophoric nanoparticles.

BRIEF DESCRIPTION OF THE DRAWINGS

FIGS. 9A-I shows the TEM images and dynamic light scattering (DLS) data of chromophoric polymer dots with different density of side-chain functional groups: (A) TEM of PFBT-C2 dots; (B) TEM of PFBT-C14 dots; (C) TEM of PFBT-C50 dots; (D) DLS of PFBT-C2 dots; (E) DLS of PFBT-C14 dots; (F) DLS of PFBT-C50 dots; (G) DLS of TPP-doped PFBT-C2 dots; (H) DLS of TPP-doped PFBT-C14 dots; (I) DLS of TPP-doped PFBT-C50 dots, in accordance with embodiment of the present invention.

PFBT-C2, (E) PFBT-C14, and (F) PFBT-C50 Pdots, respectively, in accordance with some embodiments of the present invention.

FIGS. 12A-F shows spectroscopic data in dye-doped PFBT dots with different functionalization density. The left panel shows the absorption spectra of PFBT-C2 (solid curves), PFBT-C14 (dash curves), and PFBT-C50 (dotted curves) aqueous nanoparticle solution before (A) and after (B) centrifugal filtration, and the filtrate (C) of the PFBT-C2, PFBT-C14, and PFBT-C50 aqueous solutions. The right panel shows the fluorescence spectra of PFBT-C2 (solid curves), PFBT-C14 (dashed curves), and PFBT-C50 (dotted curves) aqueous nanoparticle solutions before (D) and after (E) centrifugal filtration, and the filtrate (F) of the PFBT-C2, PFBT-C14, and PFBT-C50 aqueous solutions. The insert shows the fluorescence spectra obtained under the excitation wavelength of 450 nm for the filtrate of PFBT-C2, PFBT-C14, and PFBT-C50 aqueous solutions.

FIGS. 13A-D shows the flow cytometry intensity distributions of cancer cells labeled via non-specific binding, with using blank samples (A), PFBT-C2 Pdots (B), PFBT-C14 Pdots (D), and PFBT-C50 Pdots (D).

Figure 14A:
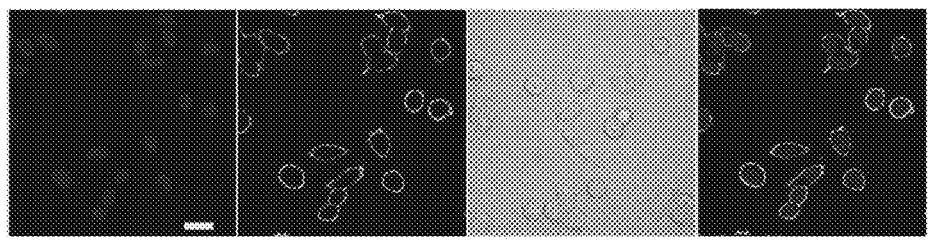
Figure 14B:
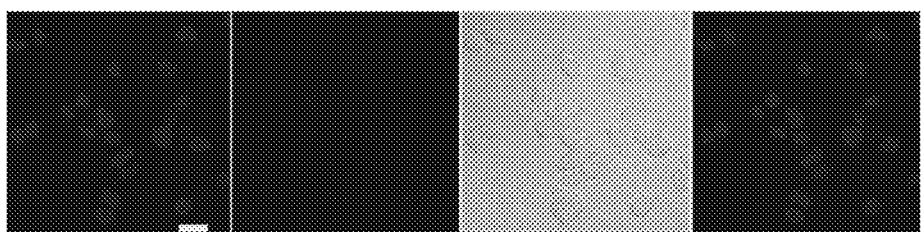
Figure 14C:
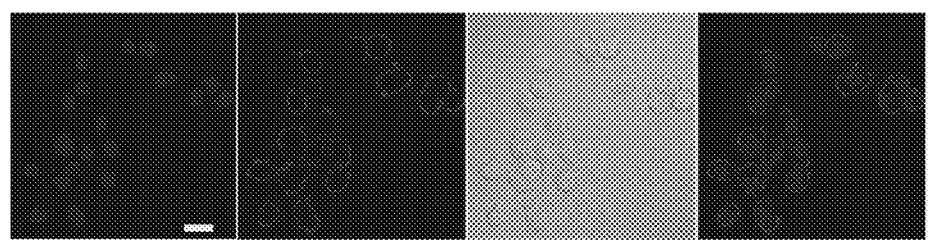

FIGS. 14A-C show fluorescence images of SK-BR-3 breast cancer cells labeled with Pdot-streptavidin probes, in accordance with an embodiment of the present invention. FIG. 14 (A) shows positive labeling using PFBT-C2-SA probe, and (B) shows negative labeling carried out under the same condition as (A) but in the absence of EDC catalyst in the bioconjugation step. FIG. 14 (C) shows positive labeling using red-emitting PFTBT/PFBT-C2-SA probe. Images from the left column to right column are as follows: blue fluorescence from the nuclear stain Hoechst 34580; green or red fluorescence images from Pdots-SA probes; Nomarski (DIC) images, and combined DIC and fluorescence images. Scale bars: 20 m.

Figure 15A:
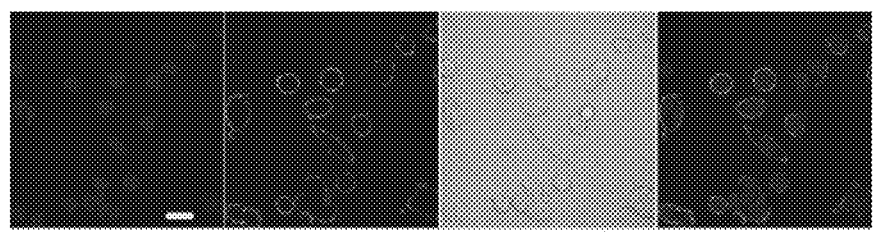
Figure 15B:
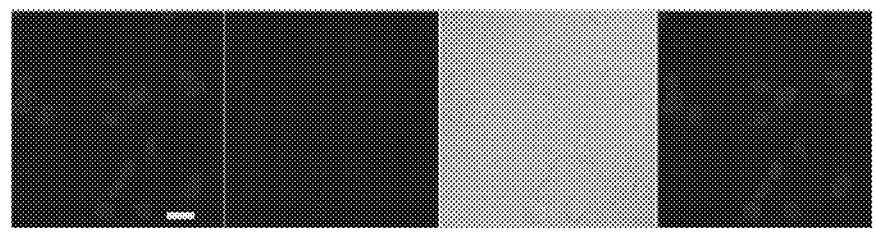

FIGS. 15A and B show fluorescence images of newly synthesized proteins in MCF-7 human breast cancer cells tagged with PFBT-C14A probes, in accordance with an embodiment of the present invention. FIG. 15(A) shows positive labeling using PFBT-C14A probe, and FIG. 15(B) shows negative labeling carried out under the same condition but in the absence of Cu(I) catalyst. Images from left to right are as follows: blue fluorescence from the nuclear stain Hoechst 34580; green fluorescence images from PFBT-C14A probes; Nomarski (DIC), and combined DIC and fluorescence images. Scale bars: 20 m.

Figure 16:
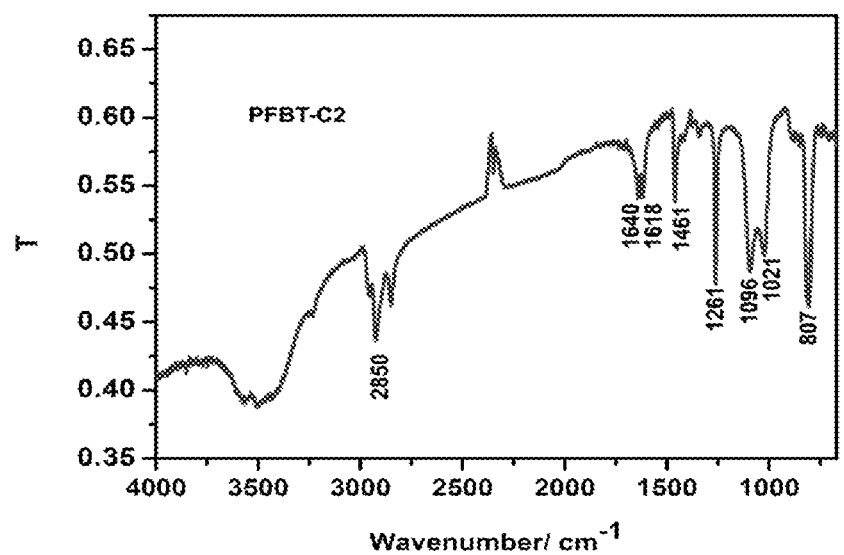

FIG. 16 shows an IR spectrum of PFBT-C2 polymer, in accordance with an embodiment of the present invention.

Figure 17:
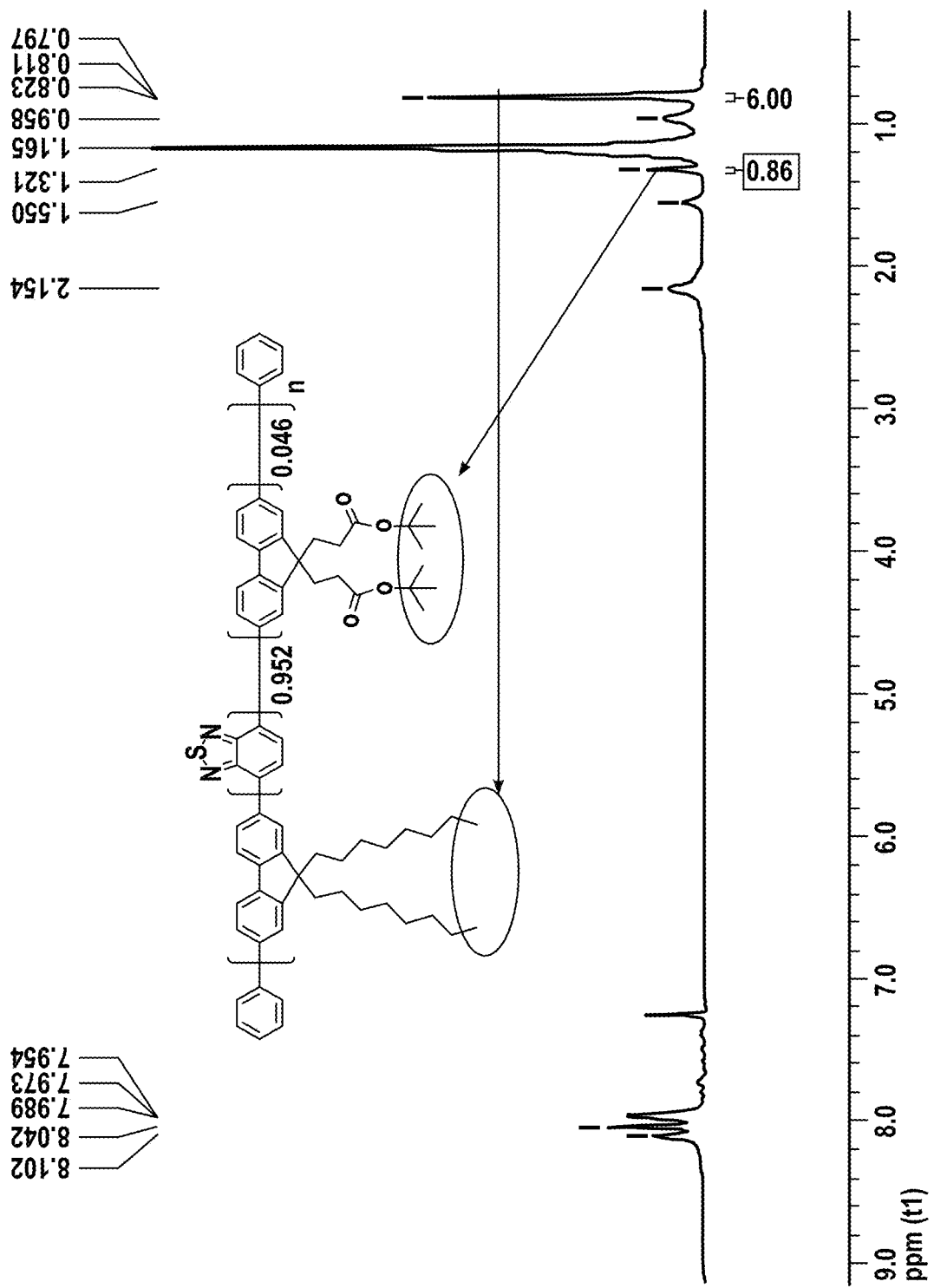

FIG. 17 shows $^1$HNMR of PFBT polymer functionalized with 2.3% bis(3-(tert-butyl propanoate))fluorene monomers, in accordance with an embodiment of the present invention.

Figure 18:
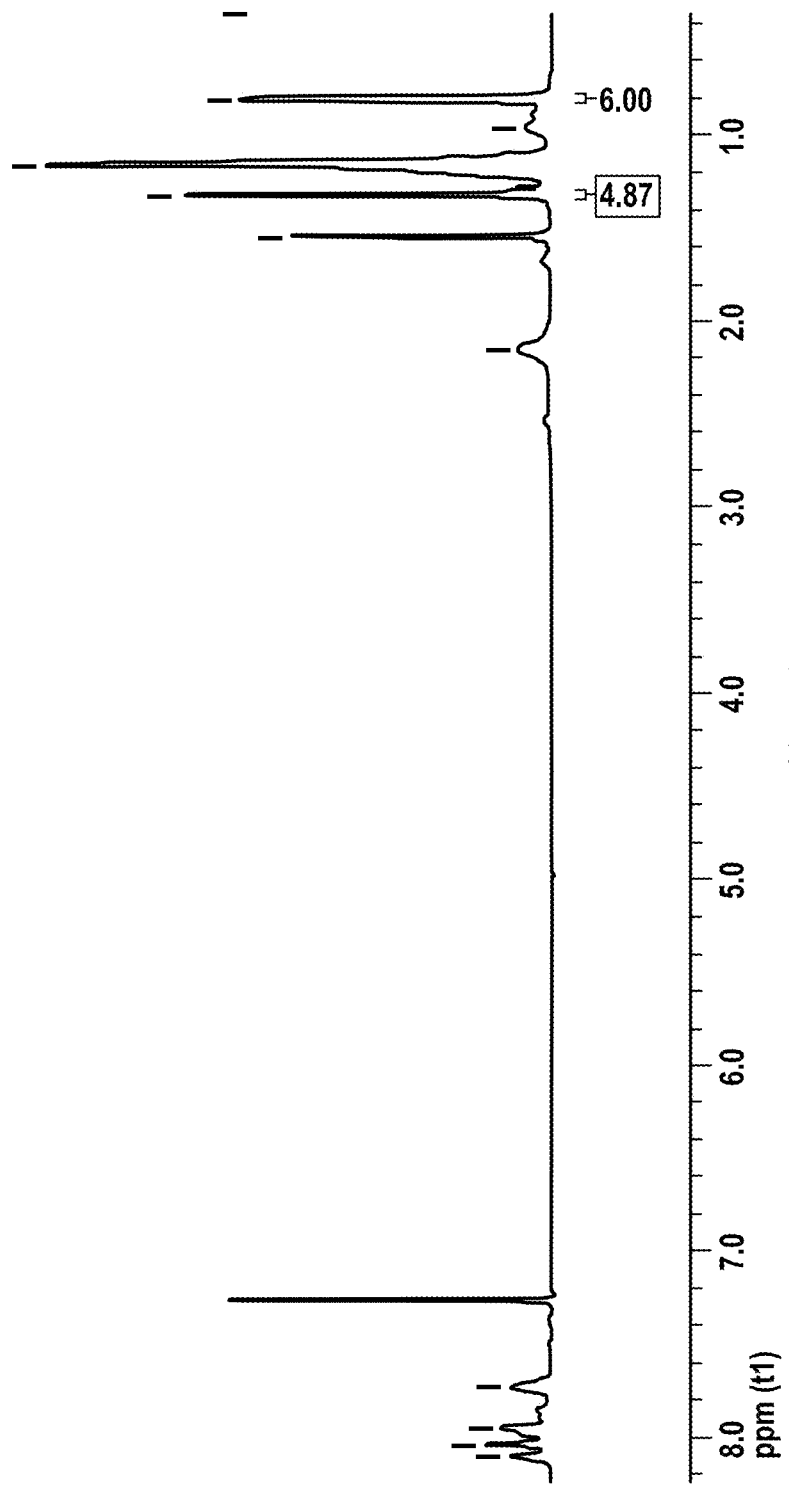

FIG. 18 shows $^1$HNMR of PFBT polymer functionalized with 14% bis(3-(tert-butyl propanoate))fluorene monomers, in accordance with an embodiment of the present invention.

Figure 19:
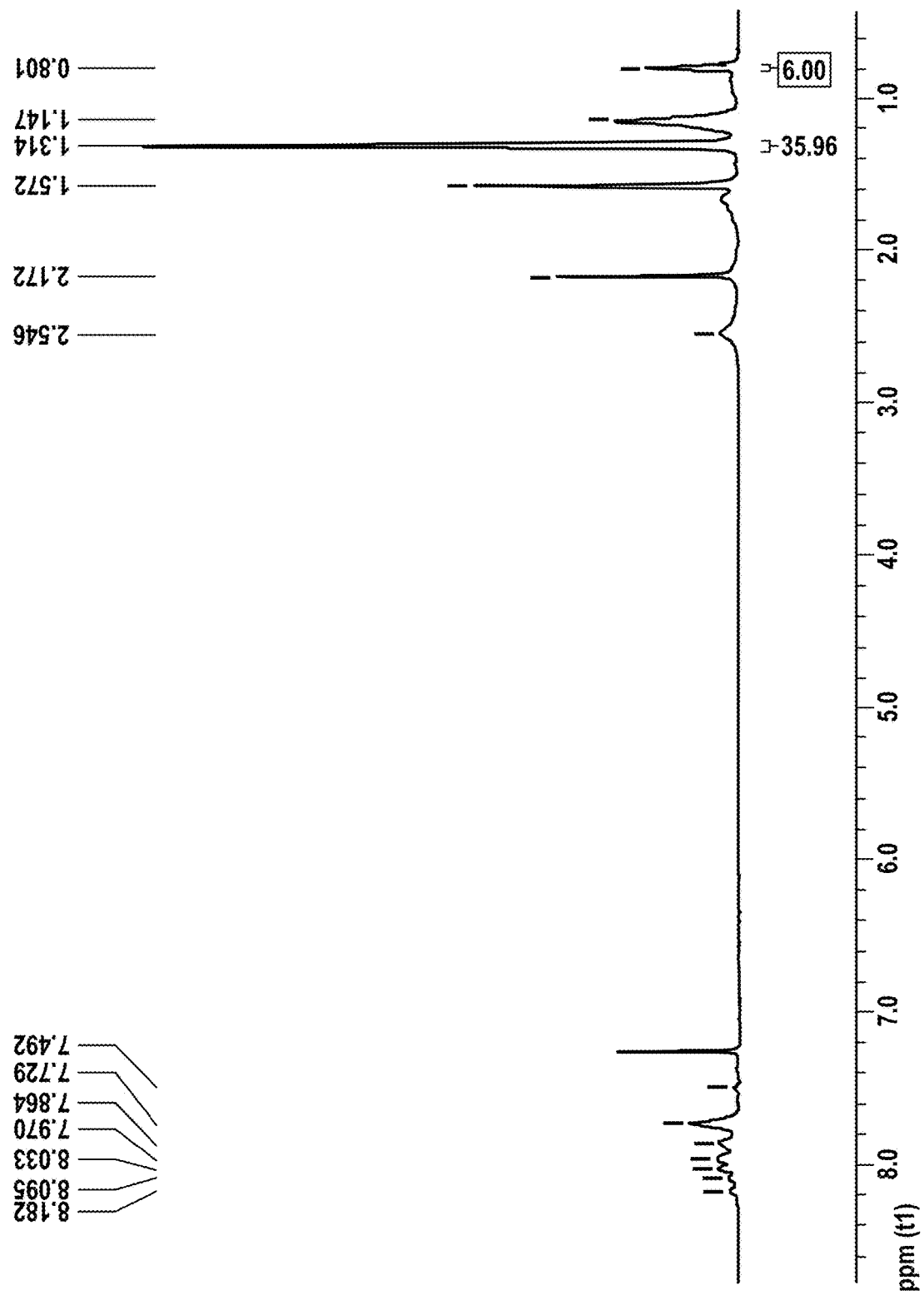

FIG. 19 shows $^1$HNMR of PFBT polymer functionalized with 50% bis(3-(tert-butyl propanoate))fluorene monomers, in accordance with an embodiment of the present invention.

FIGS. 20A-E show a schematic diagram for preparing monovalent chromophoric polymer dots via an engineered particle surface, in accordance with an embodiment of the present invention. In this scheme, polymer dots are attached to silica surface via click chemistry and then they are cleaved from silica beads after passivation or solvent washing. FIG. 20F shows a TEM image of the nanoparticles obtained from step E.

Figure 21:
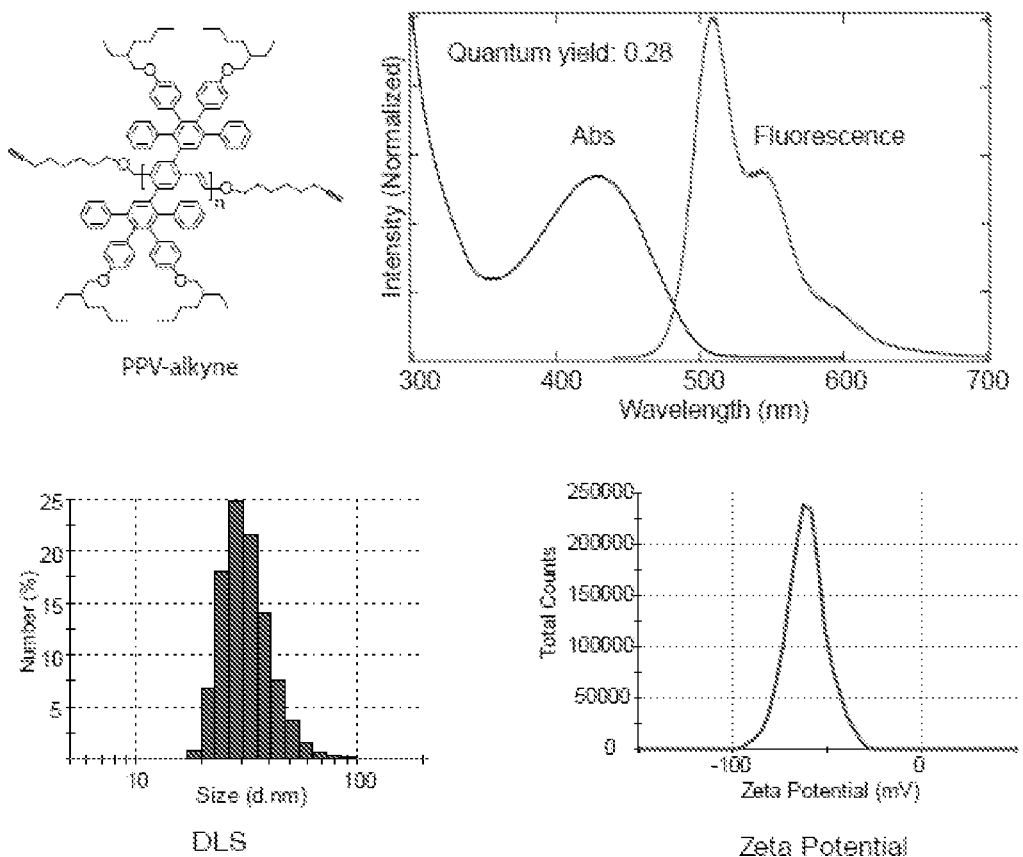

FIG. 21 shows the chemical structure, fluorescence spectra, particle size distribution (DLS) and zeta potential measurement of chromophoric polymer dots functionalized with hydrophobic functional groups, in accordance with an embodiment of the present invention. The PPV derivative was functionalized with alkyne groups that are suitable for bioconjugation. The hydrophobic functional groups can be in the terminating units, and can also be in the side-chains. In some embodiments, because alkyne groups do not adversely affect the polymer dot stability and performance, the functionalization density of alkyne groups can, e.g., vary from 0 to 100%.

DETAILED DESCRIPTION OF THE INVENTION

Embodiments of the present invention relate to a novel class of fluorescent probe, referred as functionalized chromophoric polymer dots or chromophoric polymer dots with controlled number of functional groups, and their biomolecular conjugates for a variety of applications, including but not limited to flow cytometry, fluorescence activated sorting, immunofluorescence, immunohistochemistry, fluorescence multiplexing, single molecule imaging, single particle tracking, protein folding, protein rotational dynamics, DNA and gene analysis, protein analysis, metabolite analysis, lipid analysis, FRET based sensors, high throughput screening, cellular imaging, in vivo imaging, bioorthogonal labeling, click reactions, fluorescence-based biological assays such as immunoassays and enzyme-based assays, and a variety of fluorescence techniques in biological assays and measurements.

While not limited to any particular theory or concept, the present invention is based at least in-part on the concept that nanoparticle formation from a chromophoric polymer is driven in large part by intramolecular and/or intermolecular polymer interactions. For example, polymer dots can be formed due to intramolecular and/or intermolecular hydrophobic interactions that cause a single polymer molecule or several polymer molecules to form a compact polymer dot. In some instances, hydrophilic groups on a polymer, such as those on side chains, can interfere with nanoparticle stability and photophysical performance and cellular targeting. For example, the density and/or positioning of functional groups along the polymer can adversely affect the formation and stability and performance of the polymer dots. As described further herein, the present invention provides embodiments of polymer dots that are functionalized so as to provide optimal nanoparticle packing and internal structure, high fluorescence brightness, and low nonspecific binding of the polymer dots in biological applications. Furthermore, the present invention provides compositions and methods for allowing bioconjugation to polymer dots while also maintaining nanoparticle stability and performance. These aspects, for example, relate to the location and/or density of functional groups in the chromophoric polymer, which can be dependent on the hydrophilicity/hydrophobicity of the functional groups.

Additional advantages and features of the invention will be set forth in part in the description which follows, and in part will be obvious from the description, or can be learned by practice of the invention.

Definitions

As used herein, the term "chromophoric nanoparticle" or "chromophoric polymer dot" refers to a structure comprising one or more polymers (e.g., chromophoric polymers) that have been collapsed into a stable sub-micron sized particle.

"Polymer dot" and "Pdot" can be used interchangeably to represent "chromophoric nanoparticle" or "chromophoric polymer dot". The chromophoric polymer dots provided herein may be formed by any method known in the art for collapsing polymers, including without limitation, methods relying on precipitation, methods relying on the formation of emulsions (e.g. mini or micro emulsion), and methods relying on condensation. In a preferred embodiment, a chromophoric nanoparticle is formed by nanoprecipitation.

Figure 3:
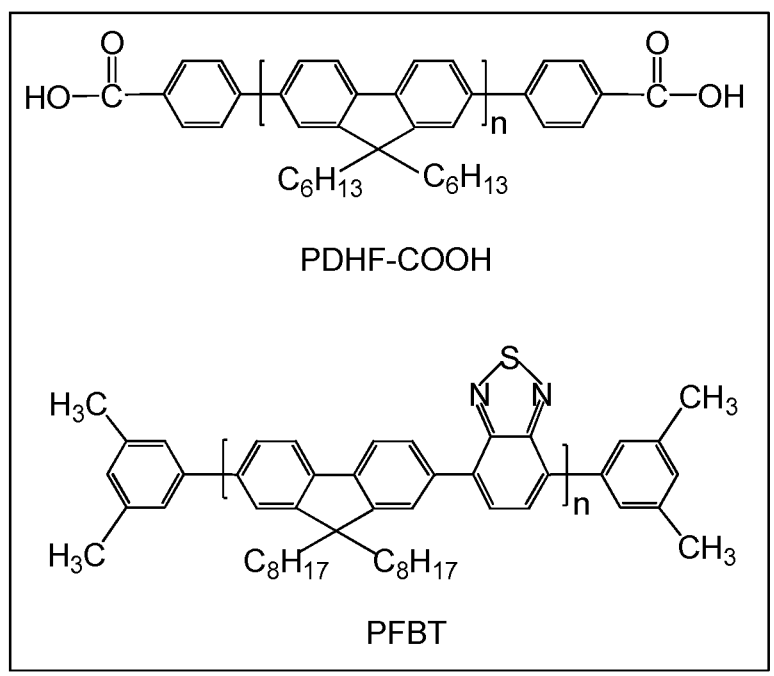
FIG. 3 shows chemical structures of two typical chromophoric polymers: polyfluorene with carboxyl functional groups (PDHF—COOH) and polyfluorene-benzothiadiazole without functional groups (PFBT), in accordance with an embodiment of the present invention.
Figure 7:
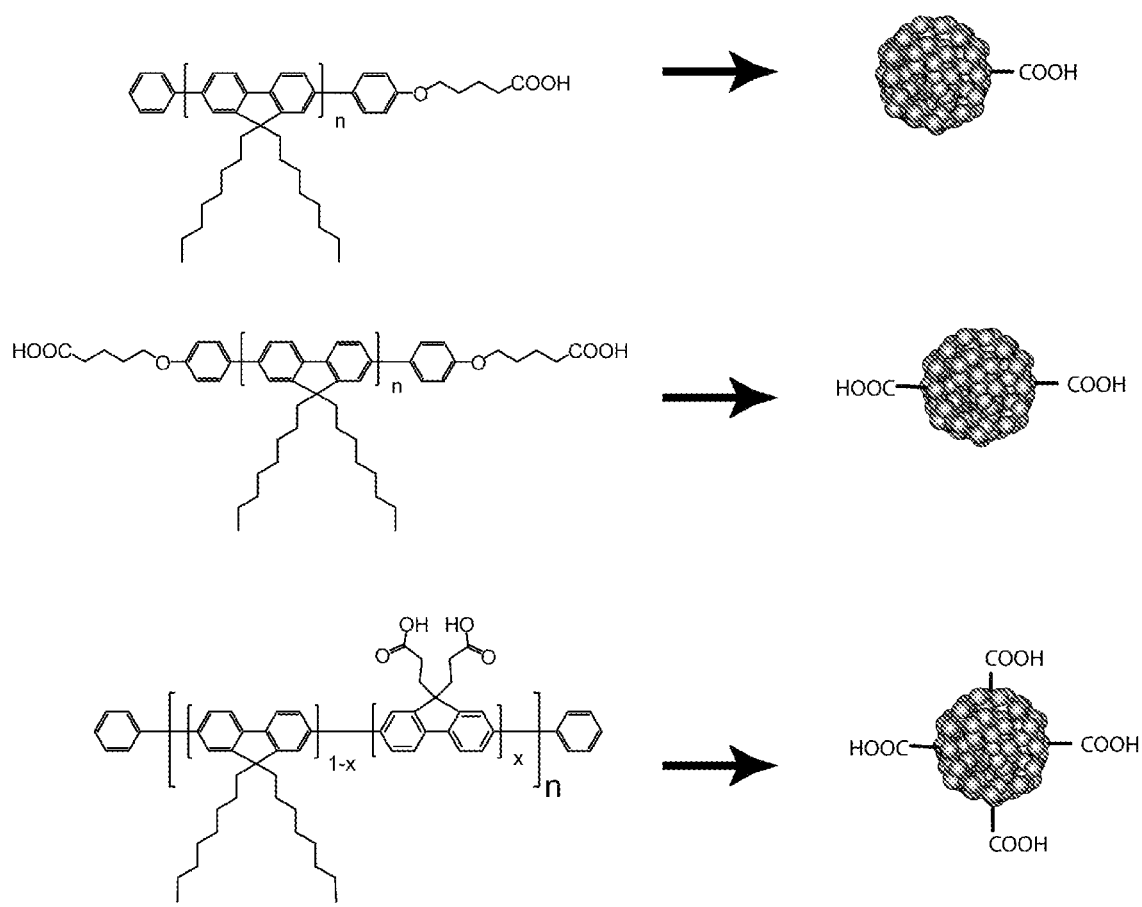
FIG. 7 shows examples of functionalized chromophoric polymer dots where the degree of functionalization is controlled such that the presence of hydrophilic functional groups do not adversely affect the formation and stability and performance of the formed polymer dots, in accordance with embodiments of the present invention.
Figure 8:
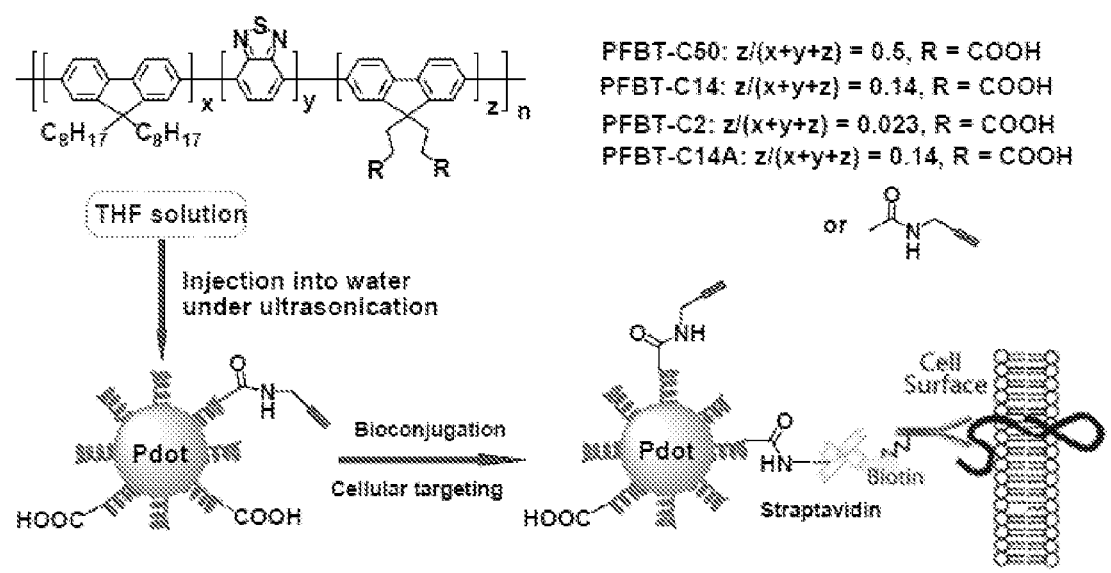
FIG. 8 shows the schematic illustration of low-density side-chain functionalization of chromophoric polymer and bioconjugation of polymer dots for specific cellular targeting, in accordance with embodiments of the present invention.

As used herein, "polymer" is a molecule composed of at least 2 repeating structural units typically connected by covalent chemical bonds. The repeating structural unit may be one type of monomer, and the resulting polymer is a homopolymer. In some embodiments, the polymers can include two different types of monomers, or three different types of monomers, or more types of monomers. One of ordinary skill in the art will appreciate that the different types of monomers can be distributed along a polymer chain in a variety of ways. For example, three different types of monomers can be randomly distributed along the polymer. It will similarly be appreciated that the distribution of monomers along the polymer can be represented in different ways. FIGS. 3, 7 and 8 show some example ways of describing the polymers. The number of repeating structural units (e.g., monomers) along the length of a polymer can be represented by "n." In some embodiments, n can range, e.g., from at least 2, from at least 100, from at least 500, from at least 1000, from at least 5000, or from at least 10,000, or from at least 100,000, or higher. In certain embodiments, n can range from 2 to 10000, from 20 to 10000, from 20 to 500, from 50 to 300, from 100 to 1000, or from 500 to 5000.

Polymers generally have extended molecular structures comprising backbones that optionally contain pendant side groups. The polymers provided herein can include, but are not limited to, linear polymers and branched polymers such as star polymers, comb polymers, brush polymers, ladders, and dendrimers. As described further herein, the polymers can include semiconducting polymers generally well known in the art. In certain embodiments, the polymers (e.g., semiconducting polymers) of the present invention include polymers that do not have triple bonds present along the polymer backbone, i.e., some polymers of the present invention are polymers having a backbone consisting of single bonds, double bonds, or a combination thereof. In some embodiments, monomers along the polymer backbone will be connected by only single or double bonds (e.g., carbon bonds). The structural characteristics (e.g., rigidity) of the polymers can affect whether the polymer folds into a compact nanoparticle. For example, polymers that include repeating units of triple bonds may be more rigid than those that include single and/or double bonds along the backbone. In certain instances, this can lead to complex packing and phase behavior in the nanoparticles, resulting in broadened emission spectra. (Wu, C.; Bull B.; Szymanski, C.; Christensen, K.; McNeill, J. ACS Nano 2008, 2, 2415-2423.)

As used herein, the term "chromophoric polymer" is a polymer in which at least a portion of the polymer comprises chromophoric units. The term "chromophore" is given its ordinary meaning in the art. A chromophore absorbs certain wavelength of light from UV to near infrared region, and may be or may not be emissive.

A "chromophoric unit" in this invention includes, but is not limited to, a unit of structures with delocalized pi-electrons, a unit of small organic dye molecules, and/or a unit of metal complexes. Examples of chromophoric polymers can include polymers comprising units of structures with delocalized pi-electrons such as semiconducting polymers, polymers comprising units of small organic dye molecules, polymers comprising units of metal complexes, and polymers comprising units of any combinations thereof.

As used herein the term "functional group" refers to any chemical unit that can be attached, such as by any stable physical or chemical association, to the chromophoric polymer, thereby rendering the surface of the chromophoric polymer dot available for conjugation. A functional group is also referred to herein as a reactive functional group.

As used herein, the term "hydrophilic moiety" refers to a chemical unit that increases the hydrophilicity of a polymer. In some embodiments, hydrophilic moieties can include hydrophilic functional groups. In certain embodiments, hydrophilic moieties can include non-reactive hydrophilic moieties, which are distinct from hydrophilic functional groups. For example, non-reactive hydrophilic moieties can include nonionic, non-reactive hydrophilic moieties, such as water soluble polymers (e.g., polyethylene glycol (PEG)). Non-reactive hydrophilic moieties can also include ionic, non-reactive hydrophilic moieties, such as positive ionic species, negative ionic species, and zwitterionic species, or combinations thereof.

As used herein the term "hydrophilic functional group" refers either to a functional group that is hydrophilic in nature or to a hydrophobic functional group that is attached to a hydrophilic side chain or hydrophilic moiety, which renders the hydrophobic functional group more hydrophilic in nature and which facilitate the arrangement of the hydrophobic functional groups on the chromophoric polymer dot particle surface rather than getting buried inside the hydrophobic core of the chromophoric polymer dot. Examples of hydrophobic functional groups that can be rendered more hydrophilic by attachment to hydrophilic side chains or moieties include but not limited to alkyne, strained alkyne, azide, diene, alkene, cyclooctyne, and phosphine groups (for click chemistry) attached to a hydrophilic side chain such as PEG (polyethylene glycol) or to any other hydrophilic side chains. As described herein, a hydrophobic functional group that is attached to a hydrophilic side chain or hydrophilic moiety is attached to the polymer before particle formation, i.e., pre-functionalized. In some embodiments, a hydrophobic functional group that is attached to a hydrophilic side chain or hydrophilic moiety can be suitable for bioconjugation.

In certain embodiments, a functional group can include a hydrophilic functional group that is hydrophilic in nature and is attached to the polymer (e.g., on the side chain). In some embodiments, hydrophilic functional groups can include, carboxylic acid or salts thereof, amino, mercapto, azido, aldehyde, ester, hydroxyl, carbonyl, sulfate, sulfonate, phosphate, cyanate, succinimidyl ester, substituted derivatives thereof. In certain embodiments, hydrophilic functional groups can include carboxylic acid or salts thereof, amino, mercapto, azido, aldehyde, ester, hydroxyl, carbonyl, sulfate, phosphate, cyanate, succinimidyl ester, and substituted derivatives thereof. In certain embodiments, the hydrophilic functional groups can be suitable for bioconjugation. In some embodiments, the hydrophilic functional groups can be suitable for bioconjugation and also stable in aqueous solution (e.g., the groups do not hydrolyze). Such functional groups can be found by one of ordinary skill in the art, for example in Bioconjugate Techniques (Academic Press, New York, 1996 or later versions) the content of which is herein incorporated by reference in its entirety for all purposes. Some hydrophilic functional groups suitable for bioconjugation include carboxylic acid or salts thereof, amino, mercapto, azido, aldehyde, ester, hydroxyl, carbonyl, phosphate, cyanate, succinimidyl ester, and substituted derivatives thereof. In some embodiments, hydrophilic functional groups suitable for conjugation can include carboxylic acid or salts thereof, amino groups, mercapto, succinimidyl ester, and hydroxyl. A non-limiting list of hydrophilic functional group pairs is provided in Table 1.

TABLE 1

Exemplary Hydrophilic Functional Group Pairs for Conjugation Chemistry

| Functional Groups: | Reacts with: |
|---|---|
| Ketone and aldehyde groups | Amino, hydrazido and aminooxy |
| Imide | Amino, hydrazido and aminooxy |
| Cyano | Hydroxy |
| Alkylating agents (such as haloalkyl groups and maleimido derivatives) | Thiol, amino, hydrazido, aminooxy |
| Carboxyl groups (including activated carboxyl groups) | Amino, hydroxyl, hydrazido, aminooxy |

In some embodiments, a functional group can include a hydrophobic functional group that are attached to a hydrophobic polymer (e.g., on a hydrophobic side chain). In some embodiments, hydrophobic functional groups can generally include, but are not limited to, alkynes, alkenes, and substituted alkyl derivatives that are suitable for conjugation. The present invention provides polymers that include hydrophobic functional groups for compact nanoparticle formation (e.g., pre-functionalization). After formation, some of the hydrophobic functional groups can be chemically modified to form hydrophilic functional groups used for bioconjugation (e.g., post-functionalization). In certain embodiments, hydrophobic functional groups attached to a hydrophobic polymer can be suitable for bioconjugation. For example, the hydrophobic functional groups can include but are not limited to those used for click chemistry, such as alkyne, strained alkyne, azide, diene, alkene, cyclooctyne, and phosphine groups. These hydrophobic functional groups can, e.g., be used for bioconjugation reactions that covalently couple the polymer dots to a biologically relevant molecule (e.g., an antibody).

The functional groups can be attached to the chromophoric polymer dots in a variety of ways. For example, the polymers can be chemically modified to include functional groups prior to particle formation, described herein as "pre-functionalization." Pre-functionalization includes embodiments in which the monomers include the functional groups prior to formation of the polymers, as well as reacting an already formed polymer to include functional groups along the backbone of monomers. Alternatively, a chromophoric polymer dot can be modified after particle formation to attach a functional group, e.g., on the surface of the polymer dot, described herein as "post-functionalization." One of ordinary skill in the art will appreciate that pre- and post-functionalization can be carried out in a variety of orders to form a functionalized polymer.

For example, a polymer can be pre-functionalized with functional groups, e.g., hydrophobic functional groups. The hydrophobic pre-functionalized polymer can be condensed into a nanoparticle, and then post-functionalized with a functional group, e.g., a hydrophilic functional group suitable for bioconjugation. Alternatively, both pre- and post-functionalization steps can include functionalization with hydrophilic groups or hydrophobic groups.

As described herein, some of the functional groups can be "suitable for bioconjugation," which is referred as to a functional group that is covalently bonded to a biomolecule, such as an antibody, protein, nucleic acid, streptavidin, or other molecule of biological relevance. Such functional groups can be found by one of ordinary skill in the art, for example in Bioconjugate Techniques (Academic Press, New York, 1996 or later versions) the content of which is herein incorporated by reference in its entirety for all purposes. In some embodiments, functional groups suitable for bioconjugation can include functional groups that can be conjugated to a biomolecule under a variety of conditions, such as, e.g., in polar or non-polar solvents. In certain embodiments, functional groups suitable for bioconjugation can include functional groups that can be conjugated to a biomolecule in an aqueous solution. In some embodiments, functional groups suitable for bioconjugation can include functional groups that can be conjugated to a biomolecule in an aqueous solution in which the biomolecule retains its biological activity (e.g., monoclonal binding specificity for an antibody). In certain embodiments, functional groups suitable for bioconjugation can include functional groups that are covalently bonded to a biomolecule. For example, typical covalent bonding attachments of functional groups to biomolecules can include, e.g., a carboxyl functional group reacting with an amine on a biomolecule to form an amide bond, a sulfhydryl functional group reacting with a sulfhydryl group on a biomolecule to form a cysteine bond, or an amino functional group reacting with a carboxyl group on a biomolecule to form an amide bond. In some embodiments, the specific reactions of bioconjugations can include the functional group pairs in Table 1.

As used herein, the term "rationally functionalized" refers to the modification of a chromophoric polymer or nanoparticle by the attachment of a pre-defined number of reactive functional groups. For example, the polymers can be chemically modified to include functional groups prior to particle formation (pre-functionalization). Alternatively, a chromophoric polymer dot can be modified after formation to attach a functional group, e.g., on the surface of the polymer dot (post-functionalization). In one embodiment, a plurality of rationally functionalized nanoparticles will each have a single functional group attached to their surface. In other embodiments, a plurality of functionalized nanoparticles will each have exactly two functional groups attached to their surface. In yet other embodiments, a plurality of functionalized nanoparticles will each have exactly 3, 4, 5, 6, 7, 8, 9, 10, or more functional groups attached to their surface. The rational functionalization of chromophoric polymers and/or nanoparticles may be achieved in various fashions. For example, in one embodiment a pre-defined number of reactive functional groups are attached to a chromophoric polymer, which is then collapsed into a nanoparticle. In a second embodiment, a pre-formed chromophoric nanoparticle, in which the number of reactive functional groups on the surface of the particle has not been pre-defined, may be treated by some methods to form a chromophoric particle with a defined number of functional group. Examples of such methods such as solvent washing or surface passivation are provided herein to render the nanoparticle rationally functionalized.

Nonionic and non-reactive hydrophilic moieties can be added to the polymers to achieve certain characteristics, such as to reduce nonspecific adsorption in biological applications. A variety of polymers, such as polyethylene glycol (PEG), are well known in the art to reduce non-specific absorption. Nonionic hydrophilic moieties can be linked to a chromophoric polymer prior to particle formation (pre-functionalization). Alternatively, nonionic hydrophilic moieties can be linked to a chromophoric polymer dot after nanoparticle formation, e.g., on the surface of the polymer dot (post-functionalization). In some embodiments, non-ionic hydrophilic moieties can be attached via both pre- and post-functionalization. For pre-functionalization, the density of hydrophilic moieties, such as PEG groups in the chromophoric polymer, can affect the formation, stability, internal structure, and fluorescence brightness of the polymer dots. As described further herein, the density of PEG groups should be sufficiently low so that they do not adversely affect the stability and performance of the polymer dots. For post-functionalization, the density of PEG groups on the surface of the chromophoric polymer dot can be high because the nanoparticles are already formed and the PEG groups do not adversely affect the formation, stability, internal structure, and fluorescence brightness of the polymer dots, but can reduce nonspecific interactions.

Ionic and non-reactive hydrophilic moieties can be linked to chromophoric polymers to achieve certain properties for the resulting polymer dots, such as increasing surface zeta potential by highly charged species, and/or yielding zwitterionic surfaces by zwitterionic species. In some embodiments, nonionic hydrophilic moieties can be attached via pre-functionalization, post-functionalization, or a combination of both. For pre-functionalization, the density of ionic hydrophilic moieties in the chromophoric polymer can affect the formation, stability, internal structure, and fluorescence brightness of the polymer dots. Therefore, the density of ionic moieties should be sufficiently low so that they do not adversely affect the stability and performance of the polymer dots. For post-functionalization, the density of ionic moieties on the surface of the chromophoric polymer dot can be high because the nanoparticles are already formed and the ionic moieties do not adversely affect the formation, stability, internal structure, and fluorescence brightness of the polymer dots, but can provide certain properties such as high surface zeta potential and/or zwitterionic surfaces.

In some embodiments, a reactive functional group can be attached to the surface of the nanoparticle via a linker moiety. A variety of linker moieties are generally well known in the art and can be found by one of ordinary skill in the art, for example in Bioconjugate Techniques (Academic Press, New York, 1996 or later versions) the content of which is herein incorporated by reference in its entirety for all purposes. In certain embodiments, the linker moieties can include a water soluble polymer. In some embodiments, the chromophoric polymer dots can also include polymers having non-reactive chemical groups. In certain embodiments, non-reactive chemical groups can also include, e.g., a water soluble polymer. Suitable water soluble polymers for the present invention can include, but are not limited to, polyethylene glycol.

As used herein, the "density" of functional groups and moieties attached to a polymer, for example at one or more side chains or termini of the polymer, refers to the number of monomers with attached functional groups or moieties expressed as a percentage of the monomeric units of the polymer. For example, if half of the monomeric units of a particular polymer have a functional group attached, the density of the functional groups is 50%. In some embodiments, the polymers (e.g., semiconducting polymers) in the chromophoric polymer dots can be designed to include ranges of functional group or moiety densities. In certain embodiments, density of the hydrophobic functional groups on a polymer (e.g., a semiconducting polymer) can be less than about 100%, less than about 90%, less than about 80%, less than about 70%, less than about 60%, less than about 50%, less than about 40%, less than about 30%, less than about 20%, or less than about 10%. In case of pre-functionalization, the density of hydrophilic functional groups and moieties in the chromophoric polymer can affect the formation, stability, internal structure, and fluorescence brightness of the polymer dots. Therefore, the density of hydrophilic functional groups and moieties on a chromophoric polymer should be sufficiently low so that they do not adversely affect the stability and performance of the polymer dots. In some embodiments, density of the hydrophilic functional groups and moieties on a polymer (e.g., a semiconducting polymer) can be less than about 50%, less than about 40%, less than about 30%, less than about 20%, less than about 10%, or less than about 5%. In some embodiments involving post-functionalization, hydrophilic functional groups and moieties can be linked to the surface of a chromophoric dot, in which the density of functionalization can be high (e.g., greater than about 50%) because the nanoparticles are already formed and the hydrophilic moieties do not adversely affect the formation, stability, internal structure, and fluorescence brightness of the polymer dots, but can provide certain properties such as reducing nonspecific interactions by PEG groups, and/or generating high surface zeta potential by highly charged species and/or creating zwitterionic surfaces by zwitterionic moieties. In certain embodiments, the polymers can include both hydrophobic and hydrophilic functional groups at a percentage listed above. In some embodiments, the polymers described herein will include at least 50% hydrophobic functional groups. It will be appreciated by one of ordinary skill in the art that the locations of the side-chain functional groups can be randomly distributed along the length of a polymer. For example, if a polymer has a length n of 100 monomers, then the side chains substituted with functional groups (e.g., carboxyl groups) can be randomly located along the length of the polymer. Some functional groups may be located on immediately adjacent monomers or farther down the polymer, e.g., two or three monomers in one direction. In certain embodiments, the functional groups are functional groups suitable for bioconjugation, as described further herein. Densities can be determined using a variety of spectroscopic techniques, such as nuclear magnetic resonance (NMR).

Chromophoric Polymer Dots

The present invention provides, in one embodiment, functionalized chromophoric polymer dots, where the hydrophilic functional groups are introduced into the side chains of the polymer at a sufficiently low density where the functional groups do not adversely affect the collapse of the polymer chain into a nanoparticle form, and/or do not adversely affect the stability and performance of the formed chromophoric polymer dots, and/or do not adversely loosen the compact internal structure, and/or do not adversely reduce fluorescence brightness, and/or do not adversely increase nonspecific labeling. As provided herein, the degree of hydrophilicity of the functional groups can affect what constitutes a sufficiently low density that gives desired characteristics for the polymer dots. In some embodiments, the density of the functional groups on the side chains is less than about 50%. In some embodiments, the density of the functional groups on the side chains is less than about 40%. In some embodiments, the density of the functional groups on the side chains is less than about 30%. In some embodiments, the density of the functional groups on the side chains is less than about 25%. In another embodiment, the density of the functional groups on the side chains is less than about 20%. In another embodiment, the density of the functional groups on the side chains is less than about 15%. In another embodiment, the density of the functional groups on the side chains is less than about 10%. In yet another embodiment, the density of the functional groups on the side chains is less than about 5%. In certain embodiments, the density of the functional groups on the side chains is less than about 25%, or less than about 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, or less. In certain example embodiments, after nanoparticle formation (post-functionalization), the density of the functional groups on the surface of a chromophoric dot can be increased by surface modifications because the nanoparticles are already formed and the hydrophilic moieties do not adversely affect the formation, stability, internal structure, and fluorescence brightness of the polymer dots. Moreover, the hydrophilic moieties can provide certain properties such as reducing nonspecific interactions by PEG groups, and/or generating high surface zeta potential by highly charged species and/or creating zwitterionic surfaces by zwitterionic moieties.

The present invention provides, in another embodiment, functionalized chromophoric polymer dots, where hydrophilic functional groups are introduced into only the terminal groups of the main chain of the polymer where the functional groups do not adversely affect the collapse of the polymer chain into a nanoparticle form, and/or do not adversely affect the stability of the formed chromophoric polymer dots, and/or do not adversely loosen the compact internal structure, and/or do not adversely reduce fluorescence brightness, and/or do not adversely increase nonspecific labeling. In yet another embodiment, the hydrophilic functional groups are introduced into both the terminal groups of the main chain of the polymer and also the side chains of the polymer but at a sufficiently low density where the functional groups do not adversely affect the collapse of the polymer chain into a nanoparticle form, or do not adversely affect the stability of the formed chromophoric polymer dots, or do not adversely loosen the compact internal structure, or do not adversely reduce fluorescence brightness, or do not adversely increase nonspecific labeling. The degree of hydrophilicity of the functional groups can affect what constitutes a sufficiently low density that gives desired characteristics for the polymer dots. In certain example embodiments, after the nanoparticle formation (post-functionalization), the density of the hydrophilic moieties on the surface of a chromophoric dot can be increased by surface modifications because the nanoparticles are already formed and the hydrophilic moieties do not adversely affect the formation, stability, internal structure, and fluorescence brightness of the polymer dots, but can provide certain properties such as reducing nonspecific interactions by PEG groups, and/or generating high surface zeta potential by highly charged species and/or creating zwitterionic surfaces by zwitterionic moieties.

In some embodiments, this invention provides functionalized chromophoric polymer dots that include hydrophobic functional groups. The hydrophobic functional groups include but not limit to those used for click chemistry, such as alkyne, strained alkyne, azide, diene, alkene, cyclooctyne, and phosphine groups. The density of the hydrophobic functional groups can be varied from 0% to 100%. In certain embodiments, the density of the hydrophobic functional groups can be about 100%, less than about 100%, less than about 90%, less than about 80%, less than about 70%, less than about 60%, less than about 50%, less than about 40%, less than about 30%, less than about 20%, less than about 10%, less than about 5%, less than about 1%, or lower. In some embodiments, the density of functionalizing with hydrophobic functional groups does not adversely affect the collapse of the polymer chain into a nanoparticle form, and/or does not adversely affect the stability of the formed chromophoric polymer dots, and/or does not adversely loosen the compact internal structure, and/or does not adversely reduce fluorescence brightness, and/or does not adversely increase nonspecific labeling. In certain embodiments, the hydrophobic functional groups can be directly linked to biologically relevant molecules described further herein (e.g., antibodies) or be converted to hydrophilic functional groups that can link to biologically relevant molecules or be converted to other hydrophilic moieties for certain properties after the formation of a chromophoric polymer dot.

In another embodiment, the functionalized chromophoric polymer dots can include hydrophobic chromophoric polymers, physically mixed or chemically cross-linked with another one or more chromophoric polymers with hydrophilic functional groups. The hydrophobic chromophoric polymers may not include a hydrophilic functional group, but may have hydrophobic functional groups (e.g. those used for click chemistry, including but not limited to alkyne, strained alkyne, azide, diene, alkene, cyclooctyne, and phosphine groups). In certain embodiments, the surface of the chromophoric polymer dots can be functionalized by one or more chromophoric polymers comprising hydrophilic functional groups, which are introduced into either the terminal groups of the main chain of the polymer or the side chains of the polymer. In these embodiments, the density of the functionalization in the functionalized chromophoric polymer can be varied from 0% to 100%, but the blending ratio of the functionalized chromophoric polymers to the hydrophobic polymers should be sufficiently low so that the functionalization does not adversely affect the collapse of the polymer chain into a nanoparticle form, and/or does not adversely affect the stability of the formed chromophoric polymer dots, and/or does not adversely loosen the compact internal structure, and/or does not adversely reduce fluorescence brightness, and/or does not adversely increase nonspecific labeling.

In some embodiments, the functionalized chromophoric polymer dots comprise one or more functionalized chromophoric polymers that are chemically cross-linked with each other prior to particle formation and also comprise surface functional groups for bioconjugation. In this embodiment, the functional groups can be introduced into either the terminal groups of the main chain of the polymer or the side chains of the polymer. The density of the functionalization in the functionalized chromophoric polymers can be varied from 0% to 100% to form chromophoric polymer dots with chemically cross-linked structure, where the chemical cross-linking, even at high density of functionalization, can assist the collapse of the polymer chain into a nanoparticle form, form compact internal structure, keep good stability and fluorescence brightness of the formed chromophoric polymer dots.

The present invention also provides, in one embodiment, a monovalent chromophoric polymer dot, which comprises a chromophoric polymer dot and only one functional group. The chromophoric polymer dot contains at least one chromophoric polymer. The "monovalent" as that term is used herein refers to just one functional group that is attached to the chromophoric polymer dots. The functional group can be attached to the chromophoric polymer dot by any stable physical association or chemical bonding, and provides only one reactive site on the surface of chromophoric polymer dot for bioconjugation.

The present invention provides, in another embodiment, a bivalent chromophoric polymer dot, which comprises a chromophoric polymer dot and only two functional groups. The chromophoric polymer dot contains at least one chromophoric polymer. The "bivalent" as that term is used herein refers to just two functional groups that are attached to each chromophoric polymer dot. The functional groups can be attached to the chromophoric polymer dot by any stable physical association or chemical bonding, and provides only two reactive sites on the surface of chromophoric polymer dot for bioconjugation. The two reactive sites can have different reactivity (e.g. via two different types of function groups) or same reactivity.

In some embodiments, the chromophoric polymer dots can include at least one semiconducting polymer. In certain embodiments, the chromophoric polymer dots can include luminescent semiconducting polymer with delocalized pi-electrons. The term "semiconducting polymer" is recognized in the art. Typical luminescent semiconducting polymers include, but are not limited to fluorene polymers, phenylene vinylene polymers, phenylene polymers, benzothiazole polymers, thiophene polymers, carbazole fluorene polymers, boron-dipyrromethene polymer and related copolymers. In certain embodiments, the semiconducting polymers of the present invention include polymers that do not have triple bonds present along the polymer backbone. In some embodiments, the chromophoric polymer dots can include a single molecule semiconducting polymer. In certain embodiments, the chromophoric polymer dots can include several molecules of semiconducting polymer. The several molecules can, e.g., be the same type of semiconducting polymer or a blend of different polymers (e.g., semiconducting polymers and/or non-semiconducting polymers). A list of some semiconducting polymers and their abbreviations is provided in Table 2.

TABLE 2

Non-limiting examples of semiconducting polymers

Fluorene Polymers:

Poly(9,9-dihexylfluorenyl-2,7-diyl) (PDHF),
Poly(9,9-dioctylfluorenyl-2,7-diyl) (PFO),
Fluorene based Copolymers:

Poly[{9,9-dioctyl-2,7-divinylene-fluorenylene}-alt-co-{2-methoxy-5-(2-ethylhexyloxy)-1,4-phenylene}] (PFPV),
Poly[(9,9-dioctylfluorenyl-2,7-diyl)-co-(1,4-benzo-{2,1,3}-thiadiazole)] (PFBT),
Poly[(9,9-dioctylfluorenyl-2,7-diyl)-co-(4,7-Di-2-thienyl-2,1,3-benzothiadiazole)] (PFTBT),
Poly[(9,9-dioctylfluorenyl-2,7-diyl)$_{0.9}$-co-(4,7-Di-2-thienyl-2,1,3-benzothiadiazole)$_{0.1}$] (PF-0.1TBT),
Phenylene Vinylene Polymers:

Poly[2-methoxy-5-(2-ethylhexyloxy)-1,4-phenylenevinylene] (MEH-PPV),

In some embodiments, the chromophoric polymer dot comprises polymers bearing units of small organic dye molecules, metal complexes, photochotochromic dye, and any combinations thereof, for example, optically inactive polymers such as polystyrene covalently linked or grafted with small organic dye, metal complexes, photochromic dyes and any combination thereof. These dyes or metal complexes may have sensing functions, such as oxygen sensing capability, ion sensing capability, glucose sensing capability, neurotransmitter sensing capability, drug sensing capability, metabolite sensing capability, protein sensing capability, signaling molecule sensing capability, toxin sensing capability, DNA and RNA sensing capability, and the like.

In some embodiments, the chromophoric polymer dot comprises semiconducting polymers covalently linked with small organic dye molecules, metal complexes, photochromic dye, and any combinations thereof as emissive units. Such emissive units can tune the emission color, increase the quantum yield, and improve the photostability of the chromophoric polymer dot. In a preferable embodiment, the small organic dyes, or metal complexes can have sensing functions, and therefore add additional functionalities to the chromophoric polymer dot, such as oxygen sensing capability, ion sensing capability, glucose sensing capability, neurotransmitter sensing capability, drug sensing capability, metabolite sensing capability, protein sensing capability, signaling molecule sensing capability, toxin sensing capability, DNA and RNA sensing capability, and the like.

In some embodiments, the chromophoric polymer dots may also comprise semiconducting polymer, physically mixed or chemically cross-linked with other chromophoric polymer such as optically inactive polymer covalently linked or grafted with small organic dye, metal complexes, photochromic dyes and any combination thereof, to have additional functionalities such as oxygen sensing capability, ion sensing capability, glucose sensing capability, neurotransmitter sensing capability, drug sensing capability, metabolite sensing capability, protein sensing capability, signaling molecule sensing capability, toxin sensing capability, DNA and RNA sensing capability, and the like.

In some embodiments, the chromophoric polymer dot may also comprise semiconducting polymer, physically mixed or chemically cross-linked with other components including, e.g., fluorescent dye, inorganic luminescent materials, magnetic materials, metal materials, to tune emission color, improve quantum yield and photostability, and have additional functionalities such as magnetic functions, plasmon resonance functions, and the like.

Functionalized Chromophoric Polymers that Form Stable Polymer Dots.

One embodiment of the present invention provides functionalized chromophoric polymers that form stable nanoparticles. As used herein, the term "stable", can refer to chromophoric polymer dots that do not aggregate and/or change substantially in size (as measured by electron microscopy, atomic force microscopy, or dynamic light scattering) when stored in an appropriate aqueous solution for an extended period of time. Aggregation or a change substantially in size of the polymer dots can, for example, be characterized as an increasing number of aggregates including more than one polymer dot. Aggregates can be detected visually by the eye, with imaging techniques, such as electron microscopy or atomic for microscopy, and/or by increased size measurements shown by dynamic light scattering. In some embodiments, aggregation can be characterized by at least about a 10% increase, at least about a 25% increase, at least about a 50% increase, at least about a 100% increase, at least about a 500% increase, or at least about a 1000% increase in measured particle diameter as compared to an original measurement of the chromophoric polymer dots. For example, chromophoric polymer dots may measure a median diameter of 15 nm on day one, and then measure a median diameter of 30 nm four months later, thereby showing a 100% increase in measured particle diameter (i.e., exhibiting aggregation). In certain embodiments, the chromophoric polymer dots can be stable when stored in an appropriate aqueous solution for at least about a month, preferably at least about 2 months, more preferably at least about 4 months. In certain embodiments, a stable chromophoric nanoparticle will not aggregate or change substantially in size for at least about 1, 2, 3, 4, 5, 6, 7, 8, 9, 10, 11, 12, 13, 14, 15, 16, 17, 18, 19, 20, 21, 22, 23, 24, 30, 36, 42, 48, or more months. In one embodiment, a functionalized chromophoric nanoparticle as provided herein will remain stable in an appropriate aqueous solution for at least about 4 months. In another embodiment, a functionalized chromophoric nanoparticle as provided herein will remain stable in an appropriate aqueous solution for at least about 6 months.

In a yet another embodiment, a functionalized chromophoric nanoparticle as provided herein will remain stable in an appropriate aqueous solution for at least about one year.

In some embodiments, the term "stable" can refer to a chromophoric polymer dot resistance to dissociation of polymer molecules or dopants in the polymer dot. For example, chromophoric polymer dots can include several polymer molecules and those polymer molecules can stay in the polymer dot for a period of time before leaching out into solution. Leaching of polymer molecules from polymer dots can be characterized, for example, by decreased photophysical properties of the polymer dots. In some embodiments, decreased stability of the chromophoric polymer dots can be characterized by decreasing emission intensity over time at a wavelength corresponding to the polymer dot emission. In certain embodiments, degradation of the polymer dots can be detected by increasing emission intensity over time at a particular wavelength corresponding to polymer emission. In addition to measuring polymer emission, the polymer dots can also be designed to incorporate fluorescent dyes that are in solution during nanoparticle formation. As the polymer dots degrade, the dye can leach out and can be detected over time.

As provided further herein, the polymer dots of the present invention provide other unexpected properties in addition to showing high stability. For example, the ability to tune the amount of functionalization along the polymer allows for tuning a variety of photophysical properties (e.g., absorbance, emission brightness and/or the color of emission). In certain embodiments, the polymer dots provide unexpected brightness. Notably, in some instances, quenching of fluorescence is not increased due to particle formation. Furthermore, low, discrete numbers of functional groups on the surface of the polymer dots can reduce non-specific absorption of the Pdots to biologically relevant molecules and/or cells. It will be appreciated that polymer dots having high brightness and specific binding capabilities provide important aspects to furthering areas of imaging and detection techniques for studying chemical and biological systems.

In some embodiments, the resulting chromophoric polymer dots made from the functional semiconducting polymers can have functional groups suitable for bioconjugation. In certain embodiments, the density of hydrophilic functional groups should be carefully controlled, because many of the functional groups suitable for bioconjugation are water-soluble, which may finally result in polymers more like water-soluble semiconducting polymers (i.e., become more like semiconducting polyelectrolytes), and prevent the collapse or condensation of semiconducting polymers into stable nanoparticles. For example, Moon et al. (Moon et al. Angewandte Chemie. 2007, 46, 8223-8225) reported that semiconducting polymers with a high density of water-soluble functional side-chains can be forced to form small particles by using hard acid conditions. However, these particles made by using harsh conditions are prone to aggregation and are not stable as clearly indicated in their experimental data (Moon et al. Angewandte Chemie. 2007, 46, 8223-8225). The heavily functionalized chromophoric polymers can be characterized as polymers more like conjugated polyelectrolytes because of the hydrophilic nature of the functional groups or side chains, and these nanoparticles are in fact loose aggregates of polymers more like polyelectrolyte molecules (Moon et al. Chem. Communications 2011, 47, 8370-8372). The loose aggregates are formed without involving too much of polymer chain folding, and their loose structure is different from the compact chromophoric polymer dots collapsed from hydrophobic polymers, as described herein. Correspondingly, the nanoparticles of Moon et al. are colloidally unstable, and their aggregation behaviors are affected by polymer concentration, ionic strength, and temperature (Moon et al. Chem. Communications 2011, 47, 8370-8372). It was also unclear whether the particles of Moon et al. can be conjugated to biomolecules because large amount of water-soluble functional groups can easily cause cross-linking and aggregates. Thus far, there is no report that carefully designs semiconducting polymers with controlled density of hydrophilic functional groups in the semiconducting polymers to form stable chromophoric polymer nanoparticle with desired hydrophilic functional groups for coupling to biomolecules. In contrast, the present invention describes the discovery that the density of hydrophilic functional groups should be carefully controlled, because the hydrophilic functional groups may adversely loosen the compact internal structure, reduce per-particle fluorescence brightness, and increase nonspecific adsorption in biological labeling.

Figure 2A:
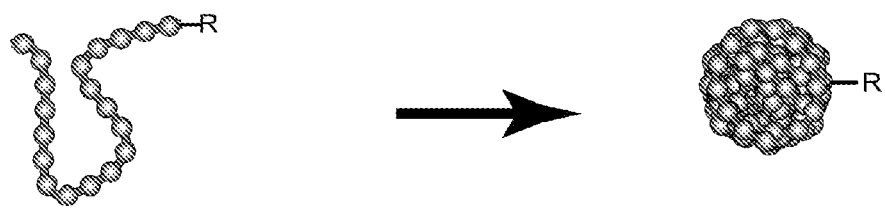
FIG. 2 (A) shows a schematic diagram of monovalent single-molecule chromophoric dot, (B) shows a schematic diagram of bivalent single-molecule chromophoric dot, and (C) shows a schematic diagram of trivalent single-molecule chromophoric dot, in accordance with some embodiments of the present invention.
Figure 2B:
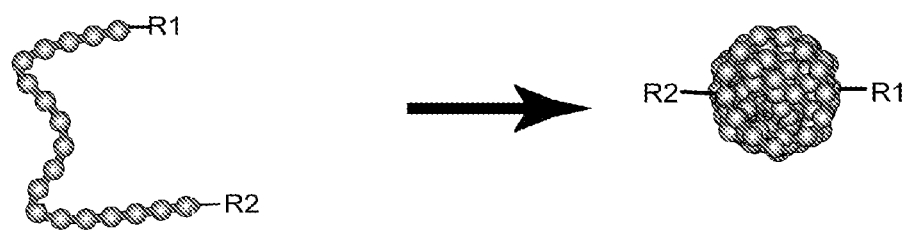
Figure 2C:
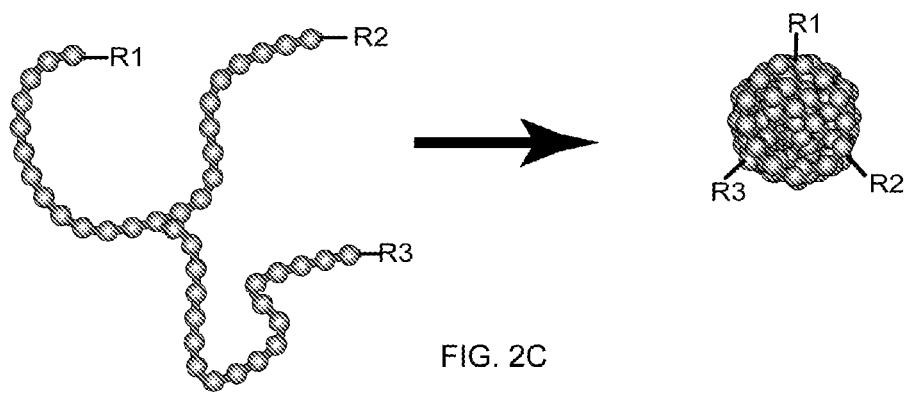

One way to control the density of hydrophilic functional groups, linear or branched semiconducting polymer molecules can be synthesized by using only terminating functional groups. The resulting polymer would have controlled functional groups. For example, a chemical unit comprising a functional group can serve as a polymerization initiator as well as a growth catalyst in polymer synthesis, and in this way each polymer molecule can be finally terminated by just one functional group (FIG. 2A). This method is also advantageous to synthesize polymers with controlled molecular weights and narrow molecular weight distributions. In addition, by general synthetic approaches each linear polymer molecule has two terminating functional groups (FIG. 2B), and each three-armed branched polymer has three terminating functional groups etc (FIG. 2C). The density of the hydrophilic functional groups in this case will be sufficiently low as not to adversely affect the collapse of the polymer chain into a stable nanoparticle that offers good performance. In this method, it is preferable there is only one polymer molecule per nanoparticle. However, it is possible to have multiple polymer molecules in a nanoparticle if needed.

In some embodiments, a sufficiently low density of hydrophilic functional groups can be maintained when a portion of the monomers with side-chain hydrophilic functional groups are incorporated into the polymer backbone during polymer synthesis so that the resulting polymer has well-controlled and sufficiently low density of side-chain functional groups (FIG. 7). Several methods can be used to control and ensure a low degree of functionalization. One method includes functionalizing only the terminal groups, either some of the terminal groups or all of the terminal groups. Another method includes using a low number of functional groups on the side chains. For example, as shown in the last scheme in FIG. 7, x is adjusted until the number of functional groups present does not adversely affect the formation and stability of the formed polymer dots. In some embodiments, x may vary depending on the particular chromophoric polymer and the nature of its backbone and side chains. Other methods to control the degree of functionalization for forming stable chromophoric polymer dots may be based on adjusting the ratio of monomers that contain functional groups versus monomers that do not contain functional groups. Additional methods may be based on any combination of the schemes depicted in the figure or described here in the caption.

As provided herein, embodiments of the present invention can include semiconducting polymers with only a portion of side-chain hydrophilic functional groups. The polymers of the present invention are distinguished from water-soluble semiconducting polymer (semiconducting polyelectrolytes) where nearly every monomer repeating unit has a side-chain hydrophilic functional group or hydrophilic moiety. The chromophoric polymer dots of the present invention can include semiconducting polymers with only a portion of side-chain hydrophilic functional groups, which on one hand can be easily prepared into small nanoparticles with a hydrophobic core, and on the other hand can provide hydrophilic functional groups for bioconjugation. In contrast, the particles disclosed by Moon et al. do not provide the design control, such as when each repeating unit (e.g., monomer) has a side-chain hydrophilic functional group or moiety, and would be troublesome and laborious to use in nanoparticle preparation and bioconjugation. More importantly, nanoparticles formed using these heavily functionalized semi-conducting polymers with hydrophilic moieties often do not have good stability. Additionally, chromophoric polymers that are heavily functionalized with hydrophilic moieties (e.g. each monomer has a side-chain hydrophilic functional group) also often cannot be collapsed into the compact nanoparticle form using precipitation. Example 8, for example, illustrates this distinction. As compared to the loose particle structure of Moon et al., the per-particle absorption cross-section of the loose aggregates is decreased as compared to the compact polymer dots formed from, e.g., hydrophobic polymers described herein. The decrease can be attributed to, e.g., a lower number of chromophores in the loose aggregate particles of Moon et al. Moreover, the heavily functionalized polymers of Moon et al. exhibit lower fluorescence quantum yield as compared to the polymers with low density of functionalization described herein. The combined factors of small absorption cross section and low quantum yield can significant decrease the per-particle fluorescence brightness (Example 7) Additionally, chromophoric polymer dots formed from heavily functionalized polymers also yield significant nonspecific labeling in biological applications as compared to those formed from chromophoric polymers with low density functionalization, as described herein (Example 9).

In one embodiment, chromophoric polymer dots can be formed by precipitation. This technique involves the rapid addition (e.g. facilitated by sonication or vigorous stirring) of a dilute chromophoric polymer solution (e.g. chromophoric polymer dissolved in an organic solvent) into an excess volume of non-solvent (but miscible with the organic solvent), such as water or another physiologically relevant aqueous solution. For example, in some of the procedures described herein, the chromophoric polymer can be first dissolved into an organic solvent where the solubility is good (good solvent), such as THF (tetrahydrofuran), after which the dissolved polymer in THF is added to an excess volume of water or buffer solution, which is a poor solvent for the hydrophobic chromophoric polymers but which is miscible with the good solvent (THF). The resulting mixture is sonicated or vigorously stirred to assist the formation of chromophoric polymer dots, then the organic solvent is removed to leave behind well dispersed chromophoric nanoparticles. In using this procedure, the chromophoric polymer should be sufficiently hydrophobic to dissolve into the organic solvent (e.g. THF). The introduction of a high density of hydrophilic functional groups on side chains for coupling to biomolecules or high density of hydrophilic side chains (such as that described by Moon et al.) will make the resulting polymer, in a fashion similar or identical to the behavior of polyelectrolytes, insoluble or poorly soluble in an organic solvent (e.g., THF).

By understanding the requirements and parameters that are important for stable chain collapse to form stable chromophoric polymer dots, the present invention describes compositions of the functionalized chromophoric polymer with a controlled and low degree of hydrophilic functional groups such that stable functionalized chromophoric polymer dots can be formed, preferably using precipitation. However, other methods of forming chromophoric polymer dots are also possible, including but not limited to various methods based on emulsions (e.g. mini or micro emulsion) or precipitations or condensations. Other polymers having hydrophobic functional groups can also be employed, in which the hydrophobic functional groups do not affect the collapse and stability of the chromophoric polymer dot. The hydrophobic functional groups on the surface of the nanoparticles can then be converted to hydrophilic functional groups (e.g., by post-functionalization) for bioconjugation or directly link the hydrophobic functional groups to biomolecules. This latter approach can work particularly well using functional groups that are both hydrophobic and clickable (i.e. chemical reactions that fall within the framework of click chemistry), including but not limited to alkyne, strained alkyne, azide, diene, alkene, cyclooctyne, and phosphine groups.

Monovalent Chromophoric Polymer Dot

One embodiment of the present invention provides a monovalent chromophoric polymer dot. The monovalent chromophoric polymer dot comprises chromophoric polymer dot that bears only one functional group. The "monovalent" as that term is used herein refers to just one functional group that is attached to the surface of the chromophoric polymer dot.

Figure 1A:
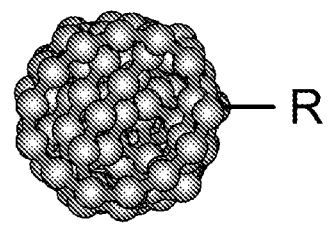
FIG. 1(A) shows schematic diagram of monovalent chromophoric dot, and (B) shows the schematic diagram of a biomolecular conjugate of monovalent chromophoric polymer dot, in accordance with an embodiment of the present invention.

FIG. 1A shows the schematic diagram of monovalent chromophoric polymer dot with one functional group R. The functional group can be any of the groups such as carboxylic acid or salts thereof, amino, mercapto, azido, alkyne, strained alkyne, azide, phosphine, cyclooctyne, aldehyde, ester, hydroxyl, carbonyl, sulfate, sulfonate, phosphate, cyanate, succinimidyl ester, substituted derivatives thereof. In general, any other functional groups that allow bioconjugation may be used. Such functional groups could be found by one of ordinary skill in the art, for example in Bioconjugate Techniques (Academic Press, New York, 1996 or later versions) the content of which is herein incorporated by reference in its entirety for all purposes. In a particular embodiment, the functional group can be any structure that comprises biotin, folic acid, folate, phalloidin, or a peptide, a protein, a nucleic acid, a carbohydrate, a lipid, and the like, which can directly or indirectly bind to biological entities.

Bioconjugates of Functionalized Chromophoric Dot

In some embodiments, the present invention provides a bioconjugate that can include a functionalized chromophoric polymer dot as described above and a biomolecule, wherein the biomolecule is attached to the polymer dot either directly or indirectly by the functional groups. The bioconjugates can also include functionalized chromophoric polymer dots as described above, associated with biological particle such as virus, bacteria, cells, biological or synthetic vesicles such as liposomes. The functionalized chromophoric polymer dots can include one or more functional groups that are formed from the chromophoric polymer with one or two terminating functional groups, or low density side-chain functional groups.

Figure 1B:
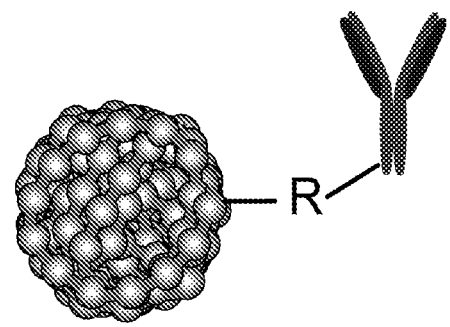

In certain embodiments, the present invention provides a bioconjugate comprising a monovalent chromophoric polymer dot as described above and a biomolecule, wherein the biomolecule is attached to the polymer dot either directly or indirectly by the functional group. The bioconjugates also comprise monovalent chromophoric polymer dot as described above, associated with biological particle such as virus, bacteria, cells, biological or synthetic vesicles such as liposomes. FIG. 1B shows the schematic diagram of monovalent chromophoric polymer dot associated with a biomolecule by a functional group R. The term "biomolecule" is used to describe a synthetic or naturally occurring protein, glycoprotein, peptide, amino acid, metabolite, drug, toxin, nuclear acid, nucleotide, carbohydrate, sugar, lipid, fatty acid and the like. Desirably, the biomolecule is attached to the functional group of monovalent chromophoric polymer dot via a covalent bond. For example, if the functional group of the polymer dot is a carboxyl group, a protein biomolecule can be directly attached to the polymer dot by cross-linking the carboxyl group with an amine group of the protein molecule.

As used herein, the term "cross-linking agent" is used to describe a compound or moiety that is capable of forming a chemical bond between molecular groups on similar or dissimilar molecules so as to covalently bond together the molecules. Examples of common cross-linking agents are known in the art. See, for example, Bioconjugate Techniques (Academic Press, New York, 1996 or later versions) the content of which is herein incorporated by reference in its entirety for all purposes. Indirect attachment of the biomolecule to monovalent chromophoric polymer dots can occur through the use of "linker" molecule, for example, avidin, streptavidin, neutravidin, biotin or a like molecule.

Single-Molecule Polymer Dot: Monovalent, Bivalent, or Multivalent

Functional groups described herein can be included in the chromophoric polymers in a variety of ways. For example, a functional group can be linked (e.g., covalently bonded) to the backbone, the side chain, or one of the terminal units of a chromophoric polymer. As described further herein, a monovalent polymer dot can include a single polymer molecule that includes only one functional group, e.g., at one of two terminal units of the single linear polymer molecule. A bivalent polymer dot can include a single polymer molecule that includes two functional groups, e.g., at each of the two terminal units of the single linear polymer molecule. A trivalent polymer dot can include a single polymer molecule that includes three functional groups, e.g., attachment of functional groups only to the three terminal units of a three-arm branched polymer. Similarly, branched polymer can be used in preparing other multivalent polymer dots, e.g., that have functional groups attached at the terminal units of four-arm, five-arm, six-arm, and branched polymers with higher numbers of branches.

In some embodiments, advantages can arise from polymer dots that include a single polymer molecule having at least one functional group at a terminal unit. For example, the attachment of only one functional group to a terminal unit of a chromophoric polymer can be well controlled in polymer synthesis. For example, a chemical unit comprising a functional group can serve as a polymerization initiator as well as a growth catalyst in polymer synthesis, and in this way each polymer molecule includes just one functional group at the terminus. Attachment of functional groups only to the two terminal units of a linear chromophoric polymer can also be well controlled in polymer synthesis. For example, a chemical unit comprising a functional group can be used as a capping agent to terminate the polymer growth in polymer synthesis, thereby resulting in each linear polymer molecule including only two functional group in the two terminal units. Similarly, the attachment of functional groups for multivalent polymer dots can be well controlled in polymer synthesis, e.g., functional groups can only be added to the three terminal units of a three-arm branched polymer.

In certain embodiments, addition of functional groups to polymer terminal units can be compared to polymers, in which the functional groups are randomly positioned along the backbone. For example, the number of functional groups in a polymer by side-chain functionalization or backbone functionalization can be difficult to produce polymers having a precise number of functional groups. Instead, the number of functional groups on the polymers usually follows a distribution. In certain cases, the functional group in the terminal units can be also advantageous to the side chains in other aspects. As compared to side-chain and backbone functionalization, functionalization of the terminal units does not have as much affect on the collapse of the polymer to form polymer dots. Also, the terminal functional groups can be more accessible to an aqueous environment for bioconjugation, whereas the side-chain functional groups may be embedded inside the polymer dot and unavailable for bioconjugation.

In one embodiment, the chromophoric polymer dot comprises only one chromophoric polymer molecule that is linked with one functional group (e.g., R) (as shown in FIG. 2A). Such a chromophoric polymer dot is a monovalent single-molecule dot that may provide unique properties such as monodispersed size, and uniform fluorescence brightness. The functional group can be covalently linked to backbone, side chain, or one of the terminating units of the chromophoric polymer. The functional group can be any of the groups such as carboxylic acid or salts thereof, amino, mercapto, azido, alkyne, phosphine, cyclooctyne, aldehyde, hydroxyl, carbonyl, sulfate, sulfonate, phosphate, cyanate, ester, succinimidyl ester, substituted derivatives thereof. In general, any other functional groups that are suitable for bioconjugation may be used. Such functional groups could be found by one of ordinary skill in the art, for example in Bioconjugate Techniques (Academic Press, New York, 1996 or later versions), the content of which is herein incorporated by reference in its entirety for all purposes. Chromophoric polymer comprising one functional group can be synthesized by many approaches. For example, a chemical unit comprising a functional group can serve as a polymerization initiator as well as a growth catalyst in polymer synthesis, and in this way each polymer molecule is finally terminated by just one functional group (FIG. 2A). This method is also advantageous to synthesize polymers with controlled molecular weights and narrow molecular weight distributions. Monovalent single-molecule polymer dot can be prepared by the solvent mixing method in Example 1, or any other method found in the art.

Figure 4:
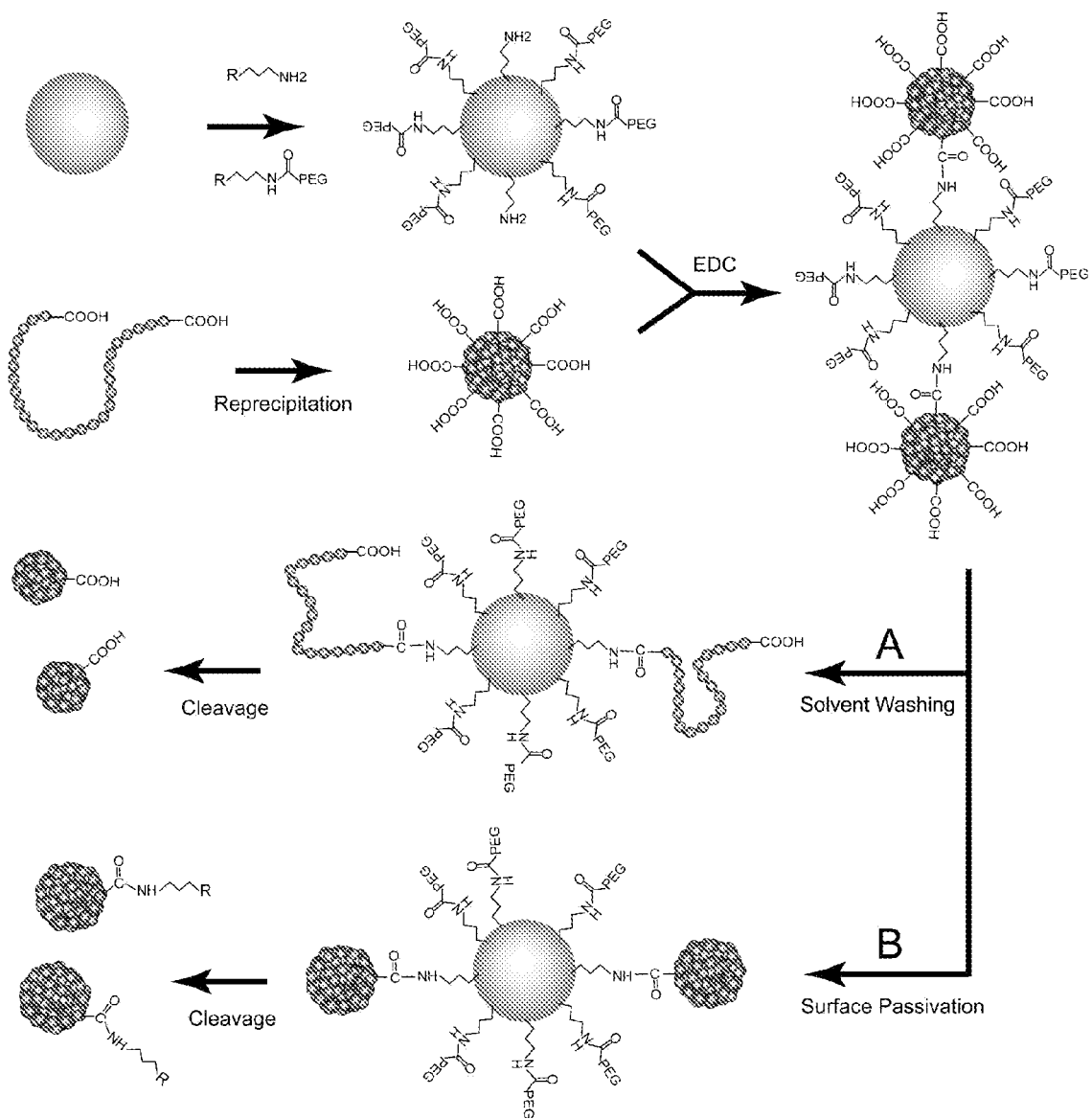
FIG. 4 shows a schematic diagram for preparing monovalent chromophoric polymer dots via an engineered particle surface. Scheme A shows a method for preparing single-molecule polymer dot. Scheme B shows a method for modifying functionalized chromophoric polymer dot to monovalent polymer dot, in accordance with some embodiments of the present invention.

In some embodiments, the chromophoric polymer dots can include one polymer molecule with two functional groups (e.g., R1 and R2). Such a chromophoric polymer dot is bivalent single-molecule dot that may provide unique properties such as monodispersed size, and uniform fluorescence brightness, and conjugation to two different types of biomolecules. The two functional groups can be covalently linked to the backbone, side chains, and/or the terminating units of the chromophoric polymer. In a preferred embodiment, the chromophoric polymer dot comprises one linear polymer molecule with two terminating functional groups. A schematic diagram of linear polymer molecule with two terminating functional groups is shown in FIG. 2B, and the chemical structure of a specific chromophoric polymer PDHF—COOH with two terminating carboxyl groups is shown in FIG. 3. Such a chromophoric polymer dot is a bivalent single-molecule dot that is, e.g., useful in certain applications such as for forming polarized fluorescent bioconjugates, or assembling the dots into one-dimensional structures. The two functional groups R1 and R2 may be the same, or they may be different. The functional groups can be any of the groups such as carboxylic acid or salts thereof, amino, mercapto, azido, alkyne, phosphine, cyclooctyne, aldehyde, hydroxyl, carbonyl, sulfate, sulfonate, phosphate, cyanate, ester, succinimidyl ester, substituted derivatives thereof, and any combination thereof. In general, any other functional groups that allow bioconjugation may be used. Such functional groups could be found by one of ordinary skill in the art, for example in Bioconjugate Techniques (Academic Press, New York, 1996 or later versions) the content of which is herein incorporated by reference in its entirety for all purposes. Bivalent single-molecule polymer dot can be prepared by the solvent mixing method as shown in Example 1, or any other method found in the art. In a particular embodiment, bivalent single-molecule chromophoric polymer dot can be modified to a monovalent dot by the method provided in this invention, as shown in FIG. 4 and Example 2.

In another embodiment, the chromophoric polymer dot comprises one polymer molecule with three hydrophilic functional groups (e.g., R1, R2, and R3). Such a chromophoric polymer dot is trivalent single-molecule dot that may provide unique properties such as monodispersed size, and uniform fluorescence brightness. The three functional groups can be covalently linked to the backbone, side chains, and/or the terminating units of the chromophoric polymer. In a preferred embodiment, the chromophoric polymer dot comprises single molecule of three-arm branched polymer, where each arm contains one functional group (a schematic diagram is shown in FIG. 2C). The three functional groups (e.g., R1, R2 and R3) may be the same, or they may be different. The functional groups can be any of the groups such as carboxylic acid or salts thereof, amino, mercapto, azido, alkyne, phosphine, cyclooctyne, aldehyde, hydroxyl, carbonyl, sulfate, sulfonate, phosphate, cyanate, ester, succinimidyl ester, substituted derivatives thereof, and any combination thereof. In general, any other functional groups that allow bioconjugation may be used. Such functional groups could be found by one of ordinary skill in the art, for example in Bioconjugate Techniques (Academic Press, New York, 1996 or later versions) the content of which is herein incorporated by reference in its entirety for all purposes. Such a single-molecule dot is trivalent, but has well-controlled functional groups (determined by the number of backbone branches) that are useful for certain applications such as polarized fluorescent bioconjugates, or directed nanoparticle assembly. Trivalent single-molecule polymer dot can be prepared by the solvent mixing method as shown in Example 1, or any other method found in the art. In a particular embodiment, trivalent single-molecule chromophoric polymer dot can be modified to monovalent dot by the method provided in this invention, as shown in FIG. 4.

In some embodiments, the chromophoric polymer dots can include one polymer molecule with four functional groups, or five functional groups, or six functional groups, or more functional groups. Such a chromophoric polymer dot is multivalent single-molecule dot that can provide unique properties such as monodispersed size, uniform fluorescence brightness, or bioconjugation capability. The functional groups can be covalently linked to the backbone, side chains, and/or the terminating units of the chromophoric polymer. In a preferred embodiment, the chromophoric polymer dot comprises single molecule of four-arm branched polymer, five-arm branched polymer, six-arm branched polymer etc. where each arm contains one functional group. The functional groups can be any of the groups such as carboxylic acid or salts thereof, amino, mercapto, azido, alkyne, phosphine, cyclooctyne, aldehyde, hydroxyl, carbonyl, sulfate, sulfonate, phosphate, cyanate, ester, succinimidyl ester, substituted derivatives thereof, and any combination thereof. In general, any other functional groups that are suitable for bioconjugation may be used. Such functional groups could be found by one of ordinary skill in the art, for example in Bioconjugate Techniques (Academic Press, New York, 1996 or later versions) the content of which is herein incorporated by reference in its entirety for all purposes. The functional groups may be the same, or they may be different. Such a single-molecule dot is multivalent, but has well-controlled functional groups (pre-defined by the number of backbone branches) that are useful for certain applications such as polarized fluorescent bioconjugates, or directed nanoparticle assembly, or bioconjugation. Multivalent single-molecule polymer dot can be prepared by the solvent mixing method as shown in Example 1, or any other method found in the art. In a particular embodiment, multivalent single-molecule chromophoric polymer dot can be modified to monovalent dot by the method provided in this invention, as shown in FIG. 4.

Functionalized Multi-Molecule Chromophoric Polymer Dot: Multivalent to Monovalent In some embodiments, the chromophoric polymer dots can include a functionalized multi-molecule chromophoric polymer dot that can be modified to form a monovalent dot. Functionalized chromophoric dot can be prepared by using chromophoric polymer molecules bearing functional groups (such as PDHF—COOH in FIG. 3). The functional groups can be covalently linked to the backbone, side chain, and/or the terminating unit of the chromophoric polymer. Alternatively, the chromophoric polymer dot may be functionalized through a functionalization agent. Functionalization agents and method are known, for example, see, U.S. Provisional Patent Application Ser. No. 61/259,611, the contents of which are herein incorporated by reference in their entirety for all purposes. The functional group can be any of the groups such as carboxylic acid or salts thereof, amino, mercapto, azido, alkyne, phosphine, cyclooctyne, aldehyde, hydroxyl, carbonyl, sulfate, sulfonate, phosphate, cyanate, ester, succinimidyl ester, substituted derivatives thereof, and any combination thereof. In general, any other functional groups that are suitable for bioconjugation may be used. Such functional groups could be found by one of ordinary skill in the art, for example in Bioconjugate Techniques (Academic Press, New York, 1996 or later versions) the content of which is herein incorporated by reference in its entirety for all purposes. These functionalized chromophoric polymer dots can be modified to monovalent chromophoric polymer dot by the method provided in this invention, as shown in FIG. 4.

Methods for Preparing Chromophoric Polymer Dots: Monovalent, Bivalent, or Multivalent Polymer Dots As provided herein, the chromophoric polymer dots can be made using a variety of methods. For example, described herein are methods involving precipitation of the polymers to form the polymer dots. It will be appreciated the myriad ways of forming polymer dots, which can also include, e.g., emulsion-based techniques. Similarly, one of ordinary skill in the art will appreciate the variety of methods described herein with respect to functionalizing the polymer dots by, e.g., pre- and post-functionalization with functional groups, such as hydrophobic functional groups, hydrophilic functional groups, or a combination thereof.

In one aspect, the present invention provides a method for making a rationally functionalized single-chain chromophoric nanoparticle having a defined number of reactive functional groups on its surface, the method comprising the steps of: (a) collapsing a homogenous population of semiconducting polymers conjugated to one or more reactive functional group in an aqueous environment to form a chromophoric nanoparticle comprising a plurality of reactive functional groups; (b) attaching the nanoparticle to a solid phase at a single point by forming a covalent bond between a reactive functional group on the nanoparticle and the solid phase; (c) washing the nanoparticle in an organic solvent to disrupt the structure of the nanoparticle and to retain only the polymer conjugated to the solid surface; (d) washing the attached polymer back into an aqueous environment to collapse the polymer into a single-chain chromophoric nanoparticle; and (e) cleaving the bond between the solid phase and the reactive functional group to release the single-chain chromophoric nanoparticle from the solid phase. In some embodiments, the step of cleaving the bond maintains a reactive functional group on the surface of the nanoparticle. In certain embodiments, the step of cleaving the bond modifies the reactive functional group, generating a different reactive functional group on the surface of the nanoparticle.

In another aspect, the present invention provides a method for making a monovalent chromophoric nanoparticle having a single reactive functional group on its surface, the method comprising the steps of: (a) collapsing a semiconducting polymer conjugated to one or more reactive functional groups in an aqueous environment to form a chromophoric nanoparticle comprising a plurality of reactive functional groups; (b) attaching the nanoparticle to a solid phase at a single point by forming a covalent bond between a reactive functional group on the nanoparticle and the solid phase; (c) treating the nanoparticle to remove all of the unbound reactive functional groups from the surface of the nanoparticle; and (d) cleaving the bond between the solid phase and the reactive functional group to release the chromophoric nanoparticle from the solid phase. In some embodiments, the step of cleaving the bond maintains a reactive functional group on the surface of the nanoparticle. In certain embodiments, the step of cleaving the bond modifies the reactive functional group, generating a different reactive functional group on the surface of the nanoparticle.

In one example embodiment, single-molecule chromophoric polymer dot can be prepared by using the solvent mixing method as shown in Example 1, where the polymer precursor solution is dilute enough. For single polymer molecules, collapse into a single polymer dot can be facilitated, e.g., with low polymer concentrations where polymers are spatially distributed in solution such that only intramolecular collapse occurs, rather than intermolecular collapse with another polymer molecule. Dilute solutions for single polymer dot formation can range from less than about 1000 ppm, less than about 500 ppm, less than about 100 ppm, less than about 50 ppm, less than about 20 ppm, less than about 10 ppm, less than about 5 ppm, less than about 1 ppm, or less. An example first step of the methods herein is to synthesize chromophoric polymer molecule bearing functional groups, such as carboxylic acid or salts thereof, amino, mercapto, azido, alkyne, phosphine, cyclooctyne, aldehyde, hydroxyl, carbonyl, sulfate, sulfonate, phosphate, cyanate, ester, succinimidyl ester, substituted derivatives thereof, and combinations thereof. In general, any other functional groups that allow bioconjugation may be used. Such functional groups could be found by one of ordinary skill in the art, for example in Bioconjugate Techniques (Academic Press, New York, 1996 or later versions) the content of which is herein incorporated by reference in its entirety for all purposes. A functional group can be created with covalent bonding to the backbone, side chain, or terminating unit of the chromophoric polymer. In the second step, the functionalized chromophoric polymer is used as a precursor for preparing single-molecule dot by using the solvent mixing method as shown in Example 1. In one embodiment, the single-molecule dot could be monovalent (e.g., with only one functional group available for bioconjugation) when each polymer precursor molecule has just one functional group. In other embodiments, the single-molecule dot could be bivalent, or multivalent when each polymer precursor molecule has two, or more functional groups, which are useful for certain applications.

In some embodiments, any functionalized multi-molecule chromophoric polymer dot can be modified to form a single-molecule polymer dot that may be monovalent, bivalent, or multivalent. The modification is to remove some polymer molecules from the dot, but leave only one molecule that may have just one functional group, two or more functional groups. In one embodiment, an engineered surface can be used to facilitate the modification. The engineered surface may have certain functional groups such as carboxylic acid or salts thereof, amino, mercapto, azido, alkyne, phosphine, cyclooctyne, aldehyde, hydroxyl, carbonyl, sulfate, sulfonate, phosphate, cyanate, ester, succinimidyl ester, substituted derivatives thereof, and combinations thereof. In general, any other functional groups that are suitable for bioconjugation may be used. Such functional groups could be found by one of ordinary skill in the art, for example in Bioconjugate Techniques (Academic Press, New York, 1996 or later versions) the content of which is herein incorporated by reference in its entirety for all purposes.

The surface can be a flat surface such as a coverslip or a curved surface from any particles. The surfaces can be silica, metal, semiconducting, silicon, and different polymer surfaces. The functionalized multi-molecule chromophoric polymer dot described above is attached to the surface by only one chromophoric polymer molecule via any stable physical or chemical association. All the free molecules (except the one associated with the surface) in the chromophoric polymer dot can be removed, such as by washing the surface with an organic solvent, so that only the molecule associated with the surface is retained. Then the single-molecule chromophoric dot can be released from the surface by any physical or chemical methods. The resulting single-molecule dot could be monovalent, bivalent, or multivalent, depending on the number of functional groups in the original polymer molecule. This method for preparing single-molecule dot is shown by Scheme A in FIG. 4. In some embodiments, the polymer dots can be attached to the surface by click chemistry. The functional groups on the surface or in the polymers include but not limit to those used for click chemistry, such as alkyne, strained alkyne, azide, diene, alkene, cyclooctyne, and phosphine groups. FIG. 20 shows one of such examples, in which PFBT-alkyne dots were attached to silica beads by alkyne-azide click reaction. The PFBT dots can be cleaved after solvent washing to form single-chain dots. An experiment example for modifying functionalized chromophoric polymer dot to monovalent single-molecule dot is shown in Example 2.

Method for Preparing Monovalent Chromophoric Polymer Dots from Functionalized Multivalent Chromophoric Polymer Dots In some embodiments, monovalent chromophoric polymer dots can be prepared by modifying any functionalized multivalent chromophoric polymer dots to monovalent dots. The original functionalized multivalent polymer dot may comprise one or more chromophoric polymer molecules. The original functionalized polymer dot may also comprise chromophoric polymer, physically mixed or chemically cross-linked with other components including, e.g., fluorescent dye, inorganic luminescent materials, magnetic materials, metal materials, which can have additional functionalities such as magnetic functions, plasmon resonance functions, and the like.

This embodiment includes a two-step process: the first step is to prepare functionalized chromophoric polymer dots bearing functional groups such as carboxylic acid or salts thereof, amino, mercapto, azido, alkyne, phosphine, cyclooctyne, aldehyde, hydroxyl, carbonyl, sulfate, sulfonate, phosphate, cyanate, ester, succinimidyl ester, substituted derivatives thereof, and combinations thereof. In general, any other functional groups that allow bioconjugation may be used. Such functional groups could be found by one of ordinary skill in the art, for example in Bioconjugate Techniques (Academic Press, New York, 1996 or later versions) the content of which is herein incorporated by reference in its entirety for all purposes. The chromophoric polymer dots can be functionalized by attaching any organic molecule, such as by any stable physical or chemical association, to the chromophoric polymer dots. The functionalization molecule is attached to the chromophoric polymer dots by physical association or chemical bonding, and provides surface functional groups on chromophoric polymer dot. Preferably, the functionalization molecule is a polymer, which may or may not be chromophoric. Methods for preparing functionalized multivalent dots are known, for example, see, U.S. Provisional Patent Application Ser. No. 61/259,611, the contents of which are herein incorporated by reference in their entirety for all purposes.

The second step is to modify the functionalized multivalent chromophoric polymer dot to monovalent polymer dot. The modification is to passivate or remove the majority of functional groups, but leave only one active functional group. In one embodiment, an engineered surface can be used to facilitate the modification. The engineered surface may have certain functional groups such as carboxylic acid or salts thereof, amino, mercapto, azido, alkyne, phosphine, cyclooctyne, aldehyde, hydroxyl, carbonyl, sulfate, sulfonate, phosphate, cyanate, ester, succinimidyl ester, substituted derivatives thereof, and combinations thereof. The surface can be a flat surface such as a coverslip or a curved surface from any particles. The surfaces can be silica, metal, semiconducting, silicon, and different polymer surfaces. The engineered surface can be a flat surface such as a coverslip or a curved surface from any particles. In some embodiment, the polymer dots can be attached to the surface by click chemistry. The functional groups on the surface or in the polymer molecules include but not limit to those used for click chemistry, such as alkyne, strained alkyne, azide, diene, alkene, cyclooctyne, and phosphine groups. FIG. 20 shows one of such schemes that PFBT-alkyne dots were attached to silica beads by alkyne-azide click reaction. The PFBT dots can be cleaved after surface passivation to form monovalent dots. The original functionalized multivalent chromophoric dot described above is attached to the surface by only one functional group via any stable physical or chemical association. All the free functional groups (except the one connected to the surface) on the chromophoric dot can be passivated or removed. Then the chromophoric dot can be released from the surface by any physical or chemical method and the modified chromophoric dot would have only one functional group, which could be the original one or a different one. This method for modifying functionalized chromophoric polymer dot to monovalent polymer dot is shown by Scheme B in FIG. 4.

As taught in U.S. Provisional Patent Application Ser. No. 61/259,611, in one embodiment, the functionalized nanoparticle can contain a polystyrene based comb-like polymer. Non limiting examples of polystyrene based comb-like polymers include, polystyrene graft acrylic acid, polystyrene graft ethylene oxide functionalized with carboxy, polystyrene graft ethylene oxide functionalized with amine, polystyrene graft ethylene oxide functionalized with thiol, polystyrene graft ethylene oxide functionalized with succinimidyl ester, polystyrene graft ethylene oxide functionalized with azide, polystyrene graft ethylene oxide functionalized with alkyne, polystyrene graft ethylene oxide functionalized with cyclooctyne, polystyrene graft ethylene oxide functionalized with ester, phosphine, polystyrene graft butyl alcohol, and the like.

In another embodiment, the functionalized nanoparticle can contain a poly(methyl methacrylate) based comb-like polymers. Non-limiting examples of poly(methyl methacrylate) based comb-like polymers include, poly(methyl methacrylate) graft acrylic acid, poly(methyl methacrylate) graft ethylene oxide functionalized with carboxy, poly(methyl methacrylate) graft ethylene oxide functionalized with amine, poly(methyl methacrylate) graft ethylene oxide functionalized with thiol, poly(methyl methacrylate) graft ethylene oxide functionalized with succinimidyl ester, poly(methyl methacrylate) graft ethylene oxide functionalized with azide, poly(methyl methacrylate) graft ethylene oxide functionalized with alkyne, poly(methyl methacrylate) graft ethylene oxide functionalized with cyclooctyne, poly(methyl methacrylate) graft ethylene oxide functionalized with ester, poly(methyl methacrylate) graft ethylene oxide functionalized with phosphine, and the like.

In yet another embodiment, the functionalized nanoparticle can contain a comb-like polymer comprising carboxyl, amine, thiol, ester, succinimidyl ester, azide, alkyne, cyclooctyne, or phosphine groups.

Likewise, in one embodiment, the functionalized nanoparticle can contain a polymer functionalized on the terminal monomeric unit, for example with a carboxyl, amine, thiol, ester, succinimidyl ester, azide, alkyne, cyclooctyne, phosphine, or similar functional group. Examples of polymers that may be used include, without limitation, poly(meth)acrylate polymers, polyacrylamide polymers, polyisobutylene, polydiene, polyphenylene, polyethylene, poly(ethylene glycol), polylactide, polystyrene, polysiloxane, poly(vinyl pyridine), poly(vinylpyrrolidone), polyurethane, a block copolymer thereof, a random or alternating copolymer thereof, and the like.

In certain embodiments, a functionalized nanoparticle can contain a copolymer having one or more functionalized monomeric units, for example an amphiphilic polymer. As described herein, when designing a chromophoric nanoparticle containing an amphiphilic polymer, care should be taken to ensure the hydrophilic functional groups do not adversely affect the collapse of the polymer chain into a nanoparticle form or do not adversely affect the stability of the formed chromophoric polymer dots. This can be achieved, e.g., by adjusting the percentage of amphiphilic functionalization polymer relative to the chromophoric polymer.

In some embodiments, the functionalized nanoparticle will contain an amphiphilic copolymer, for example, (1) poly((meth)acrylic acid) based copolymers such as: poly(acrylic acid-b-acrylamide), poly(acrylic acid-b-methyl methacrylate), poly(acrylic acid-b-N-isopropylacrylamide), poly(n-butylacrylate-b-acrylic acid), poly(sodium acrylate-b-methyl methacrylate), poly(methacrylic acid-b-neopentyl methacrylate), poly(methyl methacrylate-b-acrylic acid), poly(methyl methacrylate-b-methacrylic acid), poly(methyl methacrylate-b-N,N-dimethyl acrylamide), poly(methyl methacrylate-b-sodium acrylate), poly(methyl methacrylate-b-sodium methacrylate), poly(neopentyl methacrylate-b-methacrylic acid), poly(t-butyl methacrylate-b-ethylene oxide), poly(2-acrylamido-2-methylpropanesulfonic acid-b-acrylic acid); (2) polydiene based copolymers such as: poly(butadiene(1,2 addition)-b-ethylene oxide), poly(butadiene(1,2 addition)-b-methylacrylic acid, poly(butadiene (1,4 addition)-b-acrylic acid), poly(butadiene(1,4 addition)-b-ethylene oxide, poly(butadiene(1,4 addition)-b-sodium acrylate), poly(butadiene(1,4 addition)-b-N-methyl 4-vinyl pyridinium iodide), poly(isoprene-b-ethylene oxide), poly (isoprene-b-ethylene oxide), and poly(isoprene-b-N-methyl 2-vinyl pyridinium iodide); (3) poly(ethylene oxide) based copolymers such as: poly(ethylene oxide-b-acrylic acid), poly(ethylene oxide-b-acrylamide), poly(ethylene oxide-b-butylene oxide), poly(ethylene oxide-b-F-caprolactone), poly(ethylene oxide-b-lactide), poly(ethylene oxide-b-lactide), poly(ethylene oxide-b-methacrylic acid), poly(ethylene oxide-b-methyl acrylate), poly(ethylene oxide-b-N-isopropylacrylamide), poly(ethylene oxide-b-methyl methacrylate), poly(ethylene oxide-b-nitrobenzyl methacrylate), poly(ethylene oxide-b-N,N-dimethylaminoethylmethacrylate), poly(ethylene oxide-b-propylene oxide), poly(ethylene oxide-b-t-butyl acrylate), poly(ethylene oxide-b-t-butyl methacrylate), poly(ethylene oxide-b-tetrahydrofurfuryl methacrylate), poly(ethylene oxide-b-2-ethyl oxazoline), poly(ethylene oxide-b-2-hydroxyethyl methacrylate), poly(ethylene oxide-b-2-methyl oxazoline); (4) polyisobutylene based copolymers such as poly(isobutylene-b-acrylic acid), poly(isobutylene-b-ethylene oxide), poly(isobutylene-b-methacrylic acid); (5) polystyrene based copolymers such as poly(styrene-b-acrylamide), poly(styrene-b-acrylic acid), poly(styrene-b-cesium acrylate), poly(styrene-b-ethylene oxide), poly(styrene-b-ethylene oxide) acid cleavable at the block junction, poly(styrene-b-methacrylic acid), poly(4-styrenesulfonic acid-b-ethylene oxide), poly(styrenesulfonic acid-b-methylbutylene), poly(styrene-b-N,N-dimethylacrylamide), poly(styrene-b-N-isopropyl acrylamide), poly(styrene-b-N-methyl 2-vinyl pyridinium iodide), poly(styrene-b-N-methyl-4-vinyl pyridinium iodide), poly(styrene-b-propylacrylic acid), poly(styrene-b-sodium acrylate) poly(styrene-b-sodium methacrylate), poly (p-chloromethyl styrene-b-acrylamide), poly(styrene-co-p-chloromethyl styrene-b-acrylamide), poly(styrene-co-p-chloromethyl styrene-b-acrylic acid), poly(styrene-b-methylbutylene-co-isoprene sulfonate); (6) polysiloxane based copolymers such as poly(dimethylsiloxane-b-acrylic acid), poly(dimethylsiloxane-b-ethylene oxide), poly(dimethylsiloxane-b-methacrylic acid); (7) poly(ferrocenyldimethylsilane) based copolymers such as poly(ferrocenyldimethylsilane-b-ethylene oxide); (8) poly(2-vinyl naphthalene) based copolymers such as poly(2-vinyl naphthalene-b-acrylic acid), (9) poly (vinyl pyridine and N-methyl vinyl pyridinium iodide) based copolymers such as poly(2-vinyl pyridine-b-ethylene oxide), poly(2-vinyl pyridine-b-methyl acrylic acid), poly(N-methyl 2-vinyl pyridinium iodide-b-ethylene oxide), poly(N-methyl 4-vinyl pyridinium iodide-b-methyl methacrylate), poly(4-vinyl pyridine-b-ethylene oxide) PEO end functional OH; (10) poly(vinyl pyrrolidone) based copolymers such as poly(vinyl pyrrolidone-b-D/L-lactide); and the like.

Methods of Using Chromophoric Polymer Dots

The present invention further provides methods of using the polymer dots described herein. For example, the present invention provides a method of fluorescence-based detection using the polymer dots herein. In some embodiments, polymers having a low density of functionalization can provide superior photophysical properties, such as high brightness for fluorescence-based detection methods. In some embodiments, polymers having a low density of functionalization can provide superior specific-cellular-targeting capabilities, such as minimal non-specific adsorption or interactions with the target cell or cellular structure or immobilized biomolecules. In some embodiments, the methods of fluorescence-based detection can include detecting light emitted from a chromophoric nanoparticle comprising a semiconducting polymer having a plurality of monomeric units, wherein less than 50% of the monomeric units present in the nanoparticle are modified with a hydrophilic moiety, and wherein at least one of the monomeric units are modified with a hydrophilic functional group suitable for conjugation. As described herein, the hydrophilic functional groups can be suitable for bioconjugation, and in some instances are stable in aqueous solution. The density of functionalization of the polymers can range as described herein. For example, the chromophoric nanoparticles can include polymers in which less than 45%, less than 40%, less than 35%, or less than 30% of the monomeric units are modified. In some embodiments, less than 25% of the monomeric units are modified. Certain embodiments include a chromophoric nanoparticle in which less than 20%, less than 15%, less than 10%, less than 5%, or less than 1% of the monomeric units are modified. The hydrophilic functional groups can include carboxylic acid or salts thereof, amino, mercapto, aldehyde, ester, hydroxyl, carbonyl, phosphate, cyanate, succinimidyl ester, and substituted derivatives thereof.

EXAMPLES

The following examples are included to further describe the present invention, and should not be used to limit the scope of the invention.

For example, a method for preparing the monovalent chromophoric polymer dot is demonstrated, a process involving the step of attachment of functionalized chromophoric dots to an engineered surface, followed by solvent washing or passivation, and then cleavage from the surface.

Example 1: Method for Preparing Functionalized Chromophoric Polymer Dots

The present example provides a method for obtaining functionalized chromophoric polymer dots for subsequent characterization and modification to monovalent chromophoric polymer dots. FIG. 3 shows chemical structures of two typical chromophoric polymers: polyfluorene terminated with carboxyl functional groups (PDHF—COOH) and polyfluorene-benzothiadiazole without functional groups (PFBT) for preparing the functionalized chromophoric polymer dots. Functionalized chromophoric polymer dots in aqueous solution are prepared as follows. First, a chromophoric polymer, for example PDHF—COOH, was dissolved in tetrahydrofuran (THF) by stirring under inert atmosphere to make a stock solution with a concentration of 0.1 mg/mL. A 5 mL quantity of the solution mixture was added quickly to 10 mL of deionized water while sonicating the mixture. The THF was removed by nitrogen stripping, and the solution was concentrated by continuous nitrogen stripping to 8 mL on a 90° C. hotplate, followed by filtration through a 0.2 micron filter. The resulting nanoparticle dispersions are clear and stable for months with no signs of aggregation.

Example 2: Method for Preparing Monovalent Single-Molecule Chromophoric Polymer Dots from Multivalent Polymer Dots The multivalent chromophoric polymer dots prepared in accordance with the above method of the present invention were modified to monovalent chromophoric polymer dots. Scheme A in FIG. 4 shows a schematic diagram for preparing monovalent single-molecule chromophoric polymer dots via an engineered particle surface. Silica colloidal beads were used in this example to provide an amine functionalized surface. But any other beads such as polymer beads, metal beads or inorganic beads can also be used. Silica colloidal particles of ~200 nm were prepared by the traditional Staber method. 100 µL of acetic acid was added to a solution of 100 mg silica particles in 5 mL MilliQ water, and magnetically stirred. Then a mixture of 10 µL of aminopropyltrimethoxysilane (APTMS) and 100 µL of Methoxy (polyethylenoxy)propyltrimethoxysilane (PEG-silane) was added to the solution, and the reaction lasted for 5 hours before a thorough washing with water to remove excess precursors. The resulting silica beads were functionalized with a high density of PEG groups and low density of amine groups, to which PDHF—COOH polymer dots can be attached catalyzed by a carbodiimide such as EDC. In a typical reaction, 20 µL of EDC (5 mg/mL in MilliQ water) was added to a mixture of PDHF—COOH polymer dots (40 µg/mL and amine-functionalized silica particles (10 mg/mL) in 20 mM HEPES buffer with a pH of 7.5. The reaction lasted for 4 hours at room temperature, and each multivalent PDHF—COOH polymer dot was associated with the silica beads by just one covalent bond because of the low-density amine groups on silica particles. Then the silica-polymer dot composite was washed thoroughly in an organic solvent such as THF so that only single PDHF—COOH molecules covalently linked with silica particle were retained on the surface. The silica particles with single PDHF—COOH molecules were redispersed in 20 mM HEPES buffer containing 1% bovine serum albumin (BSA), and then 100 mM NaOH was added to the solution to cleave the monovalent polymer dot from the silica particles.

Figure 5A:
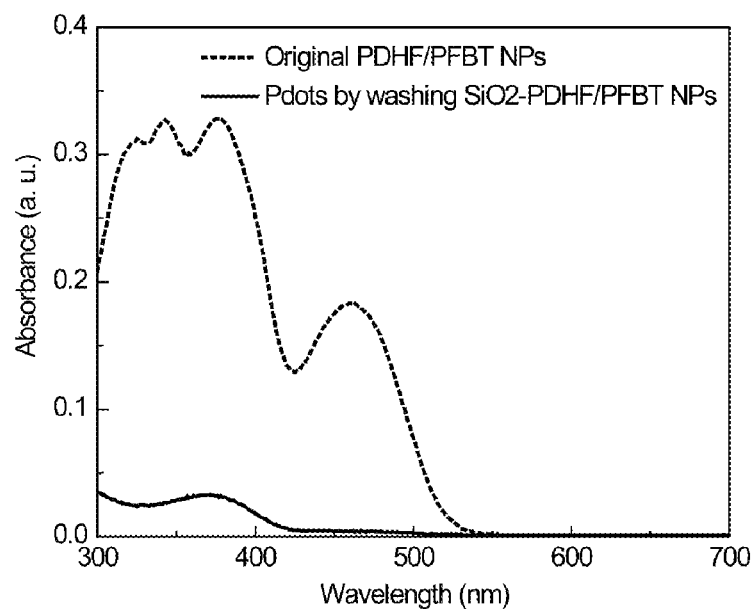
FIG. 5 (A) shows the absorption spectra change upon converting blended multivalent PFBT/PDHF—COOH polymer dots to monovalent PDHF dots, and (B) shows the fluorescence spectra change upon converting blended multivalent PFBT/PDHF—COOH polymer dots to monovalent PDHF dots, in accordance with an embodiment of the present invention.
Figure 5B:
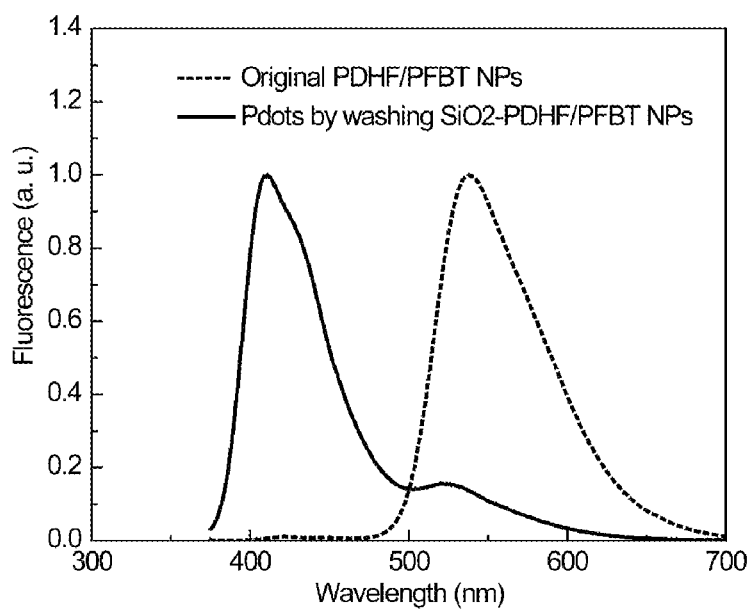

Example 3: Optical Characterization of the Formation of Monovalent Chromophoric Polymer Dots The formation of monovalent chromophoric polymer dots prepared in accordance with the method of the present invention was assessed by investigating the spectral properties and intra-particle energy transfer in blended polymer dots. UV-Vis absorption spectra were recorded with DU 720 spectrophotometer using 1 cm quartz cuvettes. Fluorescence spectra were collected with a Fluorolog-3 fluorometer using a 1 cm quartz cuvette. First, blended chromophoric polymer dots containing the same weight concentration of blue-emitting PDHF—COOH and yellow emitting PFBT polymers (chemical structures shown in FIG. 3) were prepared according to the method in Example 1. The resulting PFBT/PDHF—COOH particles have multiple carboxyl groups on surface, which can be used to conjugate with amine-functionalized silica beads. The blended polymer dots show both absorption peaks from PDHF (380 nm) and PFBT (460 nm) in the absorption spectra (FIG. 5A), but merely the yellow emission from PFBT because of efficient intra-particle energy transfer from PDHF to PFBT molecules (FIG. 5B). Monovalent polymer dots were then prepared from the blended polymer dots according to the method in Example 2. As can be seen in FIG. 5A, the absence of PFBT absorption indicates that solvent washing efficiently removes the unconjugated PFBT molecules from the polymer dots so that only those PDHF—COOH molecule covalently bound to the silica surface were retained to form monovalent polymer dots. As an additional confirmation, the monovalent dots present characteristic emission from PDHF—COOH (FIG. 5B).

Example 4: Optical Properties of the Monovalent Chromophoric Polymer Dots

Figure 6A:
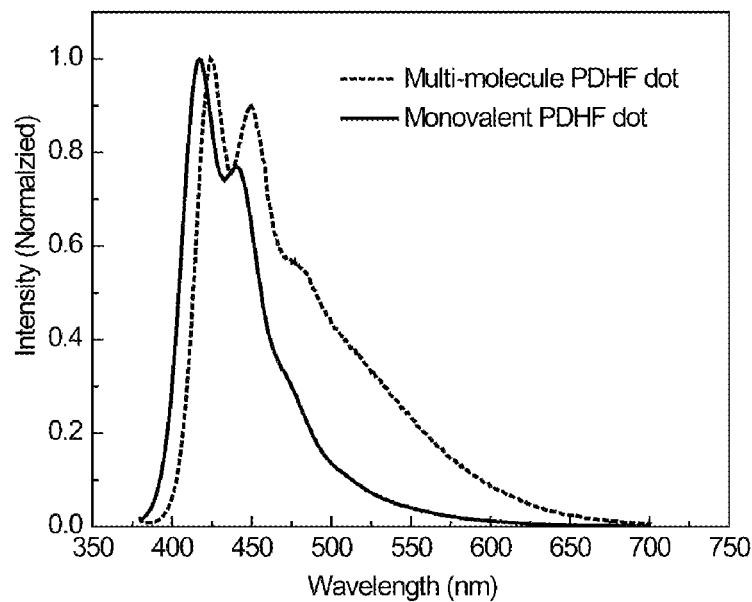
FIG. 6 (A) shows the emission spectral shift upon modifying multivalent PDHF—COOH polymer dots to monovalent dots, and (B) shows the fluorescence quantum yield increase of monovalent PDHF—COOH dots as compared to the multivalent ones, in accordance with an embodiment of the present invention.
Figure 6B:
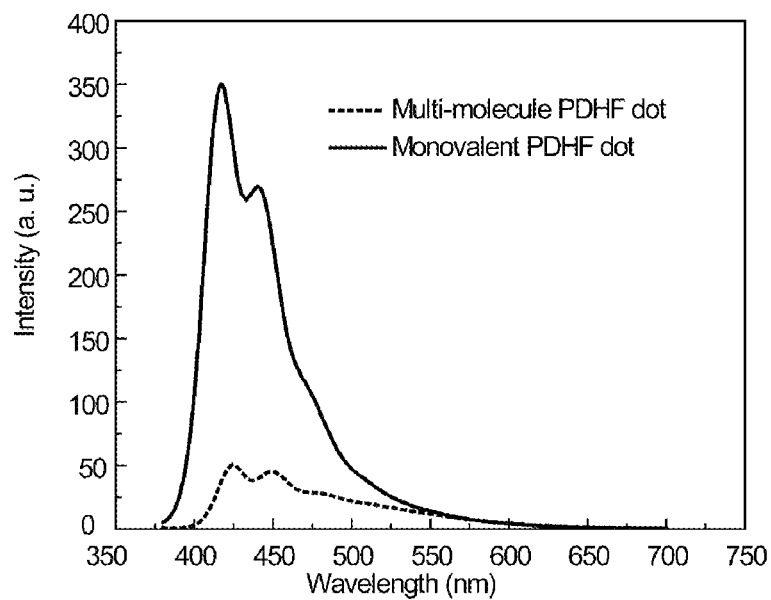

The optical properties of monovalent chromophoric polymer dots prepared in accordance with the method of the present invention were assessed by UV-vis and fluorescence measurements. UV-Vis absorption spectra were recorded with DU 720 spectrophotometer using 1 cm quartz cuvettes. Fluorescence spectra were collected with a Fluorolog-3 fluorometer using a 1 cm quartz cuvette. The monovalent PDHF—COOH polymer dots exhibit similar absorption, but blue-shifted emission spectra as compared to those of chromophoric polymer dots containing multiple PDHF—COOH molecules (FIG. 6A). This is consistent with the photophysical picture: the presence of low-energy species, defects, and aggregates in multimolecule polymer dots cause red-shifted fluorescence. As seen in FIG. 6B, the blue-shifted fluorescence of monovalent PDHF—COOH dots is accompanied by the increase of fluorescence quantum yield, which is also consistent with the absence of aggregates and reduced number of defects.

Example 5: Synthesis of PFBT Polymers with Varied Density of Side-Chain Functionalizations The examples provided herein indicate that the density of side-chain functional groups can, in some cases, significantly affect internal particle structure, colloid stability, fluorescence brightness, and non-specific labeling of the chromophoric polymer dots in biological applications. This example describes the synthesis of a series of PFBT polymers functionalized with carboxylic acid groups in the side chains with molar fractions from 50% to 2.3% (FIG. 8). As shown, n is the number of repeating structural units present in the polymer, as described herein. Ratios of the different monomers in the polymer can be described in terms of x, y and z, which add up to 1. As provided in this example, z corresponds to the monomer unit providing functional groups. The ratio of this monomer can be varied to produce polymers having varied functionalization densities, as described further herein (e.g., less than about 50%, less than about 25%, or less than about 5%).

PFBT polymer was chosen because of its high brightness and absorption peak convenient for fluorescence microscopy and laser excitations. Carboxylate-functionalized PFBT were synthesized by co-polymerization of 9,9-dioctylfluorene-2,7-diboronic acid bis(1,3-propanediol) ester, 4,7-dibromobenzo[c][1,2,5]thiadiazole, and 2,7-dibromo-9,9-bis(3-(tert-butyl propanoate))fluorene, followed by removal of protecting tert-butyl groups using trifluoroacetic acid. The presence of —COOH in polymers was further confirmed by IR spectra (FIG. 16). The molar fraction of carboxylic acid groups in polymer chains can be tuned by changing the feed ratios of monomers in the synthesis step, which was further verified by $^1$HNMR data (comparing the integration of protons in $C_8H_{17}$ alkyl chains and tert-butyl groups before treating with TFA). In this work, polymers functionalized with 2.3%, 14%, and 50% (hereafter abbreviated as PFBT-C2, PFBT-C14, and PFBT-C50 respectively) of carboxylic acid groups were investigated. Similarly, amine-functionalized PFBT polymers with controlled molar fraction of —NH$_2$ were also synthesized. Gel permeation chromatography (GPC) analysis revealed that the molecular weights of all of the polymers are in the range of 12-20 kg/mol.

The synthesis of monomers in this example is as follows. A mixture of 2,7-dibromofluorene (15 mmol, 4.86 g), tert-butyl 3-bromopropanoate (33 mmol, 6.86 g), sodium hydroxide solution (40%, 35 mL), Bu$_4$NBr (1.5 mmol, 0.48 g), toluene (70 mL) was stirred at 85° C. overnight. The organic phase was separated, washed with water and dried over MgSO$_4$. After evaporation of the solvent, the residue was purified by column chromatography (DCM). The product was obtained as a white solid. Yield: 4.81 g, 83%. $^1$HNMR (500 MHz, CDCl$_3$): δ=7.47-7.54 (m, 6H), 2.30 (t, 4H), 1.47 (t, 4H), 1.33 (s, 18H). $^{13}$CNMR (500 MHz, CDCl$_3$): 172.71, 150.47, 139.60, 131.56, 126.99, 122.57, 121.93, 80.97, 54.58, 34.92, 30.36, 28.52.

Polymers in this example were synthesized by copolymerization of monomers 2,7-dibromo-9,9-bis(3-(tert-butyl propanoate))fluorene (A), 4,7-dibromobenzo[c][1,2,5]thiadiazole (B), 9,9-dioctylfluorene-2,7-diboronic acid bis(1,3-propanediol) ester (C) by Suzuki Coupling with different monomer feed ratios. PFBT-C2 was used as an example here: In a 100 mL flask, monomer A (0.06 mmol, 34.8 mg), B (0.94 mmol, 276.2 mg), C (1 mmol, 558.4 mg), was dissolved in toluene (20 mL), Bu$_4$NBr (0.04 mmol, 12.5 mg) and Na$_2$CO$_3$ (2M, 12 mL) was added. The mixture was degassed and refilled with N$_2$ (repeated 4 times) before and after addition of Pd(PPh$_3$)$_4$ (0.035 mmol, 40 mg). The reactants were stirred at 90° C. for 40 hours and phenylboronic acid (100 mg) dissolved in THF (1 mL) was added. After two hours, bromobenzene (1 mL) was added and further stirred for 3 hours. The mixture was poured into methanol (200 mL). The precipitate was filtered, washed with methanol, water, and acetone to remove monomers, small oligomers, and inorganic salts. The crude product was dissolved in DCM (15 mL), filtered through 0.2 m membrane and re-precipitated in methanol (150 mL). The powder was then stirred in acetone (200 mL) overnight and collected by filtration, and dried in vacuum. Yield: 413 mg (72%). $^1$HNMR (500 MHz, CDCl$_3$): δ=7.90-8.20 (m, 8H), 2.00-2.30 (broad, 4H), 1.32 (s, 0.86H), 1.08-1.26 (m, 20H), 0.96 (broad, 4H), 0.81 (t, d=6 Hz, 6H). The protecting tert-butyl esters group was removed by TFA at room temperature. Trifluoroacetic acid (3 mL) was added into a solution of polymer (200 mg) in DCM (60 mL) and stirred overnight. The organic layer was washed with water (100×3) and then stirred with NaOH solution (10%, 30 mL) for 10 minutes. The mixture was then acidified with acetic acid. The DCM phase was washed with water and concentrated to 10 mL and precipitated in methanol (100 mL). The final powder was collected by filtration, washed with acetone, and dried in vacuum.

Example 6: Preparation and Characterization of PFBT Dots with Varied Density of Side-Chain Functionalizations The chromophoric polymer dots were prepared from the three polymers (PFBT-C2, PFBT-C14, and PFBT-C50 respectively) synthesized above by using the reprecipitation method. PFBT-C2 dots were prepared by injecting 2 mL (100 ppm) THF stock solution of PFBT-C2 polymer into 10 mL H$_2$O under sonication. PFBT-C14 Pdots were prepared by injecting 2 mL (100 ppm) THF stock solution of PFBT-C14 polymer into 10 mL H$_2$O under sonication. PFBT-C50 were prepared by injecting 400 μL (500 ppm) THF stock solution of PFBT-C50 polymer into 10 mL H$_2$O under sonication. By tuning the starting concentration particle sizes of these three polymers was controlled to 21 nm, for reliable comparisons of their properties. The particle sizes were investigated by transmission electron microscopy (TEM) and dynamic light scattering (DLS). Representative TEM and DLS data are shown in FIG. 9. Dynamic light scattering (DLS) measurement results show that PFBT-C2, PFBT-C14 and PFBT-C50 Pdots have the same average size of 21 nm.

$^1$HNMR and $^{13}$CNMR spectra were recorded on a bruker AV500 spectrometer. IR spectra were collected on a Bruker vector 33 Frourier transform infrared spectrophotometer (using KBr pellets) in the range 400-4000 cm$^{-1}$. The particle size and zeta-potentials of Pdots in bulk solution was characterized by dynamic light scattering (Malvern Zetasizer NanoS). For the TEM measurements, one drop of the Pdot dispersion was placed on a carbon-coated copper grid. After evaporation of the water, the nanoparticles were imaged with a transmission electron microscope (FEI Tecnai F20). UV-Vis absorption spectra were recorded with a DU 720 scanning spectrophotometer (Beckman Coulter, Inc., CA USA) using 1 cm quartz cuvettes. Fluorescence spectra were obtained using a commercial Fluorolog-3 fluorometer (HORIBA Jobin Yvon, NJ USA). Fluorescence quantum yields were measured using a Hamamatsu photonic multichannel analyzer C10027 equipped with CCD integrating sphere. For the measurement of single particle fluorescence brightness, fluorescent samples were diluted in Milli-Q water, dried on cleaned glass coverslips (previously functionalized with (3-aminopropyl)trimethoxysilane (APTMS)), and imaged on a customized wide-field epifluorescence microscope described as follows. The 488-nm laser beam from a sapphire laser (Coherent, Santa Clara, CA USA) was directed into an inverted microscope (Nikon TE2000U, Melville, NY, USA) using lab-built steering optics. Laser excitation power was measured at the nosepiece before the objective. The objective used for illumination and light collection was a Nikon CFI Plan Fluor 100XS Oil (with iris) objective with 100× magnification and 0.5-1.3 N.A (Nikon, Melville, NY, USA). Fluorescence signal was filtered by a 500-nm long pass filter (HQ500LP; Chroma, Rockingham, VT, USA) and imaged on an EMCCD camera (Photometrics Cascade: 512B, Tucson, AZ USA). Fluorescence intensity of Pdot particles was back-calculated according to the attenuation factor. Fluorescence intensity emitted per frame for a given particle was estimated by integrating the CCD signal over the fluorescence spot.

Figures 10A, 10B:
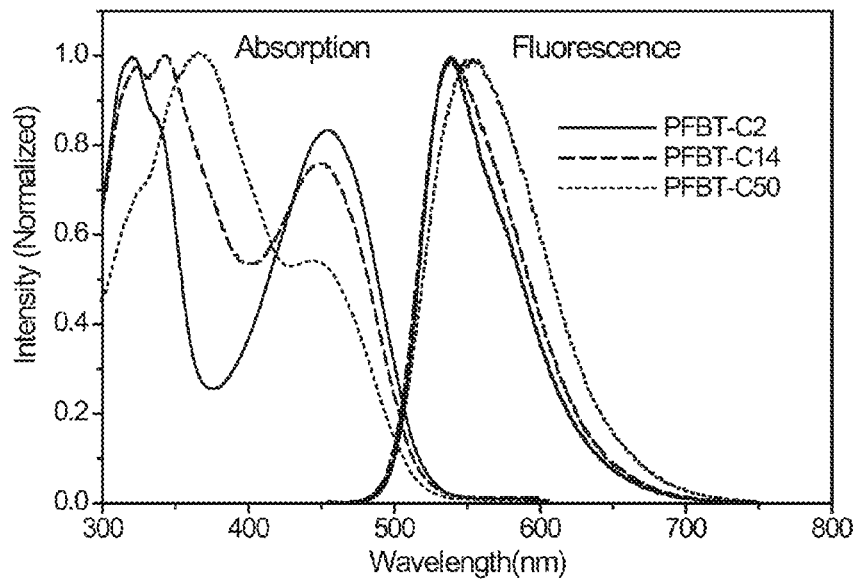
FIG. 10A shows absorption and fluorescence spectra of PFBT dots with different density of side-chain functional groups, and 10B shows particle sizes, zeta potential and photophysical properties of Pdots prepared from PFBT polymers with different density of carboxylic acid groups, in accordance with some embodiments of the present invention
Figure 11A:
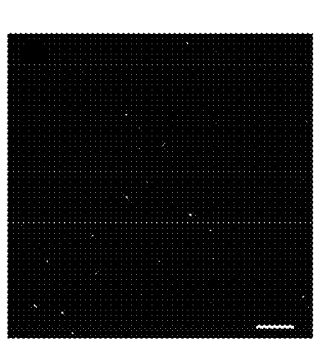
FIGS. 11A-F shows typical single-particle fluorescence images of (A) PFBT-C2, (B) PFBT-C14, and (C) PFBT-C50 Pdots, obtained under identical excitation and collection conditions. The bottom panel shows intensity distribution histograms for single-particle fluorescence brightness: (D)
Figure 11B:
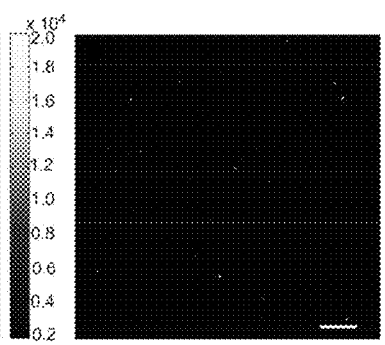
Figure 11C:
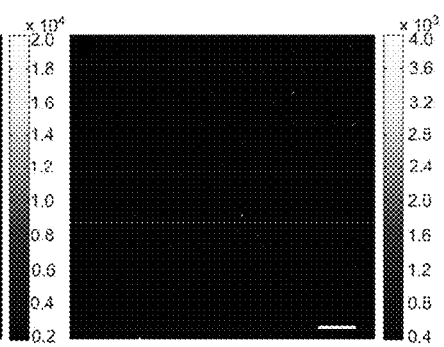
Figure 11D:
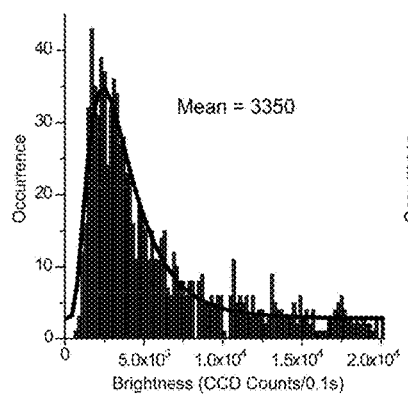
Figure 11E:
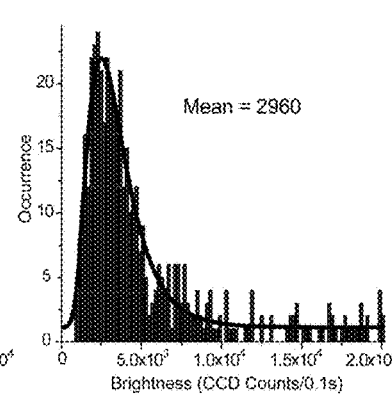
Figure 11F:
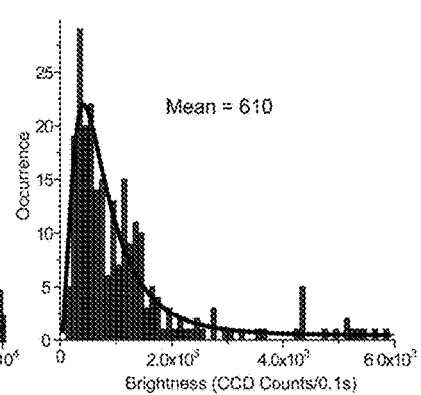

Example 7: Fluorescence Brightness of PFBT Dots with Varied Density of Side-Chain Functionalizations Absorption and fluorescence spectroscopy were performed to investigate the optical properties of the Pdots with different molar fractions of side-chain carboxylic acid groups. As indicated in FIG. 10A, the three Pdots exhibit different absorption peak and intensities in their absorption spectra because of the monomer functionalization and the difference in monomer feeding ratio for polymer synthesis. In addition, the functionalization density in the polymers side chains show obvious influence on the fluorescence spectra of the resulting Pdots. As compared to PFBT-C2 and PFBT-C14 dots, the PFBT-C50 dots exhibit a highly redshifted and broadened fluorescence spectrum. This property is consistent with the observation in the conjugated polyelectrolytes, which have the same PFBT backbone and show similar redshift and broadening in emission spectra because of the high density of ionic moiety in their side-chains. Another negative effect caused by high density functionalization is the reduction in fluorescence quantum yield (FIG. 10B). The quantum yield of the PFBT-C50 dots was measured to be ~0.17, much lower than that of the PFBT-C2 (~0.30) and PFBT-C14 dots (~0.23). Again, this trend is similar to a general fact in conjugated polyelectrolytes, in which the side chain ionic moieties usually result in quenched emissions as compare to their hydrophobic counterparts. Because the high density of functionalization can yield disadvantages such as the emission peak broadening and quantum yield reduction, low density of functionalization is favorable with regard to the probe performance in biological applications.

Fluorescence brightness is defined as the product of absorption cross-section and fluorescence quantum yield. The absorption cross-section per particle can be estimated according to the absorption spectra. Assuming each of the three Pdots have the same packing density of fluorophores (i.e. the number of PFBT molecules per particle), their absorption cross-sections were estimated to be on the order of magnitude of $10^{-13}$ $cm^2$ (FIG. 10B), Further considering the quantum yields, the per-particle fluorescence brightnesses of PFBT-C2 and PFBT-C14 dots are calculated to be 4.1 and 2.7 times higher than PFBT-C50 dots, respectively. In order to investigate the single particle brightness, single-particle brightness measurements were performed using single particle fluorescence microscopy.

FIG. 11 shows the single-particle fluorescence images of the three Pdots under identical excitation and collection conditions. Intensity histograms were obtained by statistical analyses of thousands of particles, as shown in the bottom panel of FIG. 11. As shown in FIG. 11, the measured per-particle brightness of PFBT-C2 dots and PFBT-C14 dots are 5.5 and 4.9 times, respectively, higher than PFBT-C50 dots. The calculated intensity ratio (4.1 times) of PFBT-C2 relative to PFBT-C50 dots from bulk spectroscopy are lower than the measured intensity ratios (5.5 times) from single-particle imaging, indicating the calculated per-particle brightness in PFBT-C50 dots is overestimated as compared to the actual number of PFBT molecules per particle. Similarly, the calculated intensity ratio (2.7 times) of PFBT-C14 relative to PFBT-C50 dots is also lower than the actual measured ratio (4.9 times) from single-particle imaging. These discrepancies indicate that the actual chromophore packing density in PFBT-C50 dots are lower than those in PFBT-C2 and PFBT-C14 dots.

Example 8: Stability and Internal Structure of PFBT Dots with Varied Density of Side-Chain Functionalizations In some embodiments, two aspects can be used to describe the stability of nanoparticles: one is whether the nanoparticles are stable against aggregation (i. e. forming large particles); the other is whether the nanoparticles are stable against dissociation (i. e. producing small molecules/particles by decomposition). One aspect related to aggregation is the ξ-potential of the polymer dots. The surface charge of the resulting Pdots was analyzed by ξ-potential measurements. ξ-potential of PFBT-C2, PFBT-C14 and PFBT-C50 Pdots are measured to be −50.2, −54.4, and −57.5 mV, respectively (FIG. 10). Nanoparticle stability is also strongly dependent on whether the nanoparticles are easily dissociated or decomposed over time. Because the Pdot formation is primarily driven by hydrophobic interactions, hydrophilic side-chains can have significant interferences with the association strength among different portions of a polymer chain or between polymer chains, thus affecting the nanoparticle stability and performance. For example, loose aggregates, rather than stable and compact particles, are formed when preparing nanoparticles from polymers with heavily functionalized hydrophilic side-chains, and their aggregation nature is affected by many factors such as polymer concentrations, ionic strength, and temperature.

Figure 12A:
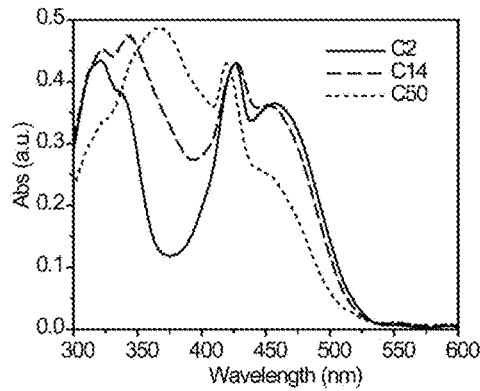
Figure 12D:
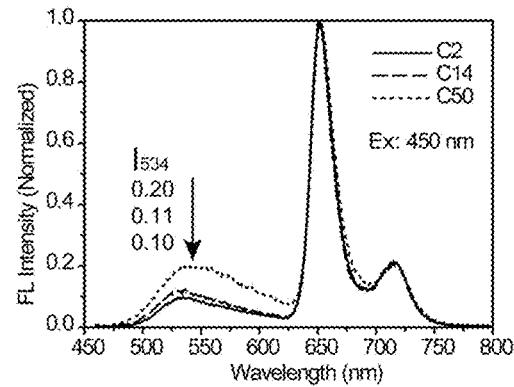
Figure 12B:
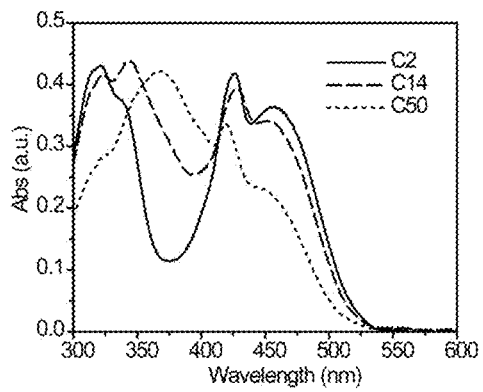

This example investigates the stability and internal structure of polymer dots prepared from the three polymers: PFBT-C2, PFBT-C14 and PFBT-C50. A dye-doping and leaching method was used to examine the different internal structures of the polymer dots. The samples of three dye-doped polymer dots were prepared by co-precipitation method and all of the dye-doped Pdots have the similar particle size of 18 nm in diameter. Tetraphenylporphyrin (TPP) dye was chosen as the acceptor to investigate the internal structures of PFBT-C2, PFBT-C14, and PFBT-C50 Pdots. There is efficient Förster resonance energy transfer (FRET) between the polymer host and the TPP dye dopant, therefore the FRET efficiency is reflective of the internal structures of the three polymer dots. In this method, TPP dye was doped into host polymer dots with a doping concentration of 5 wt %. The centrifugal filtration was used to separate the retained polymer dots and the filtrate containing TPP dye leaching out from the polymer dots. Spectroscopic changes in the polymer dots before and after centrifugal filtration should be observed when obvious leaching occurs. The absorption and fluorescence spectra of TPP-doped Pdot solutions were measured before (FIG. 12A) and after centrifugal filtration (FIG. 12B). A clear decrease in absorbance was observed for TPP-doped PFBT-C50 dots after centrifugal filtration due to material loss. As further shown in FIG. 12C, the filtrate from PFBT-C50 dots contains a significant amount of TPP dyes as well as a large portion of PFBT-C50 molecules. Quantitative analyses show that about 10% of PFBT and 50% of TPP molecules were leached out from PFBT-C50 dots, but no PFBT and only 6% of TPP were leached out from PFBT-C2 dots. This indicates that the PFBT-C50 dots are partially dissociated (or decomposed), because the high density of hydrophilic side-chains can solvate the polymer molecules in aqueous solution. In contrast, in the PFBT-C2 and PFBT-C14 dots, the PFBT dissociation and the TPP leaching are greatly reduced with decreasing the density of side-chain hydrophilic functional groups, which indicate a stronger association in PFBT-C2 dots through hydrophobic interactions as compared to PFBT-C14 and PFBT-C50 dots with higher density of hydrophilic functional groups.

Figure 12E:
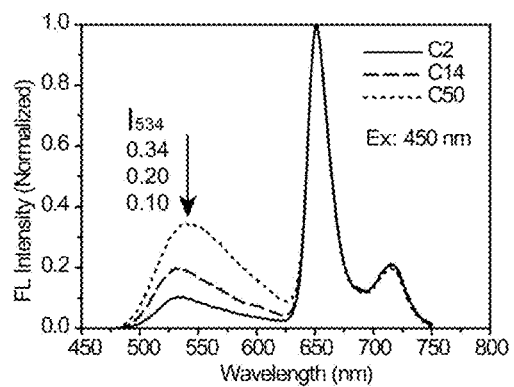
Figure 12C:
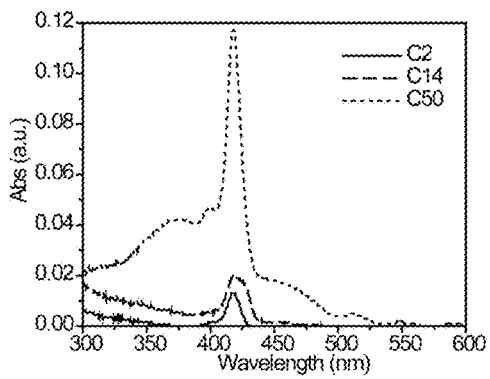
Figure 12F:
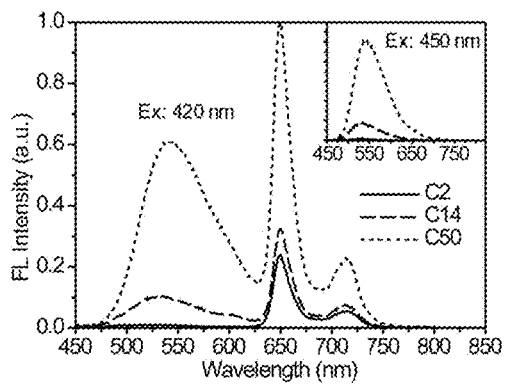
Figure 13A:
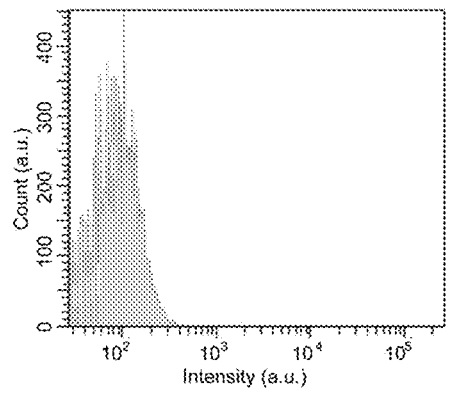
Figure 13B:
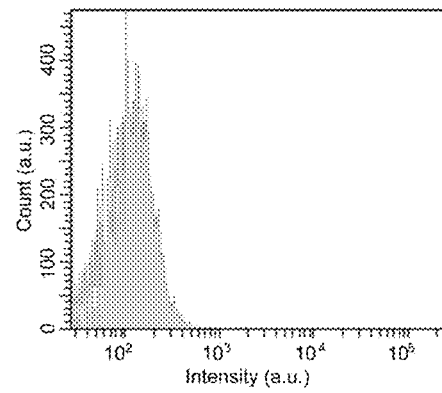
Figure 13C:
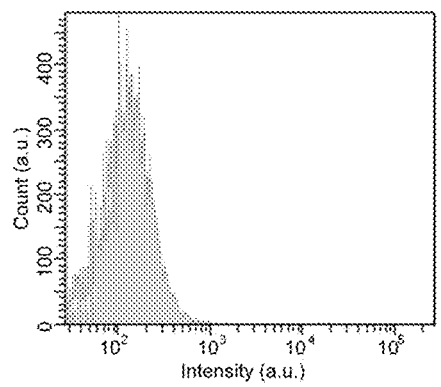
Figure 13D:
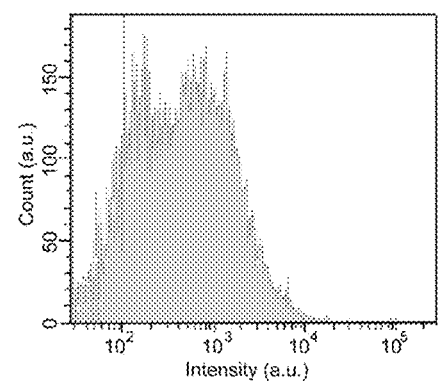

Fluorescence spectra further confirm the different internal structure in the three dye-doped PFBT dots. In order to conveniently compare the difference among the fluorescence spectra, all the fluorescence spectra were normalized according to emission peak of the TPP emitters. FIGS. 12D and 12E show that the intensity ratio of fluorescence peaks for the TPP acceptor to PFBT donor is increased with decreasing the density of carboxylic acid groups, which indicates that the FRET is more efficient in PFBT-C2 dots as compared to PFBT-C14 and PFBT-C50 dots. The higher FRET efficiency is indicative of short distance between donor and acceptors, and therefore a more compact internal structure in PFBT-C2 dots as compared to PFBT-C14 and PFBT-C50 dots. FIGS. 12D to 12E show that the ratio of PFBT donor to TPP acceptor in PFBT-C14 and PFBT-C50 dots are increased after centrifugal filtration, which indicates that some TPP acceptors have been leached out from the polymer dots. FIG. 12F shows the fluorescence changes of the filtrate, which further confirmed that TPP leaching and PFBT dissociation in the polymer dots are strongly dependent on the density of side-chain functionalization with hydrophilic functional groups. The emission in FIG. 12F show that PFBT molecules significantly leached out from PFBT-C50 dots, and nearly no leaching occurs for PFBT-C2 dots. Overall, the dye leaching and Pdot dissociation is increased with increasing the density of hydrophilic functional groups in the polymer side-chains because of the fact that polymers with low density functionalization can form stable and compact polymer dots while those with high density functionalization tend to yield unstable and loose particles. Therefore, low density of functionalization with hydrophilic functional groups is important for developing the Pdot technology for further biological applications.

Example 9: Nonspecific Cellular Labeling of PFBT Dots with Varied Density of Side-Chain Functionalizations When polymer dots are used for fluorescent labeling, their nonspecific binding properties are important. In this example, flow cytometry was performed to evaluate the nonspecific labeling of the PFBT-C2, PFBT-C14, and PFBT-C50 dots.

For the flow cytometry experiment, the breast cancer cell line MCF-7 was ordered from American Type Culture Collection (ATCC, Manassas, VA, USA). Cells were cultured at 37° C., 5% $CO_2$ in Eagles minimum essential medium supplemented with 10% Fetal Bovine Serum (FBS), 50 U/mL penicillin, and 50 μg/mL streptomycin. The cells were pre-cultured prior to experiments until confluence was reached. The cells were harvested from the culture flask by briefly rinsing with culture media followed by incubation with 5 mL of Trypsin-EDTA solution (0.25 w/v % Trypsin, 0.53 mM EDTA) at 37° C. for 5-15 minutes. After complete detachment, the cells were rinsed, centrifuged, and resuspended in 1×PBS buffer. The cell concentration was determined by microscopy using a hemacytometer. Cells were fixed by rinsing with 4% (v/v) paraformaldehyde solution followed by two washing steps with labeling buffer (1×PBS, 2 mM EDTA, 1% BSA). For nonspecific cell labeling with Pdots, a million cells in 100 μL labeling buffer was incubated with corresponding Pdots (21 nm in diameter, 25 nM in BlockAid™ blocking buffer from Invitrogen) on a rotary shaker for 30 minutes in the dark at room temperature, followed by two washing steps using labeling buffer. Cells were then suspended in 1 mL labeling buffer for flow cytometry. Flow cytometry was operated on a BD FACS Canto flow cytometer (BD Biosciences, San Jose, CA, USA). A 488 nm laser was used for excitation and emission was collected through FITC channel equipped with a 520 nm long-pass filter and a 530/30 nm band-pass filter. Data was analyzed using the FACSDival software.

FIG. 13 shows the flow cytometry results: 13a shows cells without incubation with polymer dots, 13b, 13c, and 13d show the cells incubated with PFBT-C2, PFBT-C15, and PFBT-C50 dots, respectively. The fluorescence intensity of the cells incubated with PFBT-C2 Pdots is comparable than that of unlabeled cells, indicating little nonspecific labeling of the PFBT-C2 dots. The PFBT-C14 show a little higher intensity than PFBT-C2 dots, whereas the PFBT-C50 Pdots exhibit significant nonspecific labeling, at least 5 times higher than that of PFBT-C2 and PFBT-C14 Pdots. These results strongly indicates that Pdots with high density of functional groups yield strong nonspecific labeling in biological applications as compared to those Pdots with low density of functional groups. This is also consistent with their structures because PFBT-C50 dots with loose structure have high surface area, resulting in strong nonspecific interaction as compare to the compact PFBT-C2 and PFBT-C14 dots.

Example 10: Bioconjugation and Specific Cellular Labeling Using PFBT-C2 Dots

To evaluate the carboxylate functionalized Pdots for biological imaging, bioconjugation with streptavidin (SA) was performed for specific targeting to cell surface receptors. Because polymer dots with low density of functional groups show much improved properties in terms of stability, fluorescence brightness, internal structure, and nonspecific properties, PFBT-C2 dots were chosen as the example to demonstrate the bioconjugation and specific cellular labeling. Based on the $^1$HNMR data and molecular weight (Mn=13 kg/mol, Mw/Mn=1.4), each molecule of the PFBT-C2 polymer chain roughly has one functional monomer, which is the carboxylate functionalized 9,9-bis(3-propanoic acid)fluorene (with two —COOH groups). Such low density of functional group was effective enough for bioconjugations and specific cellular labeling.

Streptavidin is used ubiquitously because of its remarkable binding affinity to biotin. As Pdots of PFBT-C2 exhibit the best brightness, lowest density of carboxylate groups, and least non-specific adsorption with cell surface, herein PFBT-C2 Pdots were used to study the conjugation with biomolecules. PFBT-C2 Pdots were mixed with streptavidin in a HEPES buffer (20 mM, pH=7.4) solution containing 0.1 wt % polyethylene glycol (PEG, MW3350). The peptide bond formation between the carboxyl groups on Pdots and the amine groups of streptavidin was catalyzed by 1-ethyl-3-[3-dimethylaminopropyl]carbodiimide hydrochloride (EDC). However, due to the intrinsically hydrophobic nature of the Pdots, biomolecules tend to nonspecifically adsorbed onto the particle surface. Even in the presence of PEG, the functionalized Pdots physically mixed with streptavidin can still bind to the biotinylated cell surface, while the Pdots without streptavidin do not show binding. Another observed problem was that the functionalized Pdots stuck to size exclusion gels, which makes the subsequent purification troublesome.

To overcome these nonspecific adsorptions, Triton X-100 and bovine serum albumin (BSA) was introduced to reduce the adsorption and block the particle surface after 2 hours of the bioconjugation with streptavidin. This step can successfully overcome the nonspecific adsorption on Pdots. The mixture was also smoothly filtered through a size exclusion column to remove free streptavidin, additives, and small molecules. The final streptavidin conjugated Pdots was used to label specific cellular target, Her2, target of the anti breast cancer drug, Heceptin for cancer treatment. SKBR3 breast cancer cells were successively incubated with primary anti-Her2 antibody, biotinylated goat anti-mouse IgG secondary antibody, and PFBT-C2-SA. As shown in FIG. 14A, PFBT-C2-SA probes, effectively labeled Her2 receptors on the cell surface. In two control experiments, where the catalyst EDC or the streptavidin were absent, no fluorescence on the cell surface was detected (FIG. 14B), confirming that the bioconjugation of streptavidin to Pdots was covalent and the cellular labeling was specific through biotin-streptavidin interaction. Another control experiment was performed, in which the cells were incubated with primary antibody and PFBT-C2-SA probes in the absence of biotin anti-mouse IgG. The result also showed that no fluorescence was observed on cell surface, indicating the highly specific binding of PFBT-C2-SA. The lack of signal also indicated the absence of nonspecific binding in this biotin-streptavidin labeling system. The Pdots-SA maintained long-term colloidal stability. Owing to the stable covalent coupling between Pdots and biomolecules, the labeling efficiency of Pdots-SA remains unchanged after different concentration and purification processes such as centrifugation, ultrasonication, and gel filtration.

Besides the formation of functionalized nanoparticles of the polymer itself, the PFBT-C2 polymer can also be blended with hydrophobic polymers to functionalize a variety of Pdots of different polymers. Most fluorescent hydrophobic polymers commercially available do not have functional groups. This strategy utilizes the large number of existing semiconducting polymers, which can yield a vast color library of functionalized nanoparticle labels. Moreover, energy transfer in the blended Pdots resulted in highly red-shifted emission in deep-red or near infrared region, an appealing feature for in vivo applications. We used PFBT-C2 to functionalize a (fluorene-dithienylbenzothiadiazole-based polymer (PFTBT), which exhibit bright solid-state fluorescence in the deep-red region. Bright red-emitting Pdots were prepared by co-condensation of PFBT-C2 and PFTBT polymers (weight ratio of 3:2). As the emission band of PFBT-C2 overlap well with the absorbance of PFTBT, efficient energy transfer from PFBT-C2 to PFTBT was achieved in these blended Pdots. In addition, the peak separation between excitation and emission based on FRET (170 nm) is much larger than that of PFBT-C2 (80 nm), which is favorable for reducing background noise due to excitation.

Due to the very low molar fraction of carboxylate groups, PFBT-C2 is highly hydrophobic in nature and mixed well with PFTBT polymer in blended particles. The efficient energy transfer and optical property of final Pdots do not change after several months. As the carboxylate groups exist randomly in the polymer chains, they are also likely to be located on the particle surface of Pdots. Because PFTBT polymer does not have functional groups, the carboxylate groups per particle in the PFBT-C2/PFTBT blended Pdots is 40% less than that in the pure PFBT-C2 dots. Similar bioconjugations were performed, and the results showed that such low density of functional group was effective enough for bioconjugations and specific cellular labeling. The final red blended Pdots-SA probes, together with primary anti-Her2 antibody and biotinylated goat anti-mouse IgG secondary antibody, also effectively labeled Her2 receptors on SKBR3 cell surface (FIG. 14C), whereas the control samples do not show labeling.

Example 11: Functional Modification of Polymer Side-Chains for Bioorthogonal Labeling This example shows that the carboxylate functionalized polymer can provide a useful scaffold that can be flexibly modified with functional small molecules for versatile applications. This example presents the ability to obtain clickable alkyne-functionalized PFBT polymer by reacting the carboxylate side-chain with propargylamine. Other amine-containing molecules can also be used to obtain different functionalities. These alkyne-bearing probes are particularly suitable for click chemistry-based bioorthogonal labeling, a powerful approach for cellular labeling with very low background. Alkyne-functionalized PFBT polymer (PFBT-C14A) was prepared by reaction between PFBT-C14 and propargylamine in THF using N,N'-dicyclohexylcarbodiimide (DCC) as catalyst. The presence of low density of —NH and —C≡CH was confirmed by the weak signal in $^1$HNMR spectrum. In this work, the number of alkyne groups in one polymer chain was estimated as about 1.5 by comparing the proton integrations of $C_8H_{17}$ alkyl chains and —C≡CH groups. Alkyne functionalized Pdots was prepared by reprecipitation method using the PFBT-C14A as polymer precursor, and the resulting Pdots can be directly applied for bioorthogonal labeling of cellular targets. MCF-7 cells were incubated with N-azidoacetylgalactosamine (GalNAz) for three days in order to enrich O-linked glycoproteins with the azido groups. The GalNAz-treated cells were tagged with alkyne Pdots via click reaction, and bright cell-surface labeling was observed for the cells positively labeled with alkyne Pdots (FIG. 15). In control experiment in which PFBT-C14 (without alkyne) was used, labeling of cell surface was not detected (FIG. 15B). This confirms that labeling is achieved by copper(I)-catalyzed cycloaddition between alkyne groups on Pdots surface and azide groups in glycoproteins on cell surface.

While this invention has been described with an emphasis on preferred embodiments, it will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with the true scope and spirit of the invention being defined by the following claims.

What is claimed is:

1. A chromophoric nanoparticle comprising:
chromophoric semiconducting polymer comprising a plurality of hydrophilic functional groups covalently bound to the chromophoric semiconducting polymer at two or more termini of the chromophoric semiconducting polymer.

2. The chromophoric nanoparticle of claim 1, wherein the chromophoric semiconducting polymer comprises a polymer backbone and the chromophoric semiconducting polymer does not comprise triple bonds in the polymer backbone.

3. The chromophoric nanoparticle of claim 1, wherein hydrophilic functional groups of the plurality of hydrophilic functional groups are independently selected from the group consisting of carboxylic acid or salts thereof, amino, mercapto, aldehyde, ester, carbonyl, phosphate, cyanate, succinimidyl ester, maleimide, and substituted derivatives thereof.

4. The chromophoric nanoparticle of claim 1, wherein hydrophilic functional groups of the plurality of hydrophilic functional groups include a carboxyl group.

5. The chromophoric nanoparticle of claim 1, wherein a hydrophilic functional group of the plurality of hydrophilic functional groups is attached to a surface of the chromophoric nanoparticle via a linker moiety.

6. The chromophoric nanoparticle of claim 5, wherein the linker moiety comprises polyethylene glycol.

7. The chromophoric nanoparticle of claim 1, wherein the plurality of hydrophilic functional groups is stable in an aqueous solution.

8. The chromophoric nanoparticle of claim 1, wherein the plurality of hydrophilic functional groups is suitable for bioconjugation.

9. The chromophoric nanoparticle of claim 1, wherein the chromophoric nanoparticle is further covalently conjugated to a biological molecule selected from a protein, a nucleic acid, a carbohydrate, and a peptide.

10. The chromophoric nanoparticle of claim 1, the chromophoric nanoparticle is further covalently conjugated to a biological molecule selected DNA and RNA.

11. The chromophoric nanoparticle of claim 1, the chromophoric nanoparticle is further covalently conjugated to an antibody.

12. The chromophoric nanoparticle of claim 1 wherein the semiconducting chromophoric polymer comprises a plurality of monomeric units, wherein less than 50% of monomeric units of the plurality of monomeric units present in the chromophoric nanoparticle are covalently modified with the two or more hydrophilic functional groups.

13. The chromophoric nanoparticle of claim 12, wherein less than 30%, less than 25%, less than 15%, less than 10%, or less than 7% of the monomeric units are covalently modified with the two or more hydrophilic functional groups.

14. The chromophoric nanoparticle of claim 1, wherein the chromophoric nanoparticle comprises a blend of semiconducting polymers including the semiconducting chromophoric polymer.

15. The chromophoric nanoparticle of claim 1, wherein the chromophoric nanoparticle comprises a blend of semiconducting polymers including the semiconducting chromophoric polymer and non-semiconducting polymers.

16. The chromophoric nanoparticle of claim 1, wherein the plurality of hydrophilic functional groups is present only on the two or more termini of the chromophoric semiconducting polymer.

17. The chromophoric nanoparticle of claim 1, wherein the chromophoric nanoparticle further comprises hydrophilic groups covalently bonded to sidechains of the semiconducting chromophoric polymer.

18. The chromophoric nanoparticle of claim 1, wherein the chromophoric nanoparticle comprises 2, 3, 4, 5, 6, 7, 8, 9, 10, or more hydrophilic functional groups.

19. The chromophoric nanoparticle of claim 1, wherein hydrophilic functional groups of the plurality of hydrophilic functional groups have different reactivities.

20. A composition comprising a plurality of chromophoric nanoparticles according to claim 1.

* * * * *

UNITED STATES PATENT AND TRADEMARK OFFICE
CERTIFICATE OF CORRECTION

Page 1 of 1

PATENT NO. : 12,216,124 B2
APPLICATION NO. : 18/058458
DATED : February 4, 2025
INVENTOR(S) : Daniel T. Chiu et al.

It is certified that error appears in the above-identified patent and that said Letters Patent is hereby corrected as shown below:

In the Claims

| Column | Line | |
|---|---|---|
| 44 | 4 | Claim 12, delete "1" and insert -- 1, -- |

Signed and Sealed this
Thirteenth Day of January, 2026

John A. Squires
*Director of the United States Patent and Trademark Office*